(12) United States Patent
Wood et al.

(10) Patent No.: US 11,539,066 B2
(45) Date of Patent: Dec. 27, 2022

(54) DEVICES AND METHODS FOR GENERATING ELECTRICAL CURRENT FROM METHANE

(71) Applicant: The Penn State Research Foundation, University Park, PA (US)

(72) Inventors: Thomas K. Wood, Port Matilda, PA (US); Michael J. McAnulty, Burke, VA (US)

(73) Assignee: The Penn State Research Foundation, University Park, PA (US)

( * ) Notice: Subject to any disclaimer, the term of this patent is extended or adjusted under 35 U.S.C. 154(b) by 832 days.

(21) Appl. No.: 16/462,701

(22) PCT Filed: Nov. 22, 2017

(86) PCT No.: PCT/US2017/063109
§ 371 (c)(1),
(2) Date: May 21, 2019

(87) PCT Pub. No.: WO2018/098349
PCT Pub. Date: May 31, 2018

(65) Prior Publication Data
US 2020/0144649 A1 May 7, 2020

Related U.S. Application Data

(60) Provisional application No. 62/445,871, filed on Jan. 13, 2017, provisional application No. 62/425,421, filed on Nov. 22, 2016.

(51) Int. Cl.
*H01M 8/16* (2006.01)
*C12N 1/20* (2006.01)
(Continued)

(52) U.S. Cl.
CPC ............. *H01M 8/16* (2013.01); *C12N 1/20* (2013.01); *C12P 5/023* (2013.01); *H01M 4/96* (2013.01); *H01M 8/0687* (2013.01)

(58) Field of Classification Search
CPC ........ H01M 8/16; H01M 8/0687; C12N 1/20; C12P 5/023
See application file for complete search history.

(56) References Cited

U.S. PATENT DOCUMENTS

| 2011/0123835 A1* | 5/2011 | Girguis | ................ | H01M 8/16 429/2 |
| 2014/0004427 A1* | 1/2014 | Medoff | ................ | H01M 8/06 429/505 |

(Continued)

FOREIGN PATENT DOCUMENTS

WO WO-2017046341 A1 3/2017

OTHER PUBLICATIONS

Soo V. W. et al., Reversing methanogenesis to capture methane for liquid biofuel precursors, Microb. Cell Fact., Jan. 2016, vol. 15, No. 11, pp. 1-15 (Year: 2016).*

(Continued)

*Primary Examiner* — Karie O'Neill Apicella
(74) *Attorney, Agent, or Firm* — Juhe K. Staple; Dinsmore & Shohl LLP

(57) ABSTRACT

Methods, microbial fuel cells and microbial consortia for generating electrical current are provided according to the present invention which include providing a microbial consortium to an anode chamber of a microbial fuel cell, wherein the microbial consortium includes: 1) an engineered methanogen that contains a heterologous nucleic acid sequence encoding methyl-coenzyme M reductase derived from an anaerobic methane oxidizer, 2) an exoelectrogen microbe that produces electrically-conductive appendages and/or one or more types of electron carrier, and 3) a sludge, (Continued)

methane-acclimated sludge, a sludge isolate component, a methane-acclimated sludge isolate component chosen from *Paracoccus* spp., *Geotoga* spp., *Geobacter* spp., *Methanosarcina* spp., *Garciella* spp., humic acids; or a combination of any two or more thereof.

20 Claims, 15 Drawing Sheets

Specification includes a Sequence Listing.

(51) Int. Cl.
 C12P 5/02 (2006.01)
 H01M 8/0662 (2016.01)
 H01M 4/96 (2006.01)

(56) References Cited

U.S. PATENT DOCUMENTS

| | | | |
|---|---|---|---|
| 2015/0111265 | A1 | 4/2015 | Lidstrom et al. |
| 2015/0147791 | A1 | 5/2015 | Ferry et al. |
| 2016/0168598 | A1 | 6/2016 | Leigh et al. |
| 2017/0101631 | A1 | 4/2017 | Koepke et al. |
| 2017/0107479 | A1 | 4/2017 | Scheller et al. |

OTHER PUBLICATIONS

Malvankar N.S et al., Biofilm conductivity is a decisive variable for high-current-density Geobactersulfurreducens microbial fuel cells, Energy & Environmental Science, 2012, vol. 5, pp. 5790-5797 (Year: 2012).*

Scheller S. et al., Artificial electron acceptors decouple archaeal methane oxidation from sulfate reduction, Science, Feb. 12, 2016, vol. 351, p. 703-707 (Year: 2016).*

Chang, In Seop et al., Electrochemically Active Bacteria (EAB) and Mediator-Less Microbial Fuel Cells, Journal of Microbiology and Biotechnology, 2006, vol. 16, No. 2, pp. 163-177 (Year: 2006).*

Chang, I. et al., Electrochemically Active Bacteria (EAB) and MediatorLess Microbial Fuel Cells, J. Microbiol. Biotechnol., 16(2): 163-177, 2006.

Evelyn, Mediator Combined Gaseous Substrate for Electricity Generation in Microbial Fuel Cells (MFCS) and Potential Integration of a MFC Into an Anaerobic Biofiltration System, University of Canterbury Master's Thesis, 2013.

Girguis, P. et al., Growth and Methane Oxidation Rates of Anaerobic Methanotrophic Archaea in a Continuous-Flow Bioreactor, Applied and Environmental Microbiology, 69(9): 5472-5482, Sep. 2003.

Malvankar N.et al., Biofilm conductivity is a decisive variable for high-curent-density *Geobacter sulfurreducens* microbial fuel cells, Energy Environ. Sci., 5:.5790-579, 2012.

Scheller, S. et al., Artificial electron acceptors decouple archaeal methane oxidation from sulfate reduction, Science, 351(6274): 703-707, Feb. 12, 2016.

Soo, V. et al., Reversing methanogenesis to capture methane for liquid biofuel precursors, Microb. Cell Fact., 15(11): 1-15, Jan. 2016.

Yin, Q. et al., Enhanced methane production in an anaerobic digestion and microbial electrolysis cell coupled system with co-cultivation of *Geobacter* and *Methanosarcina*». Journal of Environmental Sciences, 42: 210-214, Abstract, Apr. 2016.

Machine Translation of WO2017046341.

* cited by examiner

025

SEQUENCE LISTING

```
<160> NUMBER OF SEQ ID NOS: 10

<210> SEQ ID NO 1
<211> LENGTH: 579
<212> TYPE: PRT
<213> ORGANISM: Unknown
<220> FEATURE:
<223> OTHER INFORMATION: Methyl-coenzyme M reductase (Mcr), alpha
      subunit, from Anaerobic Methanotrophic archaeal population 1
      (ANME-1) from Black Sea mat

<400> SEQUENCE: 1

Met Pro Tyr Asn Asp Ile Gln His Asn Phe Leu Lys Ala Met Ser Asp
1               5                   10                  15

Lys Phe Ala Glu Lys Pro Glu Ser Thr Ala Thr Glu Phe Tyr Thr Tyr
            20                  25                  30

Gly Gly Ile Ala Gln Lys Gly Gly Met Arg Lys Arg Glu Phe Ile Ala
        35                  40                  45

Glu Ala Ser Lys Ile Val Asp Ser Arg Val Asn Ser Thr Pro Ala Tyr
    50                  55                  60

Asn Pro Asp Ala Gly Met Pro Gln Gly Gln Arg Tyr Leu Met Pro Tyr
65                  70                  75                  80

Met Met Asn His Thr Asp Ile Met Val Asn Ala Asp Asp Leu His Trp
                85                  90                  95

Ile Asn Asn Ala Ala Met Gln Gln Ala Trp Asp Asp Met Lys Arg Gly
            100                 105                 110

Ile Val Leu Gly Leu Asp Asp Ala His Gly Leu Leu Glu Ala Arg Leu
        115                 120                 125
```

```
Gly Lys Glu Val Thr Pro Asp Thr Ile Ser Asn Tyr Met Glu Val Leu
130                 135                 140

Asn His Ala Leu Pro Gly Gly Ala Val Ile Gln Glu His Met Val Glu
145                 150                 155                 160

Thr Lys Pro Met Leu Val Asn Asp Ser Tyr Ala Lys Ile Phe Ser Gly
                165                 170                 175

Asp Asp Asp Leu Val Asp Ser Val Asp Arg Arg Phe Ile Leu Asp Ile
            180                 185                 190

Asn Lys Glu Phe Ala Ala Gly Tyr Asp Lys Pro Gly Glu Gln Ala Asp
        195                 200                 205

Gln Leu Lys Asp Ala Ile Gly Lys Lys Ile Trp Gln Ile Leu Trp Met
210                 215                 220

Pro Thr Val Val Ala Arg Gln Thr Asp Gly Gly Thr Met Phe Arg Trp
225                 230                 235                 240

Val Gly Met Gln Val Gly Met Thr Met Ile Asn Ala Tyr Lys Leu Cys
                245                 250                 255

Ala Gly Glu Ser Val Thr Gly Glu Phe Ala Tyr Tyr Ala Lys His Ala
            260                 265                 270

Ala Val Val Gln Leu Ser Asn Tyr Met Pro Val Lys Arg Ala Arg Ser
        275                 280                 285

His Asn Glu Pro Gly Gly Met Pro Leu Gly Ile Asn Ala Asp Ser Thr
290                 295                 300

Arg Ser Pro Ala Leu Phe Pro Asn Asp Pro Ile Arg Ala Glu Leu Glu
305                 310                 315                 320

Ser Ile Ala Val Ala Ala Met Val Tyr Asp Gln Leu Trp Phe Gly Thr
                325                 330                 335

Tyr Met Ser Gly Gly Val Gly Phe Thr Gln Tyr Ala Ser Ala Thr Tyr
            340                 345                 350

Thr Asp Asn Ile Leu Glu Asp Phe Cys Tyr Lys Gly Cys Glu Ile Gly
        355                 360                 365

Leu Asp Tyr Ala Gly Gly Lys Met Ala Ser Ile Lys Gly Asp Lys Leu
370                 375                 380

Asn Met Asp Ile Leu Glu Glu Ile Ile Arg Ala Glu Asn Asp Tyr Ala
385                 390                 395                 400

Leu Thr Gln Tyr Glu Ala Tyr Pro Thr Val Ala Glu Ser His Phe Gly
                405                 410                 415

Gly Ser Val Arg Ala Cys Cys Ala Ala Ala Gly Cys Gly Ser Ala Val
            420                 425                 430

Ala Cys Ala Thr Gly Leu Ala Gln Pro Ala Leu Ser Ala Trp Ser Leu
        435                 440                 445

Ser Met Leu Gly His Tyr Glu Arg Val Gly Arg Leu Gly Phe Phe Gly
450                 455                 460

Tyr Asp Leu Gln Asp Gln Cys Thr Ala Cys Gly Ser Tyr Ser Tyr Gln
465                 470                 475                 480

Ser Asp Glu Gly Met Pro Phe Glu Met Arg Gly Val Asn Tyr Pro Asn
                485                 490                 495

Tyr Ala Met Asn Val Gly His Gln Ser Ala Tyr Ala Gly Leu Val Ala
            500                 505                 510

Gly Ala His Ser Ala Asn His Asp Ala Trp Val Leu Ser Pro Leu Trp
        515                 520                 525

Lys Val Ala Phe Ser Asp Arg Asp Leu Pro Phe Asp Arg Gly Tyr Val
530                 535                 540

Thr Arg Glu Tyr Gly Leu Gly Ala Asn Arg Glu Tyr Thr Lys Val Ala
```

```
                545                 550                 555                 560
Gly Glu Arg Asp Leu Ile Ile Ala Gly His Tyr Gly Arg Glu Pro Gly
                    565                 570                 575
Ala Lys Leu

<210> SEQ ID NO 2
<211> LENGTH: 1740
<212> TYPE: DNA
<213> ORGANISM: Unknown
<220> FEATURE:
<223> OTHER INFORMATION: Sequence encoding Methyl-coenzyme M reductase
      (Mcr), alpha subunit, from Anaerobic Methanotrophic archaeal
      population 1 (ANME-1) from Black Sea mat

<400> SEQUENCE: 2
atgccatata atgatataca gcacaatttc ctgaaagcga tgtcagataa gttcgcggag        60
aagccagaga gtacagcgac cgagttctat acgtacggcg gtatagcgca gaaaggagga       120
atgagaaaga gggagttcat agcggaagcg tcgaagatag tagatagccg agtcaactca       180
acgccagcat acaatccgga tgcgggtatg ccacaagggc agagatacct gatgccatac       240
atgatgaacc acacggacat catggtaaac gcagatgacc tgcactggat caacaatgcc       300
gcgatgcagc aggcctggga tgatatgaag agaggaattg tcctgggact ggacgatgca       360
cacggactgt tagaagcgag attgggcaag gaagttacgc cagatacaat aagcaactac       420
atggaagtgt tgaaccacgc gctgccgggt ggtgcggtaa ttcaggagca catggtagag       480
acgaagccga tgctggtgaa tgacagctat gccaagatat tctccggaga tgacgacctt       540
gtagattctg ttgacaggag attcattctg gacataaaca aggaattcgc agcaggctat       600
gataaaccgg gcgagcaggc cgaccagttg aaagatgcaa ttggcaagaa gatctggcag       660
atcctctgga tgccgactgt tgtagcacga cagacagatg gaggtacgat gttcagatgg       720
gtaggtatgc aggtcggaat gacaatgata acgcataca agctgtgtgc aggagaatca       780
gtcacgggtg agttcgcata ctacgcgaag cacgctgctg tggttcagtt gtcgaactac       840
atgccagtaa agagagcaag gtcacacaat gaacctggtg gtatgccatt aggtataaac       900
gcagacagta cacggtcacc agcgttgttc ccgaacgacc cgataagggc tgagctggag       960
agtatcgcag ttgcggctat ggtctatgac cagttgtggt tcggaacgta catgtcaggt      1020
ggtgtaggat tcacgcagta cgcaagtgcg acctacacgg acaacatcct ggaggacttc      1080
tgctacaagg gctgcgaaat cggactggat tacgcaggcg gcaagatggc ttcgataaag      1140
ggcgacaagc tcaacatgga catcctggag gagataataa gagcagagaa cgattatgca      1200
ctgacgcagt atgaagcata tccaacagta gcggaatctc acttcggtgg atctgttaga      1260
gcgtgctgtg cagcagcggg atgtggtagt gcagttgcat gcgcaacagg acttgcacaa      1320
cctgcattga gtgcgtggtc actgtctatg ctgggacact atgagcgtgt tggaagactc      1380
ggattcttcg ggtacgactt gcaagatcag tgtacggcat gcggctcgta ttcataccag      1440
agtgatgagg gaatgccatt tgagatgcgc ggtgtgaact atccgaacta cgcgatgaac      1500
gtcgggcacc agagtgcgta cgcaggtcta gttgctggag cacactctgc aaatcatgac      1560
gcatgggtgc tgtcaccgtt gtggaaagta gcgttctcgg accgtgacct accgttcgac      1620 cgтgggтtacg tgaccagaga gtacggactg ggtgcaaaca gagaatacac caaggtcgcc      1680
ggagagagag atctgattat agcaggtcac tacggcagag aacccggtgc aaaactgtaa      1740

<210> SEQ ID NO 3
```

```
<211> LENGTH: 433
<212> TYPE: PRT
<213> ORGANISM: Unknown
<220> FEATURE:
<223> OTHER INFORMATION: Methyl-coenzyme M reductase (Mcr), beta
      subunit, from Anaerobic Methanotrophic archaeal population 1
      (ANME-1) from Black Sea mat

<400> SEQUENCE: 3
```

Met Ala Asp Glu Ile Asp Leu Tyr Asp Asp Lys Gly Lys Lys Leu Ala
1               5                   10                  15

Ala Gly Val Pro Leu Gln Asn Ile Ser Pro Leu Lys Asn Ala Ala Ile
            20                  25                  30

Lys Lys Ile Val Asn Leu Thr Ile Arg Thr Gly Ala Val Asp Leu Ala
        35                  40                  45

Gly Leu Glu Lys Lys Phe Ala Thr Gly Ala Ile Ala Gly Arg Gly Met
50                  55                  60

Val Ile Arg Gly Val Asn Arg Asn Leu Pro Ile Val Asp Lys Ala Lys
65                  70                  75                  80

Glu Ile Ala Lys Ala Val Glu Asp Met Leu Arg Val Glu Ser Gly Asp
                85                  90                  95

Asp Thr Asn Val Glu Leu Ile Ala Gly Gly Lys Arg Met Met Val Gln
            100                 105                 110

Pro Pro Thr Ala Arg Ile Leu Ser Asp Tyr Ser Val Gly Leu Thr Ala
        115                 120                 125

Ser Met Gly Ala Leu Thr His Ala Ile Ile Asp Val Cys Asn Val Ser
130                 135                 140

Met Trp Asp Ala Pro Tyr Val His Ala Gly Val Trp Gly Met Tyr Pro
145                 150                 155                 160

Gln Asn Pro Asp Pro Gly Asp Gly Ala Val Lys Met Leu Val Asp Ile
                165                 170                 175

Pro Met Lys Asn Glu Gly Pro Gly Phe Thr Leu Arg Asn Ile Pro Val
            180                 185                 190

Asn His Leu Ala Ala Thr Val Arg Lys Arg Ala Met Gln Gly Ala Gly
        195                 200                 205

Leu Thr Met Ile Leu Glu Glu Ala Ala Gln Phe Glu Met Gly Asn Cys
210                 215                 220

Met Gly Pro His Glu Arg Gly His Leu Leu Asp Leu Ala Tyr Glu Gly
225                 230                 235                 240

Leu Asn Ala Asn Asn Leu Leu Tyr Ser Leu Ile Lys Asp Asn Gly Gln
                245                 250                 255

Asp Gly Ser Leu Gly Asp Val Ile Tyr Ala Ala Val Glu Lys Ala Lys
            260                 265                 270

Ala Asp Gly Val Ile Lys Ser Leu Lys Lys Met Pro Ser Gly Phe Thr
        275                 280                 285

Val Tyr Asp Ala Asp Asp Met Gln Leu Trp Asn Ala Tyr Ala Cys Thr
290                 295                 300

Ala Met Leu Ala Gly Val Cys Val Asn Cys Ala Ser Met Arg Ala Gly
305                 310                 315                 320

Gln Pro Val Pro Gly Asn Ile Met Gln Ala Cys Cys Leu Ile Glu Arg
                325                 330                 335

Glu Thr Gly Leu Pro Gly Pro Asp Phe Gly Met Ala Gln Gly Ala Ser
            340                 345                 350

Val Ser Ser Ser Phe Phe Ser His Ser Ile Tyr Gly Gly Gly Gly Pro
        355                 360                 365

```
Gly Val Phe Tyr Gly Asn His Ile Val Thr Arg His Ala Lys Gly Gln
        370                 375                 380

Phe Ile Pro Cys Phe Cys Ala Ala Met Cys Ile Asp Ala Asp Thr Met
385                 390                 395                 400

Tyr Phe Ser Pro Ala Arg Thr Ser Ala Leu Tyr Gly Glu Val Leu Gly
                405                 410                 415

Ala Ile Pro Glu Phe Ala Glu Pro Met Arg Ala Val Ala Glu Ala Ala
            420                 425                 430

Lys

<210> SEQ ID NO 4
<211> LENGTH: 1302
<212> TYPE: DNA
<213> ORGANISM: Unknown
<220> FEATURE:
<223> OTHER INFORMATION: Sequence encoding Methyl-coenzyme M reductase
      (Mcr), beta subunit, from Anaerobic Methanotrophic archaeal
      population 1 (ANME-1) from Black Sea mat

<400> SEQUENCE: 4
atggcagatg aaatagattt atatgacgac aaaggcaaga agttagcggc tggtgtacca      60
ttacagaaca tcagtccgct gaagaatgca gcgataaaga gatagttaa cctgaccatc     120 aggacaggtg ctgttgactt agcaggtctg gagaagaagt tcgcaaccgg cgcaattgcg    180
ggtagaggta tggtaatccg gggcgtaaat aggaacttac cgatagtgga caaagcgaaa    240
gagatagcga aagcagtaga ggacatgttg cgcgttgagt caggagacga cacaaacgta    300
gaattaatcg caggtggaaa agcaatgatg gtgcagccac caaccgcgag aatactatcc    360
gattattcgg ttggtctgac cgcgtcaatg ggtgcgctaa cgcatgcgat tattgacgtc    420
tgcaacgtga gtatgtggga tgcaccgtat gtgcatgctg gtgtgtgggg tatgtaccca    480
caaaatccgg atcccggtga tggggcagta agatgctcg tggatatacc gatgaagaat    540
gagggaccgg gtttcacgct gaggaacata cctgtgaacc acttagcagc gacagtgagg    600
aagagagcga tgcaaggtgc gggcctgacc atgattctgg aagaggcagc gcagttcgag    660
atgggtaact gtatgggacc gcatgagcgt ggtcacttc tggatcttgc gtatgaagga    720
ctgaatgcga caacctgtt gtatagcctg ataaaagaca acgggcagga cgggtcactt    780
ggcgatgtga tatacgctgc ggtggagaaa gcgaaagcag acggtgtgat aaagtcactg    840
aagaagatgc catccggatt cacagtgtat gacgcggatg acatgcagtt gtggaacgca    900
tacgcatgca cggctatgct tgcgggtgta tgtgtgaact gcgcatcaat gcgtgcaggt    960
cagccagtac cgggtaacat tatgcaagcc tgctgtctga tagagagaga gacaggactg   1020
cctggaccag actttggaat ggctcagggt gcgtcagtat cgagctcgtt cttctcgcac   1080
tccatatatg gaggcggtgg accgggtgtg ttctatggga accacatcgt gacgaggcat   1140
gcgaagggtc agttcatacc ctgtttctgt gctgcgatgt gcatagatgc ggacacgatg   1200
tatttctcac cagcgaggac gtcagcattg tatggggaag tattgggtgc aataccagaa   1260
tttgcagaac caatgagggc agttgcggag gctgccaagt aa                      1302

<210> SEQ ID NO 5
<211> LENGTH: 279
<212> TYPE: PRT
<213> ORGANISM: Unknown
<220> FEATURE:
<223> OTHER INFORMATION: Methyl-coenzyme M reductase (Mcr), gamma
      subunit, from Anaerobic Methanotrophic archaeal population 1
      (ANME-1) from Black Sea mat
```

<400> SEQUENCE: 5

```
Met Pro Gln Phe Thr Ala Gly Asn Ser His Val Ala Gln Asn Arg Arg
1               5                   10                  15

Asn Tyr Met Asp Pro Ser Tyr Lys Leu Glu Lys Leu Arg Asp Ile Pro
            20                  25                  30

Glu Glu Asp Ile Val Arg Leu Leu Ala His Arg Ala Pro Gly Glu Glu
        35                  40                  45

Tyr Lys Ser Ile His Pro Pro Leu Glu Glu Met Glu Pro Asp Cys
    50                  55                  60

Ala Val Arg Gln Ile Val Lys Pro Thr Glu Gly Ala Ala Ala Gly Asp
65                  70                  75                  80

Arg Ile Arg Tyr Val Gln Tyr Thr Asp Ser Met Phe Phe Ser Pro Ile
                85                  90                  95

Thr Pro Tyr Gln Arg Ala Trp Glu Ala Leu Asn Arg Tyr Lys Gly Val
            100                 105                 110

Asp Pro Gly Val Leu Ser Gly Arg Thr Ile Ile Glu Ala Arg Glu Arg
        115                 120                 125

Asp Ile Glu Lys Ile Ala Lys Ile Glu Val Asp Cys Glu Leu Tyr Asp
    130                 135                 140

Thr Ala Arg Thr Gly Leu Arg Gly Arg Thr Val His Gly His Ala Val
145                 150                 155                 160

Arg Leu Asp Lys Asp Gly Met Met Phe Asp Ala Leu Arg Arg Trp Ser
                165                 170                 175

Arg Gly Ala Asp Gly Thr Val Thr Tyr Val Lys Asp Met Ile Gly Gly
            180                 185                 190

Ala Met Asp Lys Glu Val Thr Leu Gly Lys Pro Leu Ser Asp Ala Glu
        195                 200                 205

Leu Leu Lys Lys Thr Thr Met Tyr Arg Asn Ala Gln Gly Gly Val Trp
    210                 215                 220

Gln Glu Ala Asp Asp Pro Glu Ser Met Asp Val Thr Ala Gln Ile His
225                 230                 235                 240

Trp Lys Arg Ser Val Gly Gly Phe Gln Pro Trp Ala Lys Met Lys Asp
                245                 250                 255

Ile Lys Gly Gly Lys Lys Asp Val Gly Val Lys Asn Leu Lys Leu Phe
            260                 265                 270

Thr Pro Arg Gly Gly Val Glu
        275
```

<210> SEQ ID NO 6
<211> LENGTH: 840
<212> TYPE: DNA
<213> ORGANISM: Unknown
<220> FEATURE:
<223> OTHER INFORMATION: Sequence encoding Methyl-coenzyme M reductase (Mcr), gamma subunit, from Anaerobic Methanotrophic archaeal population 1 (ANME-1) from Black Sea mat

<400> SEQUENCE: 6

```
atgccacaat ttacagcggg aaatagccat gtagcacaaa acagaagaaa ctacatggac      60
ccaagctaca aattagagaa actgagagac ataccagaag aagacattgt gagattgctt     120
gcgcaccgtg caccgggaga ggagtacaag agcatccatc caccattgga agagatggaa     180
gagccggact gcgcggttcg tcagatagtg aagccaacag aaggcgcagc agcaggtgac     240
aggatacgat acgtgcagta caccgattcg atgttcttct caccgataac gccttaccag     300
```

```
cgtgcatggg aagcattgaa ccgatataag ggtgtggacc caggagtgct gtcaggaagg      360
acgatcatag aagcacgaga gcgagatata gagaagatag cgaaaatcga ggttgattgc      420
gagctatacg atacagcaag aaccggcctg agaggaagga cagtgcacgg gcacgcagtc      480
cgactggaca aggacggtat gatgttcgat gcactacgaa gatggtcaag aggtgcagat      540
ggaacagtaa cctacgtgaa ggatatgatc ggcggtgcaa tggacaagga agtaacgtta      600
ggaaagccac tgtctgatgc agagctgctg aagaaaacga ctatgtacag gaacgcacag      660
ggcggagtct ggcaagaagc ggatgatccc gagtcaatgg acgtaactgc tcagatacac      720
tggaaaaggt cagtaggtgg attccaacca tgggcaaaga tgaaggacat aaaaggtgga      780
aagaaggacg taggcgtgaa gaacttgaaa ttatttacac caagaggagg agtggaataa      840
```

<210> SEQ ID NO 7
<211> LENGTH: 50
<212> TYPE: DNA
<213> ORGANISM: Artificial Sequence
<220> FEATURE:
<223> OTHER INFORMATION: forward primer for amplifying v3-v4
      hypervariable region of 16S rDNA of prokaryotes
<220> FEATURE:
<221> NAME/KEY: misc_feature
<222> LOCATION: (42)..(42)
<223> OTHER INFORMATION: n is a, c, g, or t

<400> SEQUENCE: 7
tcgtcggcag cgtcagatgt gtataagaga cagcctacgg gnbgcascag                 50

<210> SEQ ID NO 8
<211> LENGTH: 33
<212> TYPE: DNA
<213> ORGANISM: Artificial Sequence
<220> FEATURE:
<223> OTHER INFORMATION: 5' adapter

<400> SEQUENCE: 8
tcgtcggcag cgtcagatgt gtataagaga cag                                   33

<210> SEQ ID NO 9
<211> LENGTH: 55
<212> TYPE: DNA
<213> ORGANISM: Artificial Sequence
<220> FEATURE:
<223> OTHER INFORMATION: reverse primer for amplifying v3-v4
      hypervariable region of 16S rDNA of prokaryotes
<220> FEATURE:
<221> NAME/KEY: misc_feature
<222> LOCATION: (41)..(41)
<220> FEATURE:
<221> NAME/KEY: misc_feature
<222> LOCATION: (41)..(41)
<223> OTHER INFORMATION: n is a, c, g, or t

<400> SEQUENCE: 9
gtctcgtggg ctcggagatg tgtataagag acaggactac nvgggtatct aatcc           55

<210> SEQ ID NO 10
<211> LENGTH: 34
<212> TYPE: DNA
<213> ORGANISM: Artificial Sequence
<220> FEATURE:
<223> OTHER INFORMATION: 5' adapter

<400> SEQUENCE: 10
gtctcgtggg ctcggagatg tgtataagag acag                                  34

DEVICES AND METHODS FOR GENERATING ELECTRICAL CURRENT FROM METHANE

REFERENCE TO RELATED APPLICATIONS

This application claims priority to U.S. Provisional Patent Application Ser. Nos. 62/425,421, filed Nov. 22, 2016 and 62/445,871 filed Jan. 13, 2017, the entire content of both of which is incorporated herein by reference.

GOVERNMENT SUPPORT

This invention was made with government support under Grant No. DE-AR0000431 awarded by the Department of Energy. The Government has certain rights in the invention.

SEQUENCE LISTING

The instant application contains a Sequence Listing which has been submitted electronically in ASCII format and is hereby incorporated by reference in its entirety. Said ASCII copy, created on Jan. 7, 2020, is named 36PST86402PA_ST25.txt and is 18.5 kilobytes in size.

FIELD OF THE INVENTION

Methods, systems and microbial consortia of the present invention are described herein which relate generally to microbial fuel cells. Methods, systems and microbial consortia of the present invention are described herein which relate specifically to microbial fuel cells, microbial consortia and methods of their use for generating methane.

BACKGROUND OF THE INVENTION

Electrical current may be generated from organic substrates in microbial fuel cells (hereinafter, "MFCs"). In MFCs, microbes transfer electrons extracellularly (hereinafter, "exoelectrogens"), depositing electrons on an anode in an anode chamber. From the anode chamber, electrons migrate to a cathode in a cathode chamber to create an electrical current. At the cathode, the electrons are passed to an electron acceptor. In a dual-chamber setup, a proton-conducting membrane is used between the anode chamber and the cathode chamber to complete a circuit by allowing excess positive charge in the anode (such as, e.g., in the form of protons) to migrate to the cathode. MFCs have generated electrical current from substrates of natural and artificial sources (including, e.g., acetate, glucose, and wastewaters).

With regard to microbes used in MFCs, most MFCs use either exoelectrogens that make electrically-conductive pili, such as, e.g., *Geobacter sulfurreducens*, or exoelectrogens that secrete redox active electron shuttles (also called electron carriers herein), such as, e.g., *Shewanella oneidensis*. Additionally, microbes that are not naturally capable of externally transferring electrons may generate electrical current in MFCs through the use of externally supplied electron shuttle molecules, such as, e.g., thionine, neutral red, or methylene blue. However, exogenously supplied electron shuttle molecules may be toxic and expensive.

With regard to substrates used in MFCs, methane is a potential substrate. Methane is an energy dense fuel with decreased carbon dioxide (i.e., $CO_2$) emissions per unit energy. Thus, extraction of methane from shale deposits has gained considerable attention. However, methane (i.e., $CH_4$) is also a potent greenhouse gas that is more damaging to the atmosphere than carbon dioxide (i.e., $CO_2$). To exploit methane as an energy source, some chemical plants employ Fischer-Tropsch processes to convert methane into liquid fuels. However, such processes are complex and require large-scale investment and transporting methane leads to large greenhouse gas emissions. Therefore, processes for converting methane into liquid fuels remain a challenging area.

In contrast, the biological conversion of methane may be economically and environmentally sustainable. The anaerobic oxidation of methane (i.e., AOM) may be a key regulator of global fluxes of methane and the carbon cycle. However, AOM is a little-understood biological process driven by natural consortia including anaerobic methanotrophic arachae (hereinafter, "ANME") and syntrophic bacteria. Such natural consortia of ANME and syntrophic bacteria have not been successfully isolated and separate cultivation of ANME and syncotrophic bacteria has not been reported. Moreover, only negligible electrical current has been produced using natural uncultured anaerobic methane-oxidizing consortia isolated from oceanic sediment with methane as a substrate.

Thus, ongoing needs exist for devices and methods for generating electrical current from methane.

SUMMARY OF THE INVENTION

Methods, microbial fuel cells and microbial consortia for generating electrical current are provided according to the present invention which include a microbial consortium, wherein the microbial consortium includes: 1) an engineered methanogen that contains a heterologous nucleic acid sequence encoding methyl-coenzyme M reductase, 2) an exoelectrogen microbe that produces electrically-conductive appendages and/or one or more types of electron carrier, and 3) a sludge or sludge isolate component. According to aspects of the present invention, the sludge or sludge isolate component includes a microbe and/or humic acids wherein the microbe is chosen from *Paracoccus* spp.; *Geotoga* spp.; *Geobacter* spp.; *Methanosarcina* spp.; *Garciella* spp.; and a combination of any two or more thereof.

Methods, microbial fuel cells and microbial consortia for generating electrical current are provided according to the present invention which include a microbial consortium, wherein the microbial consortium includes: 1) an engineered methanogen that contains a heterologous nucleic acid sequence encoding methyl-coenzyme M reductase and a heterologous nuclei acid sequence encoding puromycin resistance 2) an exoelectrogen microbe that produces electrically-conductive appendages and/or one or more types of electron carrier, and 3) a sludge or sludge isolate component. According to aspects of the present invention, the sludge or sludge isolate component includes a microbe and/or humic acids wherein the microbe is chosen from *Paracoccus* spp.; *Geotoga* spp.; *Geobacter* spp.; *Methanosarcina* spp.; *Garciella* spp.; and a combination of any two or more thereof.

According to preferred aspects of the present invention, puromycin is included in the anode chamber of a microbial fuel cell, wherein the anode chamber contains a microbial consortium, wherein the microbial consortium includes: 1) an engineered methanogen that contains a heterologous nucleic acid sequence encoding methyl-coenzyme M reductase and a heterologous nuclei acid sequence encoding puromycin resistance 2) an exoelectrogen microbe that produces electrically-conductive appendages and/or one or more types of electron carrier, and 3) a sludge or sludge isolate component and wherein the puromycin is included in amounts in the range of about 0.5 micrograms/milliliter to about 10 micrograms/milliliter, such as about 0.75 micrograms/milliliter to about 7.5 micrograms/milliliter, such as about 1 microgram/milliliter to about 5 micrograms/milliliter, such as about 2 micrograms/milliliter of fluid in the anode chamber.

A microbial fuel cell according to aspects of the present invention includes: 1) an anode chamber including an anode, a first fluid and methane, wherein the first fluid includes a microbial consortium which includes: a) an engineered methanogen that contains a heterologous nucleic acid sequence encoding methyl-coenzyme M reductase, b) an exoelectrogen microbe that produces electrically-conductive appendages and/or one or more types of electron carrier, and c) a sludge or sludge isolate component; 2) a cathode chamber in selective communication with the anode chamber, the cathode chamber comprising a cathode in electrical communication with the anode and a second fluid, and 3) a cation exchange membrane disposed between the anode chamber and the cathode chamber, wherein the microbial fuel cell generates electrical current anaerobically. According to aspects of the present invention, the sludge or sludge isolate component includes a microbe and/or humic acids wherein the microbe is chosen from *Paracoccus* spp.; *Geotoga* spp.; *Geobacter* spp.; *Methanosarcina* spp.; *Garciella* spp.; and a combination of any two or more thereof.

Methods, microbial fuel cells and microbial consortia for generating electrical current are provided according to the present invention which include providing a microbial consortium to an anode chamber of a microbial fuel cell containing a first fluid, wherein the microbial consortium includes: 1) an engineered *Methanosarcina acetivorans* that contains a heterologous nucleic acid sequence encoding methyl-coenzyme M reductase, 2) an exoelectrogen microbe that produces electrically-conductive appendages and/or one or more types of electron carrier, and 3) a sludge or sludge isolate component wherein the sludge or sludge isolate component includes a microbe and/or humic acids, wherein the microbe is chosen from *Paracoccus* spp.; *Geotoga* spp.; *Geobacter* spp.; *Methanosarcina* spp.; *Garciella* spp.; and a combination of any two or more thereof.

Methods, microbial fuel cells and microbial consortia for generating electrical current are provided according to the present invention which include providing a microbial consortium to an anode chamber of a microbial fuel cell containing a first fluid, wherein the microbial consortium includes: 1) an engineered *Methanosarcina acetivorans* that contains a heterologous nucleic acid sequence encoding methyl-coenzyme M reductase and a heterologous nuclei acid sequence encoding puromycin resistance 2) an exoelectrogen microbe that produces electrically-conductive appendages and/or one or more types of electron carrier, and 3) a sludge or sludge isolate component wherein the sludge or sludge isolate component includes a microbe and/or humic acids, wherein the microbe is chosen from *Paracoccus* spp.; *Geotoga* spp.; *Geobacter* spp.; *Methanosarcina* spp.; *Gardena* spp.; and a combination of any two or more thereof. Puromycin may be included in amounts in the range of about 0.5 micrograms/milliliter to about 10 micrograms/milliliter, such as about 0.75 micrograms/milliliter to about 7.5 micrograms/milliliter, such as about 1 microgram/milliliter to about 5 micrograms/milliliter, such as about 2 micrograms/milliliter of the first fluid in the anode chamber.

A microbial fuel cell according to aspects of the present invention includes: 1) an anode chamber including an anode, a first fluid and methane, wherein the first fluid includes a microbial consortium which includes: a) an engineered *Methanosarcina acetivorans* that contains a heterologous nucleic acid sequence encoding methyl-coenzyme M reductase, b) an exoelectrogen microbe that produces electrically-conductive appendages and/or one or more types of electron carrier, and c) a sludge or sludge isolate component; 2) a cathode chamber in selective communication with the anode chamber, the cathode chamber comprising a cathode in electrical communication with the anode and a second fluid, and 3) a cation exchange membrane disposed between the anode chamber and the cathode chamber, wherein the microbial fuel cell generates electrical current anaerobically. According to aspects of the present invention, the sludge or sludge isolate component includes a microbe and/or humic acids wherein the microbe is chosen from *Paracoccus* spp.; *Geotoga* spp.; *Geobacter* spp.; *Methanosarcina* spp.; *Garciella* spp.; and a combination of any two or more thereof.

Methods, microbial fuel cells and microbial consortia for generating electrical current are provided according to the present invention which include providing a microbial consortium to an anode chamber of a microbial fuel cell containing a first fluid, wherein the microbial consortium includes: 1) an engineered methanogen that contains a heterologous nucleic acid sequence encoding methyl-coenzyme M reductase, 2) an exoelectrogen microbe that produces electrically-conductive appendages and/or one or more types of electron carrier, and 3) a methane-acclimated sludge or a methane-acclimated sludge isolate component. According to aspects of the present invention, the methane-acclimated sludge or methane-acclimated sludge isolate component includes a methane-acclimated microbe and/or humic acids wherein the methane-acclimated microbe is a methane-acclimated microbe chosen from methane-acclimated *Paracoccus* spp.; methane-acclimated *Geotoga* spp.; methane-acclimated *Geobacter* spp.; methane-acclimated *Methanosarcina* spp.; methane-acclimated *Garciella* spp.; and a combination of any two or more thereof.

Methods, microbial fuel cells and microbial consortia for generating electrical current are provided according to the present invention which include providing a microbial consortium to an anode chamber of a microbial fuel cell containing a first fluid, wherein the microbial consortium includes: 1) an engineered methanogen that contains a heterologous nucleic acid sequence encoding methyl-coenzyme M reductase and a heterologous nuclei acid sequence encoding puromycin resistance, 2) an exoelectrogen microbe that produces electrically-conductive appendages and/or one or more types of electron carrier, and 3) a methane-acclimated sludge or a methane-acclimated sludge isolate component. According to aspects of the present invention, the methane-acclimated sludge or methane-acclimated sludge isolate component includes a methane-acclimated microbe and/or humic acids wherein the methane-acclimated microbe is a methane-acclimated microbe chosen from methane-acclimated *Paracoccus* spp.; methane-acclimated *Geotoga* spp.; methane-acclimated *Geobacter* spp.; methane-acclimated *Methanosarcina* spp.; methane-acclimated *Garciella* spp.; and a combination of any two or more thereof. Puromycin may be included in amounts in the range of about 0.5 micrograms/milliliter to about 10 micrograms/milliliter, such as about 0.75 micrograms/milliliter to about 7.5 micrograms/milliliter, such as about 1 microgram/milliliter to about 5 micrograms/milliliter, such as about 2 micrograms/milliliter of the first fluid in the anode chamber.

A microbial fuel cell according to aspects of the present invention includes: 1) an anode chamber including an anode, a first fluid and methane, wherein the first fluid includes a microbial consortium which includes: a) an engineered methanogen that contains a heterologous nucleic acid sequence encoding methyl-coenzyme M reductase, b) an exoelectrogen microbe that produces electrically-conductive appendages and/or one or more types of electron carrier, and c) a methane-acclimated sludge or a methane-acclimated sludge isolate component; 2) a cathode chamber in selective communication with the anode chamber, the cathode chamber comprising a cathode in electrical communication with the anode and a second fluid, and 3) a cation exchange membrane disposed between the anode chamber and the cathode chamber, wherein the microbial fuel cell generates electrical current anaerobically. According to aspects of the present invention, the methane-acclimated sludge or methane-acclimated sludge isolate component includes a methane-acclimated microbe and/or humic acids wherein the methane-acclimated microbe is a methane-acclimated microbe chosen from methane-acclimated *Paracoccus* spp.; methane-acclimated *Geotoga* spp.; methane-acclimated *Geobacter* spp.; methane-acclimated *Methanosarcina* spp.; methane-acclimated *Garciella* spp.; and a combination of any two or more thereof.

Methods, microbial fuel cells and microbial consortia for generating electrical current are provided according to the present invention which include providing a microbial consortium to an anode chamber of a microbial fuel cell containing a first fluid, wherein the microbial consortium includes: 1) an engineered *Methanosarcina acetivorans* that contains a heterologous nucleic acid sequence encoding methyl-coenzyme M reductase, 2) an exoelectrogen microbe that produces electrically-conductive appendages and/or one or more types of electron carrier, and 3) a methane-acclimated sludge or a methane-acclimated sludge isolate component wherein the methane-acclimated sludge or methane-acclimated sludge isolate component includes a methane-acclimated microbe and/or humic acids, wherein the a methane-acclimated microbe is a methane-acclimated microbe chosen from methane-acclimated *Paracoccus* spp.; methane-acclimated *Geotoga* spp.; methane-acclimated *Geobacter* spp.; methane-acclimated *Methanosarcina* spp.; methane-acclimated *Garciella* spp.; and a combination of any two or more thereof.

Methods, microbial fuel cells and microbial consortia for generating electrical current are provided according to the present invention which include providing a microbial consortium to an anode chamber of a microbial fuel cell containing a first fluid, wherein the microbial consortium includes: 1) an engineered *Methanosarcina acetivorans* that contains a heterologous nucleic acid sequence encoding methyl-coenzyme M reductase and a heterologous nuclei acid sequence encoding puromycin resistance, 2) an exoelectrogen microbe that produces electrically-conductive appendages and/or one or more types of electron carrier, and 3) a methane-acclimated sludge or a methane-acclimated sludge isolate component wherein the methane-acclimated sludge or methane-acclimated sludge isolate component includes a methane-acclimated microbe and/or humic acids, wherein the a methane-acclimated microbe is a methane-acclimated microbe chosen from methane-acclimated *Paracoccus* spp.; methane-acclimated *Geotoga* spp.; methane-acclimated *Geobacter* spp.; methane-acclimated *Methanosarcina* spp.; methane-acclimated *Garciella* spp.; and a combination of any two or more thereof. Puromycin may be included in amounts in the range of about 0.5 micrograms/milliliter to about 10 micrograms/milliliter, such as about 0.75 micrograms/milliliter to about 7.5 micrograms/milliliter, such as about 1 microgram/milliliter to about 5 micrograms/milliliter, such as about 2 micrograms/milliliter of the first fluid in the anode chamber.

A microbial fuel cell according to aspects of the present invention includes: 1) an anode chamber including an anode, a first fluid and methane, wherein the first fluid includes a microbial consortium which includes: a) an engineered *Methanosarcina acetivorans* that contains a heterologous nucleic acid sequence encoding methyl-coenzyme M reductase, b) an exoelectrogen microbe that produces electrically-conductive appendages and/or one or more types of electron carrier, and c) a methane-acclimated sludge or a methane-acclimated sludge isolate component; 2) a cathode chamber in selective communication with the anode chamber, the cathode chamber comprising a cathode in electrical communication with the anode and a second fluid, and 3) a cation exchange membrane disposed between the anode chamber and the cathode chamber, wherein the microbial fuel cell generates electrical current anaerobically. According to aspects of the present invention, the methane-acclimated sludge or methane-acclimated sludge isolate component includes a methane-acclimated microbe and/or humic acids wherein the methane-acclimated microbe is a methane-acclimated microbe chosen from methane-acclimated *Paracoccus* spp.; methane-acclimated *Geotoga* spp.; methane-acclimated *Geobacter* spp.; methane-acclimated *Methanosarcina* spp.; methane-acclimated *Garciella* spp.; and a combination of any two or more thereof.

Cytochrome C is optionally included in the first fluid in the anode chamber to achieve a concentration in the range of about 200 nM-200 µM, such as 250 nM-100 µM. In particular aspects, cytochrome C is included in the first fluid in the anode chamber to achieve a concentration in the range of about 500 nM-50 µM, such as 10 µM-30 µM. In further aspects, cytochrome C is included in the first fluid in the anode chamber to achieve a concentration of about 20 µM.

According to aspects of the present invention, the first fluid includes an inoculation medium anolyte.

According to aspects of the present invention, the second fluid includes a catholyte.

A microbial consortium for generating electrical current from methane is provided according to the present invention which includes: 1) an engineered methanogen that contains a heterologous nucleic acid sequence encoding methyl-coenzyme M reductase, 2) an exoelectrogen microbe that produces electrically-conductive appendages and/or one or more types of electron carrier, and 3) a sludge or sludge isolate component. According to aspects of the present invention, the sludge or sludge isolate component includes a microbe and/or humic acids wherein the microbe is chosen from *Paracoccus* spp.; *Geotoga* spp.; *Geobacter* spp.; *Methanosarcina* spp.; *Gardener* spp.; and a combination of any two or more thereof.

A microbial consortium for generating electrical current from methane is provided according to the present invention which includes: 1) an engineered methanogen that contains a heterologous nucleic acid sequence encoding methyl-coenzyme M reductase and a heterologous nuclei acid sequence encoding puromycin resistance, 2) an exoelectrogen microbe that produces electrically-conductive appendages and/or one or more types of electron carrier, and 3) a sludge or sludge isolate component. According to aspects of the present invention, the sludge or sludge isolate component includes a microbe and/or humic acids wherein the microbe is chosen from *Paracoccus* spp.; *Geotoga* spp.; *Geobacter* spp.; *Methanosarcina* spp.; *Garciella* spp.; and a combination of any two or more thereof.

A microbial consortium for generating electrical current from methane is provided according to the present invention which includes: 1) an engineered *Methanosarcina acetivorans* that contains a heterologous nucleic acid sequence encoding methyl-coenzyme M reductase, 2) an exoelectrogen microbe that produces electrically-conductive appendages and/or one or more types of electron carrier, and 3) a sludge or sludge isolate component. According to aspects of the present invention, the sludge or sludge isolate component includes a microbe and/or humic acids wherein the microbe is chosen from *Paracoccus* spp.; *Geotoga* spp.; *Geobacter* spp.; *Methanosarcina* spp.; *Gardena* spp.; and a combination of any two or more thereof.

A microbial consortium for generating electrical current from methane is provided according to the present invention which includes: 1) an engineered *Methanosarcina acetivorans* that contains a heterologous nucleic acid sequence encoding methyl-coenzyme M reductase and a heterologous nuclei acid sequence encoding puromycin resistance, 2) an exoelectrogen microbe that produces electrically-conductive appendages and/or one or more types of electron carrier, and 3) a sludge or sludge isolate component. According to aspects of the present invention, the sludge or sludge isolate component includes a microbe and/or humic acids wherein the microbe is chosen from *Paracoccus* spp.; *Geotoga* spp.; *Geobacter* spp.; *Methanosarcina* spp.; *Garciella* spp.; and a combination of any two or more thereof.

A microbial consortium for generating electrical current from methane is provided according to the present invention, the microbial consortium including: 1) an engineered methanogen that contains a heterologous nucleic acid sequence encoding methyl-coenzyme M reductase; 2) an exoelectrogen microbe that produces electrically-conductive appendages and/or one or more types of electron carrier; and 3) a methane-acclimated sludge or a methane-acclimated sludge isolate component chosen from methane-acclimated *Paracoccus* spp., methane-acclimated *Geotoga* spp., methane-acclimated *Geobacter* spp., methane-acclimated *Methanosarcina* spp., methane-acclimated *Garciella* spp., humic acids, and a combination of any two or more thereof. According to aspects of the present invention, the methane-acclimated sludge or methane-acclimated sludge isolate component includes a methane-acclimated microbe and/or humic acids wherein the methane-acclimated microbe is chosen from methane-acclimated *Paracoccus* spp.; methane-acclimated *Geotoga* spp.; methane-acclimated *Geobacter* spp.; methane-acclimated *Methanosarcina* spp.; methane-acclimated *Garciella* spp.; and a combination of any two or more thereof.

A microbial consortium for generating electrical current from methane is provided according to the present invention, the microbial consortium including: 1) an engineered methanogen that contains a heterologous nucleic acid sequence encoding methyl-coenzyme M reductase and a heterologous nuclei acid sequence encoding puromycin resistance; 2) an exoelectrogen microbe that produces electrically-conductive appendages and/or one or more types of electron carrier; and 3) a methane-acclimated sludge or a methane-acclimated sludge isolate component chosen from methane-acclimated *Paracoccus* spp., methane-acclimated *Geotoga* spp., methane-acclimated *Geobacter* spp., methane-acclimated *Methanosarcina* spp., methane-acclimated *Garciella* spp., humic acids, and a combination of any two or more thereof. According to aspects of the present invention, the methane-acclimated sludge or methane-acclimated sludge isolate component includes a methane-acclimated microbe and/or humic acids wherein the methane-acclimated microbe is chosen from methane-acclimated *Paracoccus* spp.; methane-acclimated *Geotoga* spp.; methane-acclimated *Geobacter* spp.; methane-acclimated *Methanosarcina* spp.; methane-acclimated *Garciella* spp.; and a combination of any two or more thereof.

A microbial consortium for generating electrical current from methane is provided according to the present invention, the microbial consortium including: 1) an engineered *Methanosarcina acetivorans* that contains a heterologous nucleic acid sequence encoding methyl-coenzyme M reductase; 2) an exoelectrogen microbe that produces electrically-conductive appendages and/or one or more types of electron carrier; and 3) a methane-acclimated sludge isolate component chosen from methane-acclimated *Paracoccus* spp., methane-acclimated *Geotoga* spp., methane-acclimated *Geobacter* spp., methane-acclimated *Methanosarcina* spp., methane-acclimated *Garciella* spp., humic acids, and a combination of any two or more thereof.

A microbial consortium for generating electrical current from methane is provided according to the present invention, the microbial consortium including: 1) an engineered *Methanosarcina acetivorans* that contains a heterologous nucleic acid sequence encoding methyl-coenzyme M reductase and a heterologous nuclei acid sequence encoding puromycin resistance; 2) an exoelectrogen microbe that produces electrically-conductive appendages and/or one or more types of electron carrier; and 3) a methane-acclimated sludge isolate component chosen from methane-acclimated *Paracoccus* spp., methane-acclimated *Geotoga* spp., methane-acclimated *Geobacter* spp., methane-acclimated *Methanosarcina* spp., methane-acclimated *Garciella* spp., humic acids, and a combination of any two or more thereof.

According to aspects of the present invention, a microbial consortium includes an engineered methanogen wherein the heterologous nucleic acid sequence encoding methyl-coenzyme M reductase derived from an anaerobic methane oxidizer comprises SEQ ID NO:2 or a variant thereof encoding methyl-coenzyme M reductase submit alpha or a variant thereof, SEQ ID NO:4 or a variant thereof encoding methyl-coenzyme M reductase submit beta or a variant thereof and SEQ ID NO:6 or a variant thereof encoding methyl-coenzyme M reductase submit gamma or a variant thereof.

Optionally, the heterologous nucleic acid sequence encoding the methyl-coenzyme M reductase is an mRNA sequence or a DNA sequence.

According to aspects of the present invention, the heterologous nucleic acid sequence encoding the methyl-coenzyme M reductase is present in a vector, such as in a plasmid.

According to aspects of the present invention, the engineered *Methanosarcina acetivorans* expresses non-native methyl-coenzyme M reductase.

According to aspects of the present invention, the engineered *Methanosarcina acetivorans* is air-adapted.

According to aspects of the present invention, the exoelectrogen microbe is chosen from *Geobacter* spp., *Shewanella* spp., or combination thereof.

According to aspects of the present invention, the *Geobacter* spp. are chosen from the group consisting of: *Geobacter anodireducens*, *Geobacter argillaceus*, *Geobacter bemidjiensis*, *Geobacter bremensis*, *Geobacter chapellei*, *Geobacter daltonii*, *Geobacter grbiciae*, *Geobacter hydrogenophilus*, *Geobacter lovley*, *Geobacter luticola*, *Geobacter metallireducens*, *Geobacter pelophilus*, *Geobacter pickeringii*, *Geobacter psychrophilus*, *Geobacter soli*, *Geobacter sulfurreducens*, *Geobacter thiogenes*, *Geobacter toluenoxy-*

*dans, Geobacter uraniireducens*, and a combination of any two or more thereof; and the *Shewanella* spp. are selected from the group consisting of: *Shewanella abyssi, Shewanella aestuarii, Shewanella algae, Shewanella algidipiscicola, Shewanella amazonensis, Shewanella aquinzarina, Shewanella arctica, Shewattella atlantica, Shewanella baltica, Shewanella basaltis, Shewanella benthica, Shewanella canadensis, Shewanella chilikensis, Shewanella colwelliana, Shewanella corallii, Shewanella decolorationis, Shewanella denitrificans, Shewanella dokdonensis, Shewanella donghaensis, Shewanella fidelis, Shewanella fodinae, Shewanella frigidinarina, Shewanella gaetbuli, Shewanella gelidintarina, Shewanella glacialtpiscicola, Shewanella hafniensis, Shewanella halifaxensis, Shewanella halitois, Shewanella hanedai, Shewanella indica, Shewanella irciniae, Shewanella japonica, Shewanella kaireitica, Shewanella litorisediminis, Shewattella livingstonensis, Shewanella loihica, Shewanella mangrovi, Shewanella marina, Shewanella marinintestina, Shewanella marisflavi, Shewanella morhuae, Shewanella olleyana, Shewanella oneidensis, Shewanella piezotolerans, Shewanella pacifica, Shewanella pealeana, Shewanella piezotolerans, Shewanella penumatophori, Shewanella putrefaciens, Shewanella sairae, Shewanella schegeliana, Shewanella sediminis, Shewanella seohaensis, Shewanella spongiae, Shewanella surugensis, Shewanella upenei, Shewanella vesiculosa, Shewanella violacea, Shewanella waksmanii, Shewanella woodyi, Shewanella xiamenensis*, and a combination of any two or more thereof.

According to aspects of the present invention, the *Geobacter* spp. are chosen from: *Geobacter metallireducens, Geobacter sulfurreducens*, and a combination thereof; and the *Shewanella* spp. are chosen from: *Shewanella putrelciens* IR-1, *Shewanella oneidensis* DSP10, and a combination thereof.

According to aspects of the present invention, the exoelectrogen microbe is chosen from *Geobacter* spp.

According to aspects of the present invention, the exoelectrogen microbe is *Geobacter sulfurreducens*.

According to aspects of the present invention, the exoelectrogen microbe is *Geobacter metallireducens*.

According to aspects of the present invention, the sludge isolate component is chosen from: *Paracoccus* spp., *Geotoga* spp., *Garciella* spp., humic acids, and a combination of any two or more thereof. According to aspects of the present invention, wherein the sludge isolate component is chosen from *Paracoccus* spp. According to aspects of the present invention, wherein the sludge isolate component is a humic acid.

According to aspects of the present invention, the methane-acclimated sludge isolate component is chosen from: methane-acclimated *Paracoccus* spp., methane-acclimated *Geotoga* spp., methane-acclimated *Garciella* spp., humic acids, and a combination of any two or more thereof.

According to aspects of the present invention, wherein the methane-acclimated sludge isolate component is chosen from methane-acclimated *Paracoccus* spp.

According to aspects of the present invention, wherein the methane-acclimated sludge isolate component is a humic acid.

According to preferred aspects of the present invention, a selection marker is encoded by the recombinant expression cassette which expresses a resistance gene to select for cells containing the plasmid. According to preferred aspects of the present invention, the recombinant expression cassette which expresses a puromycin resistance gene to select for cells containing the plasmid. According to preferred aspects of the present invention, the recombinant expression cassette which expresses a puromycin resistance gene to select for cells containing the plasmid and puromycin is included in the anode chamber fluid (inoculation medium, anolyte) in order to maintain the presence of the heterologous nucleic acid sequence encoding a methyl-coenzyme M reductase derived from an anaerobic methane oxidizer in methanogens present in the anode chamber.

According to preferred aspects of the present invention, puromycin is included in the anode chamber in amounts in the range of about 0.5 micrograms/milliliter to about 10 micrograms/milliliter, such as about 0.75 micrograms/milliliter to about 7.5 micrograms/milliliter, such as about 1 microgram/milliliter to about 5 micrograms/milliliter, such as about 2 micrograms/milliliter.

DETAILED DESCRIPTION OF THE INVENTION

Figure 1:
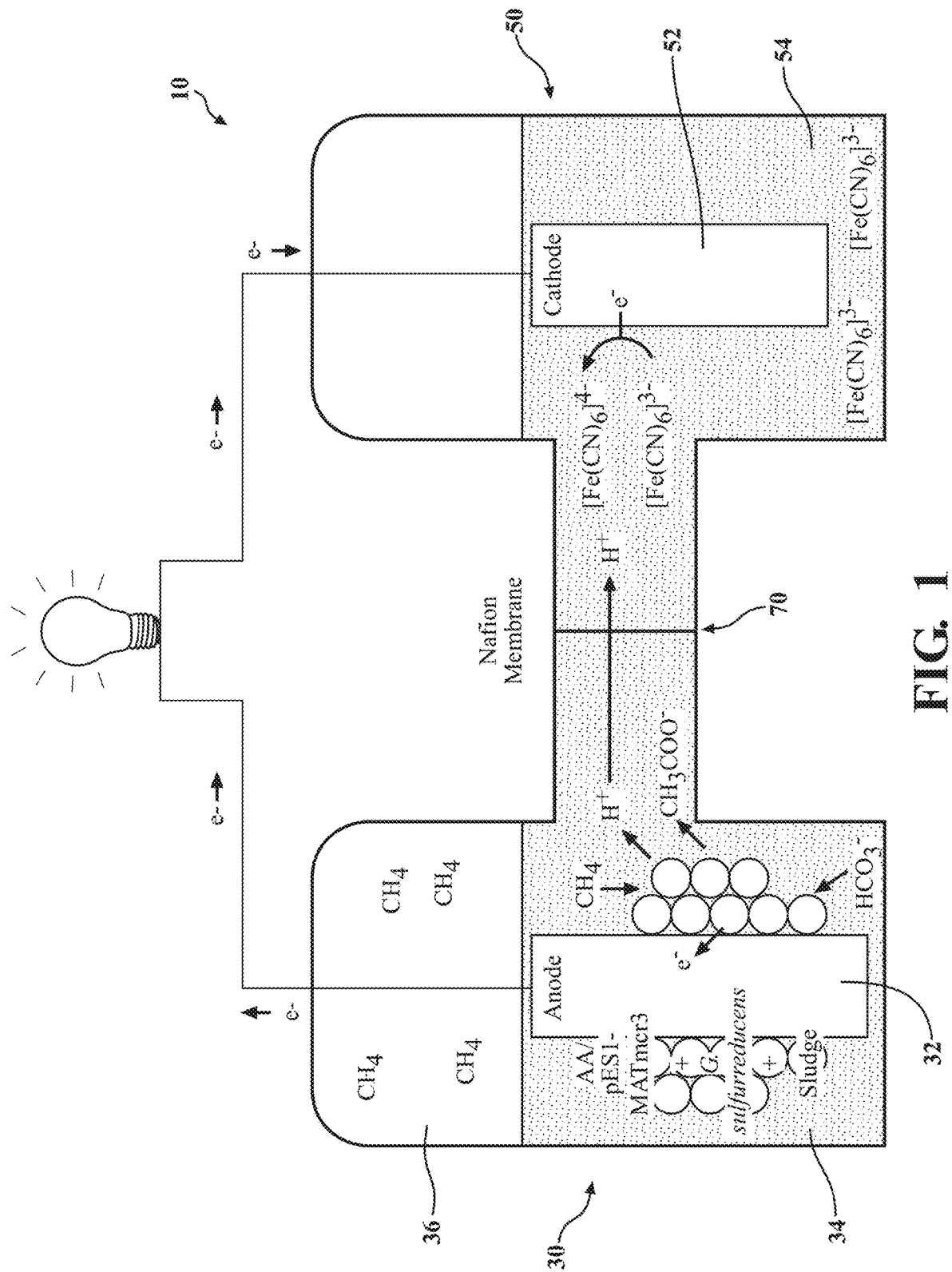
FIG. 1 is a schematic illustration of a microbial fuel cell (hereinafter, "MFC") having a dual-chamber setup in which air-adapted *M. acetivorans* containing pES1-MATmcr3 (i.e., AA/pES1-MATmcr3), *G. sulfurreducens*, and sludge, transfer electrons (i.e., e⁻) extracellulary on an anode (i.e., Anode) in an anode chamber from which the electrons migrate to a cathode (i.e., Cathode) in a cathode chamber to create an electrical current with a proton-conducting membrane (i.e., Nafion membrane) between the anode and the cathode. The anode chamber includes a methane (i.e., $CH_4$) headspace and the cathode chamber includes a ferricyanide solution (i.e., $[Fe(CN)_6]^{3-}$) as a catholyte.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, Pa., 2003; and Herdewijn, P. (Ed.), Oligonucleotide Synthesis: Methods and Applications, Methods in Molecular Biology, Humana Press, 2004.

The singular terms "a," "an," and "the" are not intended to be limiting and include plural referents unless explicitly stated otherwise or the context clearly indicates otherwise.

As used herein "promoter" includes reference to a region of DNA upstream from the start of transcription and involved in recognition and binding of RNA polymerase and other proteins to initiate transcription. A cell type specific promoter primarily drives expression in certain cell types. An inducible or repressible promoter is a promoter which is under environmental control. Examples of environmental conditions that may affect transcription by inducible promoters include anaerobic conditions or the presence of light. Cell type specific and inducible promoters are examples of the class of non-constitutive promoters. A constitutive promoter is a promoter which is active under most environmental conditions and in many cell types.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. As used herein, recombinant does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

According to preferred aspects of the present invention, a selection marker is encoded by the recombinant expression cassette which expresses a resistance gene to select for cells containing the plasmid. According to preferred aspects of the present invention, the recombinant expression cassette which expresses a puromycin resistance gene to select for cells containing the plasmid. According to preferred aspects of the present invention, the recombinant expression cassette which expresses a puromycin resistance gene to select for cells containing the plasmid and puromycin is included in the anode chamber fluid (inoculation medium, anolyte) in order to maintain the presence of the heterologous nucleic acid sequence encoding a methyl-coenzyme M reductase derived from an anaerobic methane oxidizer in methanogens present in the anode chamber. Puromycin is included in amounts in the range of about 0.5 micrograms/milliliter to about 10 micrograms/milliliter, such as about 0.75 micrograms/milliliter to about 7.5 micrograms/milliliter, such as about 1 microgram/milliliter to about 5 micrograms/milliliter, such as about 2 micrograms/milliliter.

Inoculation medium may further include reagents to maintain the recombinant acid constructs, such as, e.g., puromycin included in amounts in the range of about 0.5 micrograms/milliliter to about 10 micrograms/milliliter, such as about 0.75 micrograms/milliliter to about 7.5 micrograms/milliliter, such as about 1 microgram/milliliter to about 5 micrograms/milliliter, such as about 2 micrograms/milliliter.

Embodiments of the present disclosure are directed toward microbial consortia, microbial fuel cells, and methods for generating electrical current.

I. Microbial Consortia

In one or more embodiments, the disclosure discloses microbial consortia for generating electrical current.

In embodiments, the microbial consortia include: 1) an engineered methanogen that contains a heterologous nucleic acid sequence encoding a methyl-coenzyme M reductase derived from an anaerobic methane oxidizer, 2) an exoelectrogen microbe that produces electrically-conductive appendages, and 3) a sludge or sludge isolate component chosen from *Paracoccus* spp., *Geotoga* spp., *Geobacter* spp., *Methanosarcina* spp., *Garciella* spp., humic acids, or combination thereof.

The term "methanogen" refers to a microorganism that produces methane as a metabolic product under anaerobic conditions. Non-limiting examples of methanogens include *Methanosarcina acetivorans* (*M. acetivorans*), *M. barkeri*, *M. palustris*, *M. jannaschii*, *M. infernus*, *M. voltae*, *M. kandleri*, *M. fervidus*, and *M. marburgensis*.

The term "anaerobic methane oxidizer" refers to an anaerobic methanotrophic (ANME) organism which oxidizes methane in a metabolic process. Such ANME from which a methyl-coenzyme M reductase can be isolated for introduction into a methanogen are well-known and include those from phylogenetic clusters ANME-1, ANME-2, ANME-3 and ANME-4.

A methyl-coenzyme M reductase derived from an anaerobic methane oxidizer activates methane in methanotrophic archaea, Methyl-coenzyme M reductases derived from an anaerobic methane oxidizer include those derived from ANME organisms of phylogenetic clusters ANME-1, ANME-2, ANME-3 and ANME-4, such as those shown and described in Shima et al., Nature, 481:98-101 and supplementary information: doi:10.1038/nature10663. A methyl-coenzyme M reductase can be derived from an anaerobic methane oxidizer using standard techniques of molecular biology.

The term "sludge" as used herein refers to a semi-solid slurry or suspension of an anaerobic digester with a methane headspace which can be removed from the anaerobic digester and stored under conditions for use in a microbial fuel cell according to aspects of the present invention. In embodiments, sludge is a semi-solid slurry or suspension isolated from wastewater and/or water treatment processes. In illustrative, non-limiting embodiments, the sludge described herein is sewage sludge isolated from wastewater treatment facilities. Sewage sludge may be produced as a by-product of wastewater treatment processes. Sludge includes microbes and storage conditions for the sludge are those compatible with maintaining a culture of anaerobic microbes, such as, for example, a "high salt" (HS) solution which may be supplemented by yeast extract and/or other factors, see for example Metcalf et al. (1996) *J. Bacteriol.* 178: 5797-5802. Sludge may include various components such as, but not limited to, *Paracoccus* spp., *Geotoga* spp., *Geobacter* spp., *Methanosarcina* spp., *Garciella* spp., and humic acids.

Optionally, sludge or a microbial component thereof is methane-acclimated. Methane-acclimation refers to a process of exposing a microbe to anaerobic culture conditions including the presence of methane, for example, to stimulate and select for metabolic processes utilizing methane.

In embodiments, the microbial consortia include: 1) an engineered *Methanosarcina acetivorans* that contains a heterologous nucleic acid sequence encoding methyl-coenzyme M reductase, 2) an exoelectrogen microbe that produces electrically-conductive appendages and/or one or more types of electron carrier, and 3) a methane-acclimated sludge isolate component chosen from *Paracoccus* spp., *Geotoga* spp., *Geobacter* spp., *Methanosarcina* spp., *Garciella* spp., humic acids, or combination thereof.

In embodiments, the microbial consortia include an engineered methanogen (such as *M. acetivorans*) that contains a heterologous nucleic acid sequence (e.g., mRNA or DNA) encoding methyl-coenzyme M reductase. In embodiments, the heterologous nucleic acid sequence is contained in a recombinant nucleic acid construct (e.g. a plasmid). The methanogen may be engineered to contain the heterologous nucleic acid sequence encoding methyl-coenzyme M reductase (or the recombinant nucleic acid construct containing the same) via transformation techniques known to those of ordinary skill in the art. Exemplary, non-limiting transformation techniques include virus-based gene delivery methods, lipid-based transfection methods, and/or electroporation. In illustrative, non-limiting embodiments, the methanogen may be engineered via transformation with a recombinant nucleic acid construct encoding the methyl-coenzyme M reductase, as described in Soo et al. (2016) *Microb. Cell Fact.* 15: 11 (hereinafter, "Soo et al.") and U.S. Pub. No. 2015/0147791. Soo et al. is incorporated herein by reference in its entirety. In embodiments, the engineered methanogen expresses a methyl-coenzyme M reductase derived from an anaerobic methane oxidizer, such as those derived from ANME organisms of phylogenetic clusters ANME-1, ANME-2, ANME-3 and ANME-4 e.g., from unculturable ANME in a microbial mat in the Black Sea.

In illustrative, non-limiting embodiments, the engineered methanogen that expresses non-native methyl-coenzyme M reductase consumes methane to produce oxidized intermediates (including, e.g., acetate). Such oxidized intermediates may be consumed by exoelectrogen microbes that produce electrically-conductive appendages and/or one or more types of electron carrier and/or by sludge, methane-acclimated sludge or methane-acclimated sludge isolate components, described in greater detail below. The engineered methanogen may also donate electrons to exoelectrogen microbes that produce electrically-conductive appendages and/or one or more types of electron carrier, and/or to sludge, methane-acclimated sludge and/or sludge isolate components, described in greater detail below.

Methyl-coenzyme M reductases derived from anaerobic methane oxidizers are known in the art to have three subunits: methyl-coenzyme M reductase alpha subunit; methyl-coenzyme M reductase, beta subunit and methyl-coenzyme M reductase, gamma subunit disclosed herein as characterized by SEQ ID NO: 1; SEQ ID NO: 2; and SEQ ID NO: 3, respectively.

The term "methyl-coenzyme M reductase derived from an anaerobic methane oxidizer" refers to a three subunit methyl-coenzyme M reductase protein which activates methane in methanotrophic archaea, including methyl-coenzyme M reductase alpha subunit disclosed herein as characterized by SEQ ID NO: 1, encoded by SEQ ID NO: 2; methyl-coenzyme M reductase, beta subunit disclosed herein as characterized by SEQ ID NO: 3, encoded by SEQ ID NO: 4; and methyl-coenzyme M reductase, gamma subunit disclosed herein as characterized by SEQ ID NO: 5, encoded by SEQ ID NO: 6; and variants thereof. The term "variant" used herein refers to a methyl-coenzyme M reductase derived from an anaerobic methane oxidizer and is a peptide or protein effective to activate methane in methanotrophic archaea and which includes an alteration, i.e. a substitution, insertion or deletion, of one or more amino acids compared to the full-length amino acid sequences of SEQ ID NO: 1; SEQ ID NO: 3; and SEQ ID NO: 5.

The term "variant" used herein refers to a methyl-coenzyme M reductase derived from an anaerobic methane oxidizer and refers to both naturally occurring variations of a given methyl-coenzyme M reductase derived from an anaerobic methane oxidizer and recombinantly prepared mutations, as well as to functional fragments of a methyl-coenzyme M reductase derived from an anaerobic methane oxidizer, wherein the variant is effective to activate methane in methanotrophic archaea.

A variant of methyl-coenzyme M reductase alpha subunit of SEQ ID NO: 1 has at least 80%, or at least 85%, 86%, 87%, 88%, 89%, 90%, 91%, 92%, 93%, 94%, 95%, 96%, 97%, 98%, 99%, or greater, amino acid sequence identity to full-length methyl-coenzyme M reductase alpha subunit of SEQ ID NO:1.

A variant of methyl-coenzyme M reductase beta subunit of SEQ ID NO: 3 has at least 80%, or at least 85%, 86%, 87%, 88%, 89%, 90%, 91%, 92%, 93%, 94%, 95%, 96%, 97%, 98%, 99%, or greater, amino acid sequence identity to full-length methyl-coenzyme M reductase alpha subunit of SEQ ID NO: 2.

A variant of methyl-coenzyme M reductase beta subunit of SEQ ID NO: 5 has at least 80%, or at least 85%, 86%, 87%, 88%, 89%, 90%, 91%, 92%, 93%, 94%, 95%, 96%, 97%, 98%, 99%, or greater, amino acid sequence identity to full-length methyl-coenzyme M reductase alpha subunit of SEQ ID NO: 3.

As will be readily apparent to one of skill in the art, due to the redundancy of the genetic code, more than one nucleic acid sequence encodes each of the three subunits of SEQ ID NO: 1; SEQ ID NO: 3; and SEQ ID NO: 5, respectively.

A variant of methyl-coenzyme M reductase alpha subunit of SEQ ID NO: 1 can be encoded by a nucleic acid sequence having substantial similarity to SEQ ID NO: 2. A nucleic acid sequence having substantial similarity to a nucleic acid sequence SEQ ID NO: 2, encoding a methyl-coenzyme M reductase alpha subunit has at least 70%, at least 75%, or at least 85%, 90%, 91%, 92%, 93%, 94%, 95%, 96%, 97%, 98%, 99%, or greater, nucleic acid sequence identity to SEQ ID NO: 2.

A variant of methyl-coenzyme M reductase beta subunit of SEQ ID NO: 3 can be encoded by a nucleic acid sequence having substantial similarity to SEQ ID NO: 4. A nucleic acid sequence having substantial similarity to a nucleic acid sequence SEQ ID NO: 4, encoding a methyl-coenzyme M reductase alpha subunit has at least 70%, at least 75%, or at least 85%, 90%, 91%, 92%, 93%, 94%, 95%, 96%, 97%, 98%, 99%, or greater, nucleic acid sequence identity to SEQ ID NO: 4.

A variant of methyl-coenzyme M reductase gamma subunit of SEQ ID NO: 5 can be encoded by a nucleic acid sequence having substantial similarity to SEQ ID NO: 6. A nucleic acid sequence having substantial similarity to a nucleic acid sequence SEQ ID NO: 6, encoding a methyl-coenzyme M reductase alpha subunit has at least 70%, at least 75%, or at least 85%, 90%, 91%, 92%, 93%, 94%, 95%, 96%, 97%, 98%, 99%, or greater, nucleic acid sequence identity to SEQ ID NO: 6.

In embodiments of the present invention, a substantially similar nucleic acid sequence is characterized as having a complementary nucleic acid sequence capable of hybridizing to a nucleic acid sequence encoding a methyl-coenzyme M reductase subunit or a functional fragment thereof under high stringency hybridization conditions.

The term "nucleic acid" as used herein refers to RNA or DNA molecules having more than one nucleotide in any form including single-stranded, double-stranded, oligonucleotide or polynucleotide. The term "nucleotide sequence" is used to refer to the ordering of nucleotides in an oligonucleotide or polynucleotide in a single-stranded form of nucleic acid.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone. Under highly stringent conditions SEQ ID NOs. 2, 4, and 6 will each hybridize to the complement of substantially identical targets and not to unrelated sequences.

Mutations can be introduced using standard molecular biology techniques, such as site-directed mutagenesis and PCR-mediated mutagenesis. One of skill in the art will recognize that one or more amino acid mutations can be introduced without altering the functional properties of a methyl-coenzyme M reductase derived from an anaerobic methane oxidizer. For example, one or more amino acid substitutions, additions, or deletions can be made without altering the functional properties of a reference methyl-coenzyme M reductase derived from an anaerobic methane oxidizer, such as the a methyl-coenzyme M reductase derived from an anaerobic methane oxidizer characterized by subunits of SEQ ID NO: 1, SEQ ID NO: 3 and SEQ ID NO: 5.

Conservative amino acid substitutions can be made in a methyl-coenzyme M reductase derived from an anaerobic methane oxidizer to produce a variant. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, histidine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

Variants according to aspects of the present invention can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

As noted above, embodiments of methods, consortia and fuel cells of the present invention include methyl-coenzyme M reductase derived from an anaerobic methane oxidizer proteins having at least 85%, 86%, 87%, 88%, 89%, 90%, 91%, 92%, 93%, 94%, 95%, 96%, 97%, 98% or 99% amino acid sequence identity to SEQ ID NO: 1, SEQ ID NO:3 or SEQ ID NO:5.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions ×100%). In one embodiment, the two sequences are the same length. Alternatively, the two sequences may be different lengths, such as 1, 2, 3, 4, 5, 6, 7, 8, 9 or 10 amino acids different in length. The additions or deletions may be at the N-terminus, C-terminus, internally or a mixture of any thereof.

The determination of percent identity between two sequences can also be accomplished using a mathematical algorithm. A preferred, non-limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules. When utilizing BLAST, Gapped BLAST, and PSI Blast programs, the default parameters of the respective programs (e.g., of XBLAST and NBLAST) are used. Another preferred, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

In some embodiments, a methanogen which is engineered as described above is a wild-type strain (e.g., *M. acetivorans* C2A), as are known to those of ordinary skill in the art. In other embodiments, a methanogen which is engineered as described above is an air-adapted strain (e.g., *M. acetivorans* AA), as are known to those of ordinary skill in the art. Air-adapted strains of a methanogen may be generated as described in Jasso-Chavez et al. (2015) *PLoS ONE* 10 (hereinafter, "Jasso-Chavez et al."). In illustrative, non-limiting embodiments, a methanogen is adapted to small pulses of oxygen thereby generating an air-adapted strain.

In some embodiments, *M. acetivorans* which is engineered as described above is a wild-type strain (e.g., *M. acetivorans* C2A), as are known to those of ordinary skill in the art. In other embodiments, *M. acetivorans* which is engineered as described above is an air-adapted strain (e.g., *M. acetivorans* AA), as are known to those of ordinary skill in the art. Air-adapted strains of *M. acetivorans* may be generated as described in Jasso-Chavez et al. (2015) *PLoS ONE* 10 (hereinafter, "lasso-Chavez et al."). In illustrative, non-limiting embodiments, *M. acetivorans* are adapted to small pulses of oxygen thereby generating an air-adapted strain.

In embodiments, the microbial consortia include an exoelectrogen microbe that produces electrically-conductive appendages (e.g., pili or extensions of an outer membrane containing cytochromes) and/or one or more types of electron carrier.

Electron carriers produced by exoelectrogens include, but are not limited to, FMN, FAD, and riboflavin.

Examples of exoelectrogen microbes that produce electrically-conductive appendages and/or one or more types of electron carrier are known to those of ordinary skill in the art. In embodiments, the exoelectrogen microbes may be chosen from *Geobacter* spp., *Shewanella* spp., or combination thereof. In embodiments, the exoelectrogen microbe that produces electrically-conductive appendages and/or one or more types of electron carrier is chosen from *Geobacter* spp. The *Geobacter* spp. may be chosen from *Geobacter anodireducens*, *Geobacter argillaceus*, *Geobacter bemidjiensis*, *Geobacter bremensis*, *Geobacter chapellei*, *Geobacter daltonii*, *Geobacter grbiciae*, *Geobacter hydrogenophilus*, *Geobacter lovley*, *Geobacter luticola*, *Geobacter metallireducens*, *Geobacter pelophilus*, *Geobacter pickeringii*, *Geobacter psychrophilus*, *Geobacter soli*, *Geobacter sulfurreducens*, *Geobacter thiogenes*, *Geobacter toluenoxydans*, *Geobacter uraniireducens*, or a combination of any two or more thereof. In illustrative-non-limiting embodiments, the *Geobacter* spp. are chosen from *Geobacter metallireducens*, *Geobacter sulfurreducens*, or combination thereof. In additional illustrative, non-limiting embodiments, the exoelectrogen microbe that produces electrically-conductive appendages and/or one or more types of electron carrier is *Geobacter sulfurreducens*. In further illustrative, non-limiting embodiments, the *G. sulfurreducens* is a wild-type strain (e.g., *M. acetivorans* PCA). In additional illustrative, non-limiting embodiments, the exoelectrogen microbe that produces electrically-conductive appendages and/or one or more types of electron carrier is *Geobacter metallireducens*.

In embodiments, the exoelectrogen microbe that produces electrically-conductive appendages and/or one or more types of electron carrier is chosen from *Shewanella* spp. In embodiments, the *Shewanella* spp. are chosen from *Shewanella abyssi*, *Shewanella aestuarii*, *Shewanella algae*, *Shewanella algidipiscicola*, *Shewanella amazonensis*, *Shewanella aquimarina*, *Shewanella arctica*, *Shewanella atlantica*, *Shewanella baltica*, *Shewanella basaltis*, *Shewanella benthica*, *Shewanella canadensis*, *Shewanella chilikensis*, *Shewanella colwelliana*, *Shewanella corallii*, *Shewanella decolorationis*, *Shewanella denitrificans*, *Shewanella dokdonensis*, *Shewanella donghaensis*, *Shewanella fidelis*, *Shewanella fodinae*, *Shewanella frigidmarina*, *Shewanella gaetbuli*, *Shewanella gelidimarina*, *Shewanella glacialipiscicola*, *Shewanella hafniensis*, *Shewanella halifaxensis*, *Shewanella halitois*, *Shewanella hanedai*, *Shewanella indica*, *Shewanella irciniae*, *Shewanella japonica*, *Shewanella kaireitica*, *Shewanella litorisediminis*, *Shewanella livingstonensis*, *Shewanella loihica*, *Shewanella mangrovi*, *Shewanella marina*, *Shewanella marinintestina*, *Shewanella marisflavi*, *Shewanella morhuae*, *Shewanella olleyana*, *Shewanella oneidensis*, *Shewanella piezotolerans*, *Shewanella pacifica*, *Shewanella pealeana*, *Shewanella piezotolerans*, *Shewanella penumatophori*, *Shewanella putrefaciens*, *Shewanella sairae*, *Shewanella schegeliana*, *Shewanella sediminis*, *Shewanella seohaensis*, *Shewanella spongiae*, *Shewanella surugensis*, *Shewanella upenei*, *Shewanella vesiculosa*, *Shewanella violacea*, *Shewanella waksmanii*, *Shewanella woodyi*, *Shewanella xiamenensis*, or combination of two or three thereof. In illustrative, non-limiting embodiments, the *Shewanella* spp. are chosen from *Shewanella putrefaciens* IR-1, *Shewanella oneidensis* DSP10, or a combination of any two or more thereof.

In illustrative, non-limiting embodiments, the exoelectrogen microbe that produces electrically-conductive appendages and/or one or more types of electron carrier may be used to rapidly transfer electrons by increasing electron transfer surface area to electron shuttle molecules. Additionally, the exoelectrogen microbe that produces electrically-conductive appendages and/or one or more types of electron carrier may consume oxidized intermediates produced by an engineered methanogen, as described above.

Optionally, one or more enhancers of efficiency of electron transfer to the anode may be included in the fluid in the anode chamber. According to particular embodiments, cytochrome C is included in the fluid in the anode chamber. As is well-known, cytochrome C is a protein which is highly conserved across a wide range of species, including plants, mammals and microorganisms. Cytochrome C for inclusion in the fluid in the anode chamber can be isolated according to known methods or purchased commercially. Cytochrome C is included in the fluid in the anode chamber to achieve a concentration in the range of about 200 nM-200 µM, such as 250 nM-100 µM. In particular aspects, cytochrome C is included in the fluid in the anode chamber to achieve a concentration in the range of about 500 nM-50 µM, such as 10 µM-30 µM. In further aspects, cytochrome C is included in the fluid in the anode chamber to achieve a concentration of about 20 µM.

Optionally, exoelectrogen microbes that produce electrically-conductive appendages and/or one or more types of electron carrier are genetically modified to enhance electron transfer to the anode, such as by increasing conductivity of pili produced by the organisms. In a non-limiting example, exoelectrogen microbes that produce electrically-conductive appendages and/or one or more types of electron carrier can be genetically modified to express the PilA protein of *Geobacter metallireducens* to enhance electron transfer to the anode and increase current production in a microbial fuel cell of the present disclosure.

In embodiments, the microbial consortia include a methane-acclimated sludge isolate component.

In embodiments, a sludge isolate component may be chosen from *Paracoccus* spp., *Geotoga* spp., *Garciella* spp., humic acids, or combination thereof. In embodiments, the sludge isolate component is chosen from *Paracoccus* spp. In embodiments, *Paracoccus* sp. are chosen from *Paracoccus alcaliphilus, Paracoccus alkenifer, Paracoccus aminophilus, Paracoccus aminovorans, Paracoccus bengalensis, Paracoccus carotinifaciens, Paracoccus denitrificans, Paracoccus ferrooxidans, Paracoccus haeundaensis, Paracoccus halotolerans, Paracoccus homiensis, Paracoccus kawasakiensis, Paracoccus kocurii, Paracoccus kondratievae, Paracoccus koreensis, Paracoccus marcusii, Paracoccus methylutens, Paracoccus pantotrophus, Paracoccus seriniphilus, Paracoccus solventivorans, Paracoccus* sp. 1017. *Paracoccus* sp. 1165b, *Paracoccus* sp. 12-A. *Paracoccus* sp. 164, *Paracoccus* sp. 18, *Paracoccus* sp. 18III/A01/069, *Paracoccus* sp. 18III/A01/070, *Paracoccus* sp. 1MN-3, *Paracoccus* sp. 2-2, *Paracoccus* sp. 33, *Paracoccus* sp. 3PB-1, *Paracoccus* sp. 42NP24, *Paracoccus* sp. 4FB8, *Paracoccus* sp. 5-1, *Paracoccus* sp. '5.5 MW-13', *Paracoccus* sp. 71X/A01/160, *Paracoccus* sp. 88/2-4, *Paracoccus* sp. A10, *Paracoccus* sp. A510, *Paracoccus* sp. AG06, *Paracoccus* sp. AI-14, *Paracoccus* sp. AI-21, *Paracoccus* sp. ARCTIC-P17, *Paracoccus* sp. AS-37, *Paracoccus* sp. B-1012, *Paracoccus* sp. B-1017, *Paracoccus* sp. B-1018, *Paracoccus* sp. B-1020, *Paracoccus* sp. B-1082, *Paracoccus* sp. B-1111, *Paracoccus* sp. BBTR62, *Paracoccus* sp. BC-SBS2A-4, *Paracoccus* sp. BOG6, *Paracoccus* sp. BSs20193, *Paracoccus* sp. 'CJSPY1 (P-I)', *Paracoccus* sp. D39p6, *Paracoccus* sp. D49-PB-H05, *Paracoccus* sp. DHHS10, *Paracoccus* sp. DM, *Paracoccus* sp. DMF, *Paracoccus* sp. DS2, *Paracoccus* sp. DSG13, *Paracoccus* sp. dtb77, *Paracoccus* sp. DY16, *Paracoccus* sp. DY17, *Paracoccus* sp. E33, *Paracoccus* sp. E45, *Paracoccus* sp. E46, *Paracoccus* sp. E71, *Paracoccus* sp. EM0091, *Paracoccus* sp. FTY1, *Paracoccus* sp. G200V, *Paracoccus* sp. GWS-BW-H72M, *Paracoccus* sp. GWS-SE-H131, *Paracoccus* sp. HN-182, *Paracoccus* sp. HPB-50, *Paracoccus* sp. HPC19, *Paracoccus* sp. HPC5, *Paracoccus* sp. HPC719, *Paracoccus* sp. HZ04, *Paracoccus* sp. HZBN13, *Paracoccus* sp. HZBN53, *Paracoccus* sp. J364, *Paracoccus* sp. J52, *Paracoccus* sp. J987, *Paracoccus* sp. JL1080, *Paracoccus* sp. JL1105, *Paracoccus* sp. JL1148, *Paracoccus* sp. JL-64, *Paracoccus* sp. JL-65, *Paracoccus* sp. JL-S11, *Paracoccus* sp. K0-28L-028, *Paracoccus* sp. K4-28-038, *Paracoccus* sp. K4-28L-025, *Paracoccus* sp. K8-4L-015, *Paracoccus* sp. KIN136, *Paracoccus* sp. KL 1, *Paracoccus* sp. KS1, *Paracoccus* sp. KS2, *Paracoccus* sp. L7K5, *Paracoccus* sp. L, *Paracoccus* sp. LW36, *Paracoccus* sp. LZX21, *Paracoccus* sp. M039, *Paracoccus* sp. M-1, *Paracoccus* sp. m7-52, *Paracoccus* sp. m8-11, *Paracoccus* sp. m9-47, *Paracoccus* sp. 'Mali 27', *Paracoccus* sp. MBIC1145, *Paracoccus* sp. MBIC3024, *Paracoccus* sp. MBIC4017, *Paracoccus* sp. MBIC4018, *Paracoccus* sp. MBIC4019, *Paracoccus* sp. MBIC4020, *Paracoccus* sp. MBIC4036, *Paracoccus* sp. mdw-1, *Paracoccus* sp. MG33, *Paracoccus* sp. MN69, *Paracoccus* sp. MN70, *Paracoccus* sp. MN71, *Paracoccus* sp. MN72, *Paracoccus* sp. MSCB-2, *Paracoccus* sp. N81106, *Paracoccus* sp. NB152, *Paracoccus* sp. NPO-JL-65, *Paracoccus* sp. O118, *Paracoccus* sp. Ophe1, *Paracoccus* sp. P11, *Paracoccus* sp. PB33, *Paracoccus* sp. PC1, *Paracoccus* sp. PCLb-29, *Paracoccus* sp. PCLb-30, *Paracoccus* sp. PM07, *Paracoccus* sp. PRLIST3, *Paracoccus* sp. PRLISY02. *Paracoccus* sp. QD5-2-1, *Paracoccus* sp. R114, *Paracoccus* sp. R-24292, *Paracoccus* sp. R-24342, *Paracoccus* sp. R-24615 *Paracoccus* sp. R-24616, *Paracoccus* sp. R-24617, *Paracoccus* sp. R-24621, *Paracoccus* sp. R-24623, *Paracoccus* sp. R-24649, *Paracoccus* sp. R-24650, *Paracoccus* sp. R-24652, *Paracoccus* sp. R-24665, *Paracoccus* sp. R-25049, *Paracoccus* sp. R-25058, *Paracoccus* sp. R-25059, *Paracoccus* sp. R-26466, *Paracoccus* sp. R-26819, *Paracoccus* sp. R-26822, *Paracoccus* sp. R-26823, *Paracoccus* sp. R-26824, *Paracoccus* sp. R-26839, *Paracoccus* sp. R-26841, *Paracoccus* sp. R-26844, *Paracoccus* sp. R-26888, *Paracoccus* sp. R-26893, *Paracoccus* sp. R-26896, *Paracoccus* sp. R-26897, *Paracoccus* sp. R-26899, *Paracoccus* sp. R-26901, *Paracoccus* sp. R-26902, *Paracoccus* sp. R-27041, *Paracoccus* sp. R-27043, *Paracoccus* sp. R-27047, *Paracoccus* sp. R-27049, *Paracoccus* sp. R-28237, *Paracoccus* sp. R-28238, *Paracoccus* sp. R-28239, *Paracoccus* sp. R-28241, *Paracoccus* sp. R-28242, *Paracoccus* sp. R-28243, *Paracoccus* sp. R-28244, *Paracoccus* sp. R-28245, *Paracoccus* sp. R-28294, *Paracoccus* sp. R-28409, *Paracoccus* sp. R-28414, *Paracoccus* sp. SA5, *Paracoccus* sp. SAM-029, *Paracoccus* sp. SBR3, *Paracoccus* sp. SBRD1, *Paracoccus* sp. SBRD2, *Paracoccus* sp. SW1.6, *Paracoccus* sp. T2-28, *Paracoccus* sp. T231, *Paracoccus* sp. T5-20, *Paracoccus* sp. T6-10, *Paracoccus* sp. TDMA-10, *Paracoccus* sp. TDMA-8, *Paracoccus* sp. Tibet-S9a3, *Paracoccus* sp. TJD650, *Paracoccus* sp. TJD708, *Paracoccus* sp. TJD721, *Paracoccus* sp. TJD782, *Paracoccus* sp. TJD793, *Paracoccus* sp. TRP, *Paracoccus* sp. TUT1021, *Paracoccus* sp. WB1, *Paracoccus* sp. Y13, *Paracoccus* sp. YACS20, *Paracoccus* sp. YACS25, *Paracoccus* sp. zf-IIRlt10, *Paracoccus* sp. zf-IRht7, *Paracoccus* sp. ZY-2006h, *Paracoccus thiocyanatus, Paracoccus thiophilus, Paracoccus versutus, Paracoccus yeei, Paracoccus zeaxanthinifaciens*, subspecies *Paracoccus zeaxanthinifaciens* subsp. *Payriae*, uncultured *Paracoccus* PC1, uncultured *Paracoccus* PC2, uncultured *Paracoccus* PC3, uncultured *Paracoccus* sp., uncultured *Paracoccus* sp. FR062, marine bacterium 13733, or a combination of any two or more thereof.

In embodiments, the sludge isolate component is chosen from *Geotoga* spp. In embodiments, *Geotoga* spp. are chosen from *Geotoga petraea, Geotoga subterranea*, or combination thereof. In embodiments, the sludge isolate component is chosen from *Garciella* spp. In embodiments, the sludge isolate component is *Garciella nitratireducens*.

In embodiments, the sludge isolate component is humic acids. Humic acids are a component of humic substances found in soil, peat, coal, streams, lakes, and/or oceans. Humic acids are produced by the biodegradation of dead organic matter. As is known to those of ordinary skill in the art, humic acids are a complex mixture of many different acids containing carboxyl and phenolate groups; as such, humic acids may behave functionally as dibasic acids and/or tribasic acids. In embodiments, humic acids may function as electron shuttle molecules.

Humic acids can be included in the anode compartment in a liquid anolyte in an amount in the range of about 0.01% w/v to about 10% w/v, such as 0.025% w/v to about 5% w/v, such as 0.05% w/v to about 1% w/v.

Optionally, one or more types of electron carriers can be included in the anode compartment in a liquid anolyte in an amount in the range of about 0.1 mM to about 10 mM, such as 0.25 mM to about 5 mM, such as 0.5 mM to about 1 mM.

In embodiments, the sludge isolate components consume oxidized intermediates produced by an engineered methanogen, as described above.

In embodiments, the sludge isolate components are acclimated to methane, as described in greater detail below. In illustrative, non-limiting embodiments, sludge isolate components are acclimated to methane via inoculation into a medium (such as, e.g., hydrosulphite of sodium medium) under a methane headspace with varying concentrations of $FeSO_4$ or $FeCl_3$ for a first time frame (e.g., 56 days). Then, subcultures may be grown in a medium (such as, e.g., hydrosulphite of sodium medium) under a methane headspace with $FeSO_4$ or $FeCl_3$ for a second time frame (e.g., 176 days). Finally, subcultures may be grown in a medium (such as, e.g., hydrosulphite of sodium medium) with ferrihydrite, $FeCl_3$, $FeSO_4$, or $FeCl_3$ for a third time frame.

II. Microbial Fuel Cells for Generating Electrical Current

In embodiments, the disclosure discloses microbial fuel cells for generating electrical current. According to aspects of the present invention, a reaction chamber of microbial fuel cell is provided which includes an anode chamber and a cathode chamber. In embodiments, the microbial fuel cells include: an anode chamber including an anode, a first fluid, and methane, a cathode chamber in selective communication with the anode chamber, the cathode chamber including a cathode in electrical communication with the anode and a second fluid, and a cation exchange material, such as a cation exchange membrane, disposed between the anode chamber and the cathode chamber.

A channel is included defining a passage from the exterior of the reaction chamber to the interior in particular embodiments. More than one channel may be included to allow and/or regulate flow of materials into and out of the reaction chamber. For example, a channel may be included to allow for outflow of a gas generated at the cathode. Further, a channel may be included to allow for outflow of a gas generated at the anode.

In a particular embodiment of a continuous flow configuration, a channel may be included to allow flow of a substance into a reaction chamber and a separate channel may be used to allow outflow of a substance from the reaction chamber. More than one channel may be included for use in any inflow or outflow function.

A regulator device, such as a valve, may be included to further regulate flow of materials into and out of the reaction chamber. Further, a cap or seal is optionally used to close a channel. For example, where a fuel cell is operated remotely or as a single use device such that no additional materials are added, a cap or seal is optionally used to close a channel.

A pump may be provided for enhancing flow of liquid or gas into and/or out of a reaction chamber.

In embodiments, the first fluid includes a microbial consortium including an engineered methanogen that contains a heterologous nucleic acid sequence encoding a methyl-coenzyme M reductase derived from an anaerobic methane oxidizer, an exoelectrogen microbe that produces electrically-conductive appendages and/or one or more types of electron carrier, and sludge, methane-acclimated sludge, a sludge isolate component, a methane-acclimated sludge isolate component chosen from *Paracoccus* spp., *Geotoga* spp., *Geobacter* spp., *Methanosarcina* spp., *Garciella* spp., humic acids; or a combination of any two or more thereof.

In embodiments, the first fluid includes a microbial consortium including an engineered *M. acetivorans* that contains a heterologous nucleic acid sequence encoding a methyl-coenzyme M reductase derived from an anaerobic methane oxidizer, an exoelectrogen microbe that produces electrically-conductive appendages and/or one or more types of electron carrier, and sludge, methane-acclimated sludge, a sludge isolate component, a methane-acclimated sludge isolate component chosen from *Paracoccus* spp., *Geotoga* spp., *Geobacter* spp., *Methanosarcina* spp., *Garciella* spp., humic acids; or a combination of any two or more thereof.

A methanogen is included in an anode chamber in amounts in the range of about $10^8$ to $10^{10}$ cells/milliliter of anolyte (first fluid), although more or fewer cells/milliliter may be included. An exoelectrogen is included in an anode chamber in amounts in the range of about $10^8$ to $10^{10}$ cells/milliliter of anolyte (first fluid), although more or fewer cells/milliliter may be included. Sludge or a microbe sludge isolate component is included in an anode chamber in amounts in the range of about $10^8$ to $10^{10}$ cells/milliliter of anolyte (first fluid), although more or fewer cells/milliliter may be included.

Figure 2:
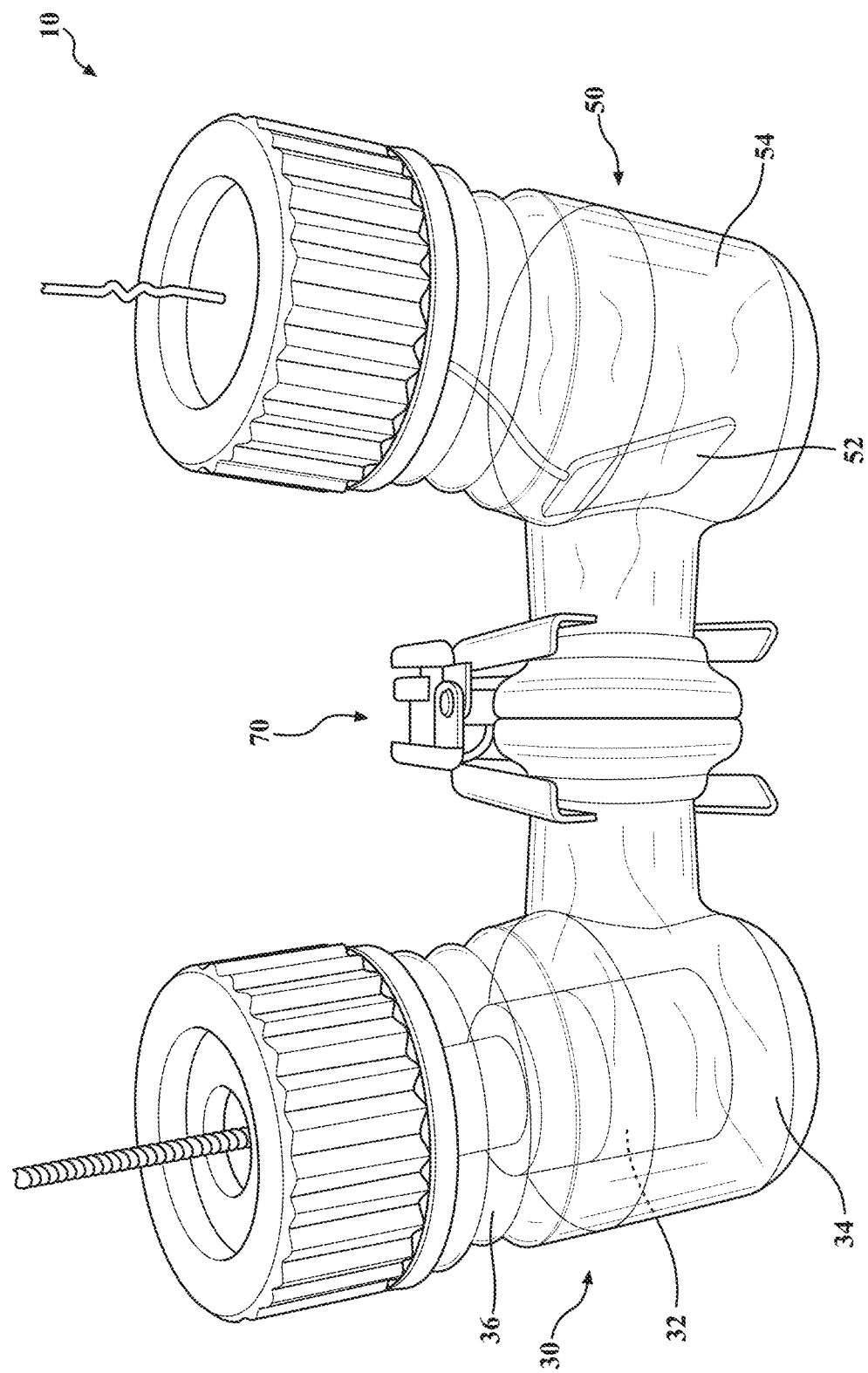
FIG. 2 is a picture of an MFC having a carbon fiber brush electrode as an anode in the anode chamber (Left) and a carbon cloth cathode in ferricyanide solution in the cathode chamber (Right)
Figure 3A:
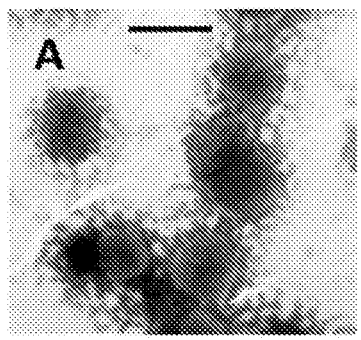
FIG. 3A is a transmission electron microscope image of anaerobic sludge consortium after two acclimations with methane as a carbon source and $FeSO_4$ (1 μM) as a terminal electron acceptor, with a 1 μM scale.
Figure 3B:
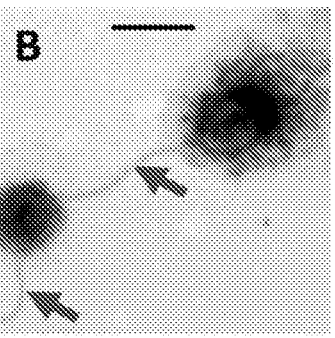
FIG. 3B is a transmission electron microscope image of anaerobic sludge consortium after two acclimations with methane as a carbon source and $FeSO_4$ (1 μM) as a terminal electron acceptor, with a 1 μM scale and arrows indicating pili.
Figure 3C:
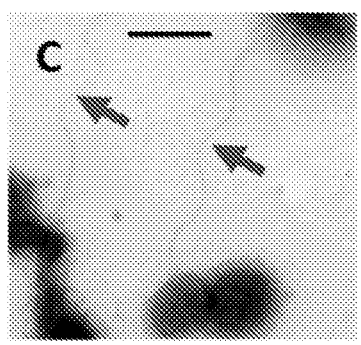
FIG. 3C is a transmission electron microscope image of anaerobic sludge consortium after two acclimations with methane as a carbon source and $FeSO_4$ (1 μM) as a terminal electron acceptor, with a 1 μM scale and arrows indicating pili.
Figure 3D:
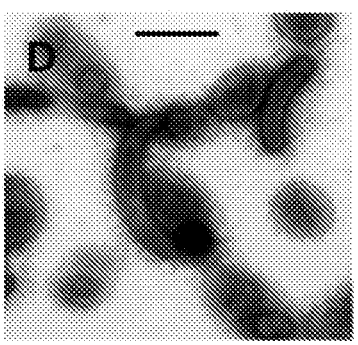
FIG. 3D is a transmission electron microscope image of anaerobic sludge consortium after two acclimations with methane as a carbon source and $FeCl_3$ (1 mM) as a terminal electron acceptor, with a 1 μM scale.
Figure 3E:
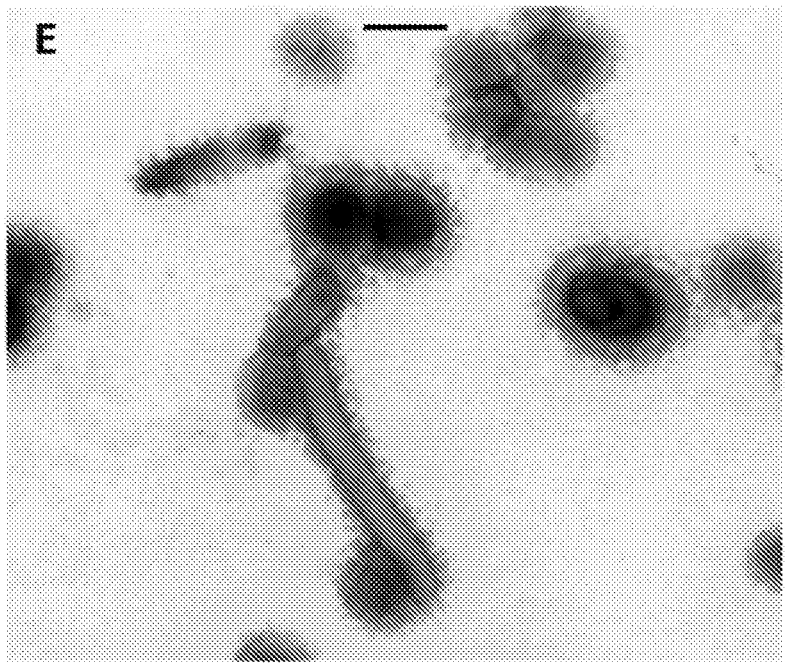
FIG. 3E is a transmission electron microscope image of anaerobic sludge consortium after two acclimations with methane as a carbon source and $FeCl_3$ (1 mM) as a terminal electron acceptor, with a 1 μM scale.

The microbial fuel cell may be made via methods known to those of ordinary skill in the art. In illustrative, non-limiting embodiments, the microbial fuel cell may be made as described in Oh et al. (2004) *Environ. Sci. Technol.* 38: 4900-4904 (hereinafter, "Oh et al."), with modifications. Referencing FIGS. 1-2, the microbial fuel cell (10) includes an anode chamber (30), a cathode chamber (50), and a cation exchange membrane (70).

The anode chamber (30) may include an anode (32), a first fluid (34), and methane (i.e., $CH_4$). The anode (32) may be made of any suitable material known to those of ordinary skill in the art. In embodiments, the anode (32) is made of a carbon fiber material (e.g., a carbon brush electrode).

In embodiments, the first fluid (34) includes a microbial consortium, as described above. In embodiments, the microbial consortium may be included in a suitable inoculation medium known to those of ordinary skill in the art. In illustrative, non-limiting embodiments, suitable inoculation mediums are hydrosulphite of sodium medium, hydrosulphite of sodium medium with yeast extract, and/or methanol. In embodiments, the first fluid (34) and/or inoculation medium may further include reagents to maintain the recombinant acid constructs, such as, e.g., puromycin. In embodiments, the methane is included in a headspace (36) of the anode chamber (30).

The cathode chamber (50) may include a cathode (52) in electrical communication with the anode (32), and a second fluid (54). The cathode (52) may be made of any suitable material known to those of ordinary skill in the art. In embodiments, the cathode (52) is made of a carbon material, such as, e.g., carbon cloth.

The cathode (52) may be in electrical communication with the anode (32) such that it is electrically connected thereto, such as, e.g., through wires, such that electrical signals may be exchanged therebetween. In embodiments, the second fluid (54) includes a suitable catholyte known to those of ordinary skill in the art. In illustrative, non-limiting embodiments, a suitable catholyte solution includes ferricyanide, sodium phosphate, ammonium chloride, and potassium chloride.

Anodes and cathodes included in a system according to the present invention are electrically conductive. Exemplary conductive electrode materials include, but are not limited to, carbon paper, carbon cloth, carbon fiber, carbon felt, carbon wool, carbon foam, carbon mesh, activated carbon, graphite, porous graphite, graphite powder, graphite granules, graphite fiber, a conductive polymer, a conductive metal, and combinations of any of these.

An anode and cathode included in a microbial fuel cell according to aspects of the present invention may have any of various shapes and dimensions and are positioned in various ways in relation to each other. More than one anode can be included in an inventive system. More than one cathode can be included in an inventive system.

A cation exchange material included in a microbial fuel cell according to aspects of the present invention is permeable to one or more selected cations. According to embodiments of the present invention, the cation exchange material is in the form of a cation exchange membrane. The cation exchange membrane may be made of any suitable material known to those of ordinary skill in the art. Cation exchange materials include, but are not limited to, ion-functionalized polymers exemplified by perfluorinated sulfonic acid polymers such as tetrafluoroethylene and perfluorovinylether sulfonic acid copolymers, and derivatives thereof; sulfonate-functionalized poly(phenylsulfone); and sulfonate-functionalized divinylbenzene cross-linked poly(styrene). Specific examples include NAFION, such as NAFION 117, and derivatives produced by E.I. DuPont de Nemours & Co., Wilmington, Del. Cation exchange materials include, for example, CMI cation exchange membranes made by Membranes International, Inc. New Jersey, USA. Also suitable are other varieties of sulfonated copolymers, such as sulfonated poly(sulfone)s, sulfonated poly(phenylene)s, and sulfonated poly(imides)s, and variations thereof.

In embodiments, the cation exchange membrane (70) is a proton exchange membrane. The cation exchange membrane (70) is disposed between the anode chamber (30) and the cathode chamber (50) to complete an electrical circuit by allowing excess positive charge in the anode chamber (30) to migrate to the cathode chamber (50). In this way, the anode chamber (30) and the cathode chamber (50) are in selective communication.

In embodiments, the microbial fuel cell (10) is operated anaerobically.

III. Methods for Generating Electrical Current

In embodiments, the disclosure discloses methods for generating electrical current. In embodiments, the methods include providing a microbial consortium to an anode chamber (30) of a microbial fuel cell (10). The microbial consortium may include an engineered methanogen that contains a heterologous nucleic acid sequence encoding a methyl-coenzyme M reductase derived from an anaerobic methane oxidizer, an exoelectrogen microbe that produces electrically-conductive appendages and/or one or more types of electron carrier, and sludge, methane-acclimated sludge, a sludge isolate component, a methane-acclimated sludge isolate component chosen from *Paracoccus* spp., *Geotoga* spp., *Geobacter* spp., *Methanosarcina* spp., *Garciella* spp., humic acids; or a combination of any two or more thereof. The microbial fuel cell (10) may include an anode chamber (30) comprising an anode (32) and methane, a cathode chamber (50) in selective communication with the anode chamber (30), the cathode chamber including a cathode (52) in electrical communication with the anode (32) and a catholyte (54), and a cation exchange membrane (70) disposed between the anode chamber (30) and the cathode chamber (50), wherein the microbial fuel cell (10) generates electrical current anaerobically.

The microbial consortium may be as described above. In embodiments, the microbial consortium is included in a suitable inoculation medium as described above. Similarly, the microbial fuel cell (10) may be as described above.

The microbial consortium may be provided to the anode chamber (30) of the microbial fuel cell (10) via suitable methods known to those of ordinary skill in the art. In illustrative, non-limiting embodiments, the microbial consortium is provided to the anode chamber (30) via inoculation. In some embodiments, the microbial consortium is provided to the anode chamber (30) in a single inoculation, such as, e.g., a single injection. In alternative embodiments, the microbial consortium is provided to the anode chamber (30) in a series of inoculations, such as, e.g., via separate injections for the methanogen that contains a heterologous nucleic acid sequence encoding a methyl-coenzyme M reductase derived from an anaerobic methane oxidizer, an exoelectrogen microbe that produces electrically-conductive appendages and/or one or more types of electron carrier, and sludge, methane-acclimated sludge, a sludge isolate component, a methane-acclimated sludge isolate component chosen from *Paracoccus* spp., *Geotoga* spp., *Geobacter* spp., *Methanosarcina* spp., *Garciella* spp., humic acids; or a combination of any two or more thereof. In embodiments where the microbial consortium is provided to the anode chamber (30) in a series of inoculations, the engineered methanogen that contains a heterologous nucleic acid sequence encoding a methyl-coenzyme M reductase derived from an anaerobic methane oxidizer, an exoelectrogen microbe that produces electrically-conductive appendages and/or one or more types of electron carrier, and sludge, methane-acclimated sludge, a sludge isolate component, a methane-acclimated sludge isolate component chosen from *Paracoccus* spp., *Geotoga* spp., *Geobacter* spp., *Methanosarcina* spp., *Garciella* spp., humic acids; or a combination of any two or more thereof may be provided to the anode chamber (30) at different time points. Additionally, in embodiments where the engineered methanogen that contains a heterologous nucleic acid sequence encoding a methyl-coenzyme M reductase derived from an anaerobic methane oxidizer, an exoelectrogen microbe that produces electrically-conductive appendages and/or one or more types of electron carrier, and sludge, methane-acclimated sludge, a sludge isolate component, a methane-acclimated sludge isolate component chosen from *Paracoccus* spp., *Geotoga* spp., *Geobacter* spp., *Methanosarcina* spp., *Garciella* spp., humic acids; or a combination of any two or more thereof are provided to the anode chamber (30) at different time points, the engineered methanogen that contains a heterologous nucleic acid sequence encoding a methyl-coenzyme M reductase derived from an anaerobic methane oxidizer, an exoelectrogen microbe that produces electrically-conductive appendages and/or one or more types of electron carrier, and sludge, methane-acclimated sludge, a sludge isolate component, a methane-acclimated sludge isolate component chosen from *Paracoccus* spp., *Geotoga* spp., *Geobacter* spp., *Methanosarcina* spp., *Garciella* spp., humic acids; or a combination of any two or more thereof may be provided in any order. In illustrative, non-limiting embodiments, the sludge, methane-acclimated sludge, a sludge isolate component, a methane-acclimated sludge isolate component chosen from *Paracoccus* spp., *Geotoga* spp., *Geobacter* spp., *Methanosarcina* spp., *Garciella* spp., humic acids; or a combination of any two or more thereof is provided to the anode chamber (30) last. In further illustrative, non-limiting embodiments, the sludge, methane-acclimated sludge, a sludge isolate component, a methane-acclimated sludge isolate component chosen from *Paracoccus* spp., *Geotoga* spp., *Geobacter* spp., *Methanosarcina* spp., *Garciella* spp., humic acids; or a combination of any two or more thereof is provided to the anode chamber (30) once the voltage of the microbial fuel cell (10) has decreased below a threshold value, such as, e.g., 150 mV.

The methods for generating electrical current described herein are anaerobic.

EXAMPLES

The following non-limiting examples illustrate the present disclosure. These examples are provided for illustrative purposes and are not considered limitations on the scope of inventive compositions and methods.

Example 1

Engineering *Methanosarcina acetivorans* to Produce Methyl-Coenzyme Reductase Materials and Methods. *M. acetivorans* strains were engineered to produce methyl-coenzyme M reductase (i.e., Mcr) from an unculturable ANME population 1 (i.e., ANME-1), identified in Black Sea mats, as described in Soo et al. Soo et al. is incorporated herein by reference in its entirety. The *M. acetivorans* strains employed in this Example are set forth below in Table 1 (i.e., *M. acetivorans* AA and *M. acetivorans* C2A).

*M. acetivorans* AA (2 mL) and *M. acetivorans* C2A (2 mL) were grown anaerobically as pre-cultures at about 37° C. in an 80% $N_2$/19% $CO_2$/1% $H_2$ atmosphere with mild shaking in hydrosulphite of sodium (i.e., HS) medium (10 mL) or HS medium with yeast extract (i.e., HSYE; 10 mL; 2.5 g/L of yeast extract) with methanol (125 mM) as the carbon source, as described in Metcalf et al. (1996) *J. Bacteriol.* 178: 5797-5802, unless otherwise indicated. All 28-mL culture tubes (18×150 mm; Bellco Glass, Vineland, N.J.) were sealed by aluminum crimp seals. *M. acetivorans* AA and *M. acetivorans* C2A were grown to a turbidity at 600 nm of 0.2 to 0.5 and were centrifuged and resuspended into transformation buffer (1 mL; 850 mM sucrose and 80 mM sodium bicarbonate, pH 7.4).

The Pmat (i.e., empty pES1 plasmid) and pES1-MATmcr3 plasmids were synthesized as described in Soo et al. The plasmids employed in this Example are as set forth in Table 1. In general, the Pmat and pES1-MATmcr3 plasmids were transformed into *M. acetivorans* strains using the liposome-mediated transformation procedure described in Metcalf et al. (1997) *Proc. Natl. Acad. Sci. U.S.A.* 97: 2626-2631, with slight modifications. More specifically, the Pmat or pES1-MATmcr3 plasmids (4 µg) were each mixed with DOTAP (n-(1-(2,3-dioleoyloxy)propyl)-n,n,n-trimethylammonium methyl-sulfate) (15 to 25 µL; Sigma-Aldrich, St. Louis, Mo.) prepared in transformation buffer to a final reaction volume of 50 µL and incubated at 37° C. for at least 15 min to make DNA:liposome complexes. The *M. acetivorans* AA and *M. acetivorans* C2A cell resuspensions were each then mixed with the DNA:liposome complex and incubated at 37° C. for 4 h. The *M. acetivorans* AA and *M. acetivorans* C2A cells were each then inoculated into HS or HSYE medium (10 mL) with methanol (125 mM). After 48 h of incubation, the *M. acetivorans* AA and *M. acetivorans* C2A cultures (1 mL) was each added to selective HSYE medium (10 mL) with methanol (125 mM) and puromycin (about 2 µg/mL).

Results. The engineered *M. acetivorans* AA and *M. acetivorans* C2A transformed with pES1-MATmcr3 plasmids were capable of growing anaerobically on methane as a main carbon source, as described in Soo et al. Without being bound by the theory, it is believed that the engineered *M. acetivorans* AA and *M. acetivorans* C2A transformed with pES1-MATmcr3 plasmids are capable of passing electrons to external $Fe^{3+}$ (such as, e.g., in the form of $FeCl_3$) and converting methane to acetate, as described in Soo et al.

Example 2

Generating a Microbial Consortium Including Engineered *M. acetivorans*, *Geobacter sulfurreducens*, and Methane-Acclimated Sludge Microorganisms Materials and Methods—Microbial Strains and Cultivation Conditions. Engineered *M. acetivorans* AA and *M. acetivorans* C2A transformed with Pmat or pES1-MATmcr3 plasmids were produced as described in Example 1. The engineered *M. acetivorans* AA and *M. acetivorans* C2A were grown anaerobically as pre-cultures at 37° C. in an 80% $N_2$/19% $CO_2$/1% $H_2$ atmosphere with mild shaking in HS or HSYE medium (10 mL) with methanol (125 mM) as the carbon source, as described in Metcalf et al. (1996) *J. Bacteriol.* 178: 5797-5802, unless otherwise indicated. All 28-mL culture tubes (18×150 mm, Bellco Glass) were sealed

TABLE 1

| Strain | Description | Source |
| --- | --- | --- |
| *M. acetivorans* AA | air-adapted *M. acetivorans* | Jasso-Chavez et al. |
| *G. sulfurreducens* PCA | wildtype *G. sulfurreducens* | J. G. Ferry |
| *M. acetivorans* C2A | wildtype *M. acetivorans* | Sowers et al. (1984) *Appl. Environ. Microbiol.* 47: 971-978 |
| Plasmids (i.e., Recombinant Expression Cassettes) | | |
| pES1(i.e., Pmat) | $Amp^R$, $Pur^R$, R6K ori, C2A ori, $P_{mcr\_ANME-1}$ | Soo et al. (2016) *Microb. Cell Fact.* 15: 11 |
| pES1-MATmcr3 | $Amp^R$, $Pur^R$, R6K ori, C2A ori, $P_{mcr\_ANME-1}$::$mcr_{ANME-1}$ | Soo et al. (2016) *Microb. Cell Fact.* 15: 11 | by aluminum crimp seals. Pmat and pES1-MATmcr3 plasmids were maintained in the engineered *M. acetivorans* AA and *M. acetivorans* C2A with puromycin (2 µg/mL), and methane served to induce ANME Mcr production, as described in Soo et al.

Experiments for testing oxygen tolerant (about 5 days) consumption of methane for the engineered *M. acetivorans* AA with high cell-density inocula were performed as described in Soo et al., with the following modifications: the strain (2 mL) was pre-grown in HS medium (200 mL) with methanol (125 mM), and puromycin (2 µg/mL) when pES1-MATmcr3 plasmids were present, at 37° C. for 5 days (turbidity at 600 nm of ~1.0). Engineered *M. acetivorans* AA cells were collected by centrifugation (5,000 rpm for 20 min) and were washed three times with HS medium and puromycin alone to remove residual methanol. The final cell pellet was resuspended using HS medium (5 mL) supplemented with $FeCl_3$ (10 mM) and puromycin (2 µg/mL) to yield a density of $4 \times 10^{10}$ CFU/mL. After filling the headspace of each tube with methane, oxygen was added, where indicated, by replacing a portion of the headspace with air to a final concentration of 1% oxygen. The tubes were incubated at 37° C. with shaking at 250 rpm for 5 days. Methane was quantified by gas chromatography, and acetate was quantified by high-pressure liquid chromatography as described in Soo et al.

*G. sulfurreducens* was grown anaerobically in *Geobacter* basal medium, as described in Caccavo et al. (1994) *Appl. Environ. Microbiol.* 60: 3752-3759, with sodium acetate (10 mM) as an electron donor and sodium fumarate (40 mM) as an electron acceptor, as described in Rotaru et al. (2015) *Front. Microbiol.* 6: 744. The *G. sulfurreducens* strain employed in this Example is set forth above in Table 1 (i.e., *G. sulfurreducens* PCA).

Anaerobic sludge from treated wastewater was collected (10 mL) just above the sedimentation layer of an anaerobic digester (maintained at 35° C.) from the Office of Physical Plant at the Pennsylvania State University, then kept under a headspace of methane at room temperature. The anaerobic sludge was acclimated over 567 days to methane as the main carbon source via three successive culturing cycles in HS medium with various terminal electron acceptors (i.e., TEAs). Referencing Table 2 below, the sample was inoculated (1:100) into HS medium under a methane headspace (hereinafter, "HS-methane") with varying concentrations of 0.001 to 100 mM $FeSO_4$ or $FeCl_3$ as TEAs for 56 days (i.e., First round TEA in Table 2). Then, subcultures (1:100 inoculation) were made in HS-methane with $FeSO_4$ (0.001 mM) or $FeCl_3$ (1 mM) as TEAs respectively, for 176 days (i.e., Second round TEA in Table 2). Finally, the subcultures were grown (1:100 inoculation) in HS-methane with ferrihydrite (40 mM), $FeCl_3$ (1 mM), $FeSO_4$ (0.001 mM) as TEAs with or without about 5% $H_2$ in the headspace, or $FeCl_3$ (about 0.001 mM) (i.e., Third round TEA in Table 2). Incubation was conducted at 37° C.

TABLE 2

Sludge Cultures Acclimated to Methane

| Third Round Culture | First Round TEA | Second Round TEA | Third Round TEA |
|---|---|---|---|
| 1* | 1 mM $FeCl_3$ | 1 mM $FeCl_3$ | 1 mM $FeCl_3$ |
| 2* | 1 mM $FeCl_3$ | 1 mM $FeCl_3$ | 1 mM $FeCl_3$, headspace of 80% $CH_4$ 20% $CO_2$ |
| 3 | 1 mM $FeCl_3$ | 1 mM $FeCl_3$ | 0.001 mM $FeSO_4$ |
| 4 | 1 mM $FeCl_3$ | 1 mM $FeCl_3$ | 0.001 mM $FeCl_3$ |
| 5 | 0.001 mM $FeSO_4$ | 0.001 mM $FeSO_4$ | 40 mM ferrihydrite |
| 6 | 0.001 mM $FeSO_4$ | 0.001 mM $FeSO_4$ | 1 mM $FeCl_3$ |
| 7 | 0.001 mM $FeSO_4$ | 0.001 mM $FeSO_4$ | 0.001 mM $FeSO_4$, headspace of 95% $CH_4$ 5% $H_2$ |

*The Third Round Cultures 1 and 2 are the same culture (not different replicates) and all cell lines came from the same original sludge isolate.

Transmission electron microscope. Cell morphology of sludge cultures was examined via transmission electron microscope (i.e., TEM; FEI Tecnai G2 Spirit BioTwin, Hillsboro, Oreg.) using uranyl acetate-stained cells as described in Fischer et al. (2012) *Curr. Protoc. Microbiol.* Chapter 2: Unit 2B 2.

Results—Imaging. As shown in FIGS. 3A-3E, visualization of anaerobic sludge cultures via TEM revealed cells (including, e.g., rod-shaped and irregular cocci-shaped) attached to each other with pili and subcellular structures (i.e., having a diameter of less than 50 nm) to form biofilm networks. Thus, without being bound by the theory, the sludge culture consortia were believed to have potential for conducting electrons in MFCs.

Example 3

Generating MFCs Employing Microbial Consortium Including Engineered *M. acetivorans*, *Geobacter sulfurreducens*, and Sludge Microorganisms Materials and Methods Microbial Strains and Cultivation Conditions. Engineered *M. acetivorans* AA, engineered *M. acetivorans* C2A, *G. sulfurreducens* PCA, and methane-acclimated sludge microorganisms were produced as described in Examples 1 and 2.

MFC Generation. Referencing FIGS. 1-2, two-bottle MFC reactors (total volume of each bottle was 155 mL) were constructed as described in Oh et al., with modifications. All MFC-related power and voltage generation results were performed with three replicates. The two bottles with sideports (2.4 cm inner diameter) were clamped together with a treated Nafion 117 proton exchange membrane (Dupont, Wilmington, Del.) and one rubber gasket (3.5 cm outer diameter). The Nafion 117 membranes were cut into 4×4 cm squares, then pre-treated by heating for 1 hr in solutions of hydrogen peroxide (30%), sulfuric acid (0.5 M), and water. The top of each MFC chamber consisted of a rubber septum (42 cm diameter, ¼-inch thick) and plastic cap with a hole (Corning, Corning, N.Y.). All rubber septa had holes drilled in the center to allow an electrode to pass. For each anode chamber top, a carbon fiber brush electrode (Mill-Rose, Mentor, Ohio) from carbon fibers (PANEX 35 50K, Zoltek, St. Louis, Mo.) was twisted into two titanium wires 12.7 cm long as described in Lanas et al. (2013) *Bioresource Technol.* 148: 379-385. The wires were heat-treated at 450° C. for 30 min, as described in Feng et al. (2010) *J. Power Sources* 195: 1841-1844, and passed through the hole in the septum so that 2.8 cm of the top protruded. Then, the hole was closed with epoxy (Loctite, Dusseldorf, Germany). For each cathode chamber top, a carbon cloth circle (38 mm diameter;

Fuel Cell Store, Boulder, Colo.) was attached to a titanium wire (10-cm-long; 1.0 mm diameter; Alfa Aesar, Haverhill, Mass.), the wire was passed through the hole in the septum so that 3 cm of the wire protruded, and the hole was closed with epoxy.

MFCs were first inoculated with engineered *M. acetivorans* AA, with engineered *M. acetivorans* C2A, or with no *M. acetivorans*. MFCs were inoculated with engineered *M. acetivorans* AA or with engineered *M. acetivorans* C2A transformed with pES1-MaTmcr3 to convert methane to acetate. More specifically, engineered *M. acetivorans* AA or engineered *M. acetivorans* C2A from 200 mL cultures were collected by centrifugation (5,000 rpm for 20 min) and washed three times with HS medium lacking resazurin (i.e., HSNR). The final engineered *M. acetivorans* AA or engineered *M. acetivorans* C2A cell pellets were resuspended in HSNR with puromycin (100 mL) and placed in the anode chamber.

The anode chambers of MFCs were then inoculated with *G. sulfurreducens* PCA or with no *G. sulfurreducens* PCA. MFCs were inoculated with *G. sulfurreducens* PCA to catabolize acetate to produce electrical current. More specifically, *G. sulfurreducens* PCA from 200 mL cultures were collected by centrifugation (5,000 rpm for 20 min) and washed three times with HS medium lacking resazurin (i.e., HSNR). The final cell pellet was resuspended in HSNR with puromycin (100 mL) and placed in the anode chamber.

Catholyte solution (100 mL of 100 mM ferricyanide in 100 mM sodium phosphate, 5.8 mM ammonium chloride, and 1.7 mM potassium chloride, pH 7.0) was placed into each cathode chamber, and the caps were closed tightly before removing the MFC from the anaerobic atmosphere. The headspace of each anode chamber was filled with methane, unless otherwise indicated. The MFCs were placed at 30° C. and measurements of the voltage differential across the cathode and anode of each MFC was taken over about 1 k$\Omega$ resistance at a frequency of 0.05 s$^{-1}$ (with data displayed daily) using a 16-channel differential analog input module (NI 9205; National Instruments, Austin, Tex.).

Several days after inoculation with *G. sulfurreducens* PCA, MFCs were inoculated with methane-acclimated sludge, with no sludge, with sludge supernatants, or with electron shuttle molecules as indicated. With regard to methane-acclimated sludge, MFCs were inoculated with methane-acclimated sludge to provide additional microorganisms to produce electrical current from methane and/or methane catabolism byproducts. MFCs were inoculated with methane-acclimated sludge once the voltage of each MFC decreased to a threshold value of 150 mV or below. To inoculate with methane-acclimated sludge, 2 mL of each of the seven Round 3 methane-acclimated sludge cultures described in Table 2 of Example 2 above were combined with 4 mL of the initial sludge isolate. This 18 mL of sludge was centrifuged and resuspended in a total of 8 mL HSNR with puromycin, then the resuspension (2 mL) was injected into each anode chamber.

Methane-Acclimated Sludge Replacements. With regard to sludge supernatants, MFCs were inoculated with supernatants from methane-acclimated sludge by combining 2 mL of each of the seven Round 3 methane-acclimated sludge cultures described in Table 2 of Example 2 above with 4 mL of the initial sludge isolate. This 18 mL of sludge was centrifuged and about 4 mL of filter-sterilized supernatant was added to each MFC.

With regard to electron shuttle molecules, MFCs were inoculated with electron shuttle molecules as replacements for methane-acclimated sludge. Specifically, MFCs were inoculated with humic acids (0.5%), FMN (0.5 mM; Sigma-Aldrich), FAD (0.5 mM; Alfa Aesar, Tewksbury, Mass.), or AQDS (5 mM; Carbosynth, Berkshire, UK), which were included as indicated by adding the sterile solutions into HSNR with puromycin to the final concentrations indicated.

Scanning electron microscopy. Cellular attachments to anodes were visualized by scanning electron microscopy (i.e., SEM; Sigma VP-FESEM, Zeiss, Oberkochen, Germany). Samples for SEM were fixed by placing carbon fibers from the anode brush in glutaraldehyde (2.5%) in sodium phosphate buffer (0.1 M, pH 7.2), and incubating at room temperature for 1 h. The samples were then washed with increasing concentrations of ethanol: 25%, 50%, 70%, 85%, 95%, or 100% (three times). Samples were dried via critical point drying before visualizing by SEM.

Methane-Acclimated Sludge Microorganism Identification. To determine which microorganisms were likely active in the methane-acclimated sludge, 16S rDNA analyses were made for original sludge samples, for methane-acclimated sludge, for methane-acclimated sludge employed in MFCs generating electrical current (i.e., with a methane headspace) and for methane-acclimated sludge employed in MFCs not generating electrical current (i.e., MFCs with no methane headspace). More specifically, genomic DNA was extracted directly from original sludge samples, methane-acclimated sludge samples, and anode chambers of MFCs using the UltraClean Microbial DNA Isolation Kit (MoBio, Carlsbad, Calif.). The v3-v4 hypervariable region of 16S rDNA was amplified using primers PRO341-f and PRO801-r, which is universal for prokaryotes (both Archaea and Bacteria domains) with Ilumina (San Diego, Calif.) adapters attached for downstream processing as described in Takahashi et al. (2014) *PloS one* 9: e105592. Amplicon libraries were further processed and analyzed by the Genome Sciences Facility at Penn State Hershey College of Medicine using the MiSeq (Illumina) platform according to manufacturer specifications.

PRO341-f is the forward primer and PRO801-r is the reverse primer. PRO341-f has the sequence: TCGTCGGCAGCGTCAGATGTGTATAAGA-GACAGCCTACGGGNBGCASCAG (SEQ ID NO:7) wherein TCGTCGGCAGCGTCAGATGTGTATAAGA-GACAG (SEQ ID NO: 8) is an adapter and PRO801-r has the sequence: GTCTCGTGGGCTCG-GAGATGTGTATAAGAGACAGGAC-TACNVGGGTATCTA ATCC (SEQ ID NO: 9) wherein GTCTCGTGGGCTCGGAGATGTGTATAAGAGACAG (SEQ ID NO: 10) is an adapter.

Adapters used are Illumina 5' adapters. Degenerate nucleotides are denoted according to the International Union of Pure and Applied Chemistry where N represents A, C, T, or G; B represents C, G, or T; S represents G or C; and V represents A, C, or G.

Figure 4A:
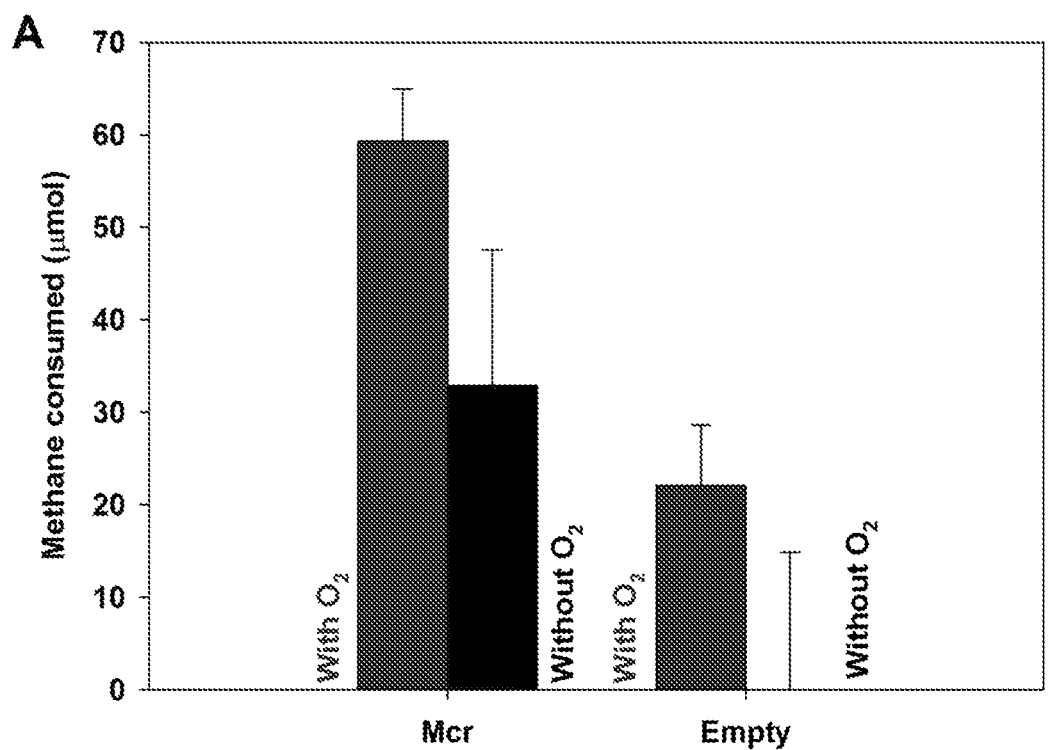
FIG. 4A is a bar graph of Methane Consumed (μmol) in MFCs inoculated with: (i) air adapted *M. acetivorans* transformed with pES1-MATmcr3 plasmids (i.e., Mcr) placed at a high cell-density under a headspace of pure methane or methane and 1% oxygen; and (ii) air adapted *M. acetivorans* transformed with pES1 plasmids (i.e., Empty) placed at a high cell-density under a headspace of pure methane or methane and 1% oxygen. The amounts of methane consumed were quantified, with averages and standard deviations between three replicates shown.
Figure 4B:
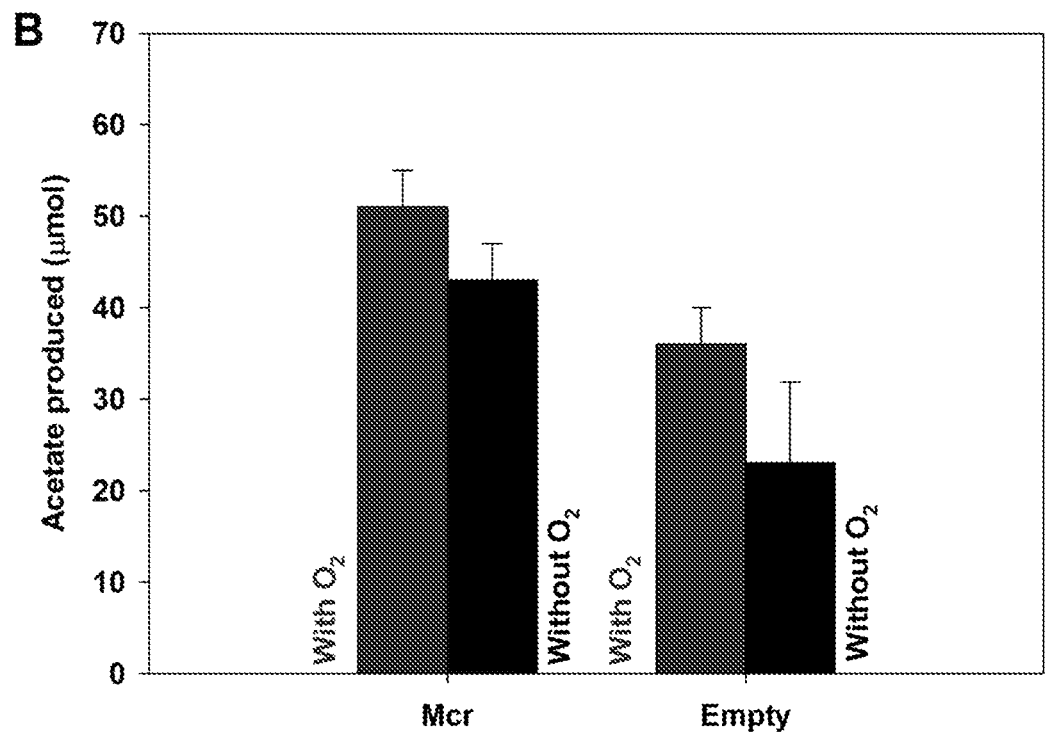
FIG. 4B is a bar graph of Acetate Produced (μmol) in MFCs inoculated with: (i) air adapted *M. acetivorans* transformed with pES1-MATmcr3 plasmids (i.e., Mcr) placed at a high cell-density under a headspace of pure methane or methane and 1% oxygen; and (ii) air adapted *M. acetivorans* transformed with pES1 plasmids (i.e., Empty) placed at a high cell-density under a headspace of pure methane or methane and 1% oxygen. The amounts of acetate produced were quantified, with averages and standard deviations between three replicates shown.

Results—Methane Consumption, Acetate Production, and Voltage and Power Generation. As shown in FIGS. 4A-4B, *M. acetivorans* AA transformed with PES1-MATmcr3 tolerated oxygen and oxidized methane to produce acetate. Despite this, the MFCs were operated anaerobically.

Figures 5A, 5B:
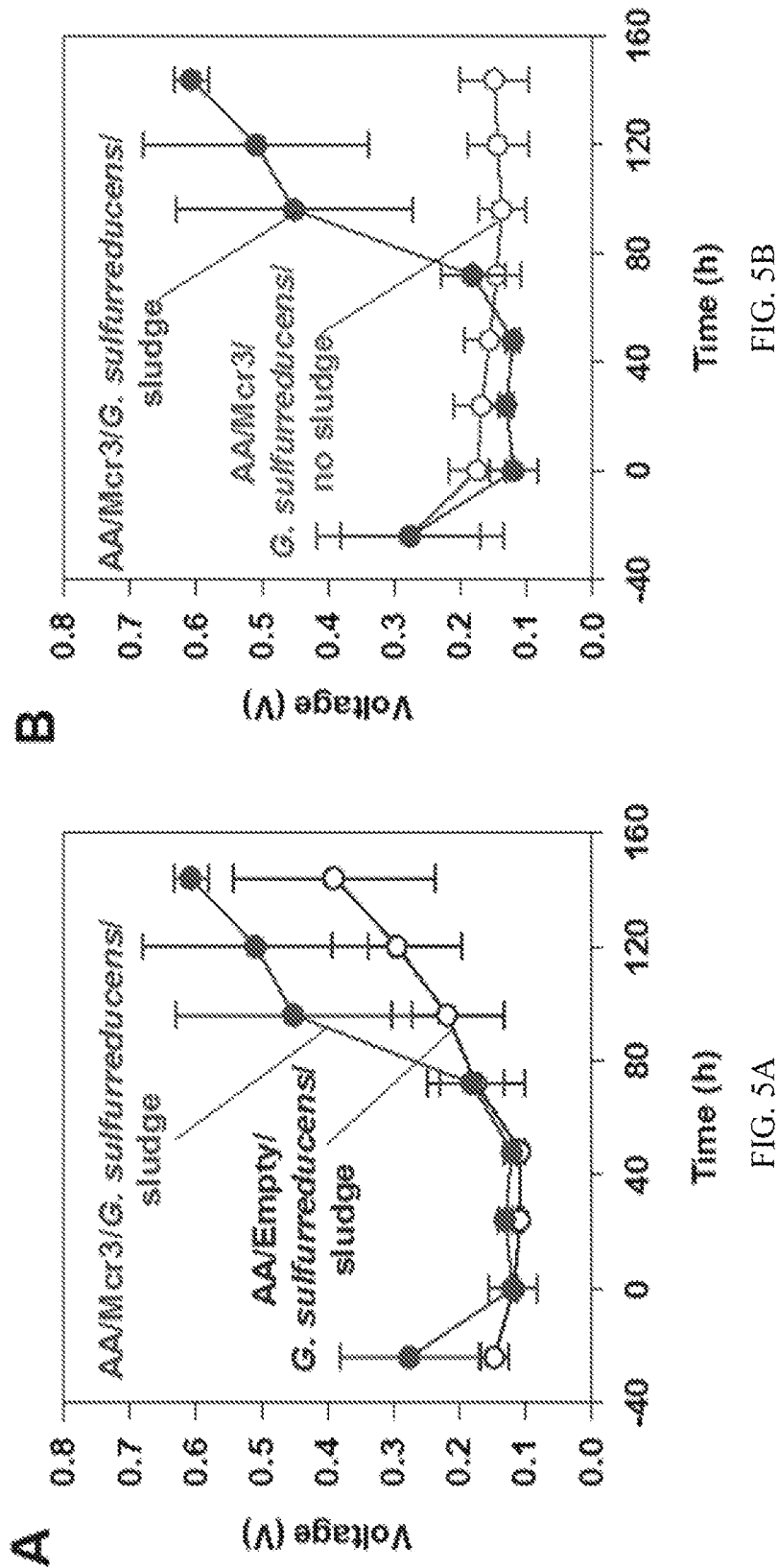
FIG. 5A is a graph of Time (hours, h) with respect to Voltage (V) generated in MFCs inoculated with: (i) a consortium of engineered *M. acetivorans* AA transformed with pES1-MATmcr3 plasmids (i.e., AA/Mcr3), *G. sulfurreducens* PCA (i.e., *G. sulfurreducens*), and methane-acclimated sludge (i.e., sludge) (filled circles), and (ii) a consortium of engineered *M. acetivorans* AA transformed with empty plasmid pES1 (i.e., AA/Empty), *G. sulfurreducens*, and sludge (empty circles). Time 0 is the time at which MFCs were inoculated with sludge. All values are represented as means±standard error of the mean (i.e., S.E.M.) from at least three replicate MFCs.
FIG. 5B is a graph of Time (h) with respect to Voltage (V) generated in MFCs inoculated with: (i) a consortium of *M. acetivorans* AA transformed with pES1-MATmcr3 plasmids (i.e., AA/Mcr3), *G. sulfurreducens* PCA (i.e., *G. sulfurreducens*), and methane-acclimated sludge (i.e., sludge) (filled circles), and (ii) a consortium of AA/Mcr3 and *G. sulfurreducens* without sludge (i.e., no sludge) (empty circles). Time 0 is the time at which MFCs were inoculated with sludge. Where no sludge was included, time 0 is indicated as 132 h after inoculation with AA/Mcr3 and *G. sulfurreducens* and setup. All values are represented as means±standard error of the mean from at least three replicate MFCs.

As shown in FIG. 5A and Table 3 below, voltages increased to significant levels (approximately 0.6 V with an electrical current density 273 mA/m$^2$) a few days after inoculation of MFCs with methane-acclimated sludge (which also were previously inoculated with *M. acetivorans* AA and *G. sulfurreducens* PCA).

TABLE 3

Maximum Power Generation and Electrical Current Densities in MFCs

| MFC conditions | Maximum power (mW/m$^2$) | Maximum electrical current density (mA/m$^2$) |
|---|---|---|
| AA/Mcr3/*G. sulfurreducens*/sludge | 168 ± 9 | 273 ± 7 |
| AA/Empty/*G. sulfurreducens*/sludge | 80 ± 70 | 200 ± 100 |
| C2A/Mcr3/*G. sulfurreducens*/sludge | 26 ± 9 | 110 ± 20 |
| AA/Mcr3/no *G. sulfurreducens*/sludge | 20 ± 10 | 90 ± 30 |
| AA/Mcr3/*G. sulfurreducens*/sludge, no methane | 3.0 ± 0.2 | 36 ± 1 |
| no AA/no Mcr3/no *G. sulfurreducens*/no sludge | 4.5 ± 0.4 | 45 ± 2 |
| no AA/no Mcr3/no *G. sulfurreducens*/sludge | 0.2 ± 0.1 | 9 ± 3 |
| AA/Mcr3/no *G. sulfurreducens*/no sludge | 20 ± 20 | 80 ± 40 |
| AA/Empty/no *G. sulfurreducens*/no sludge | 7 ± 5 | 90 ± 50 |

With regard to Table 3 above, maximum power and electrical current densities were normalized by the cathode surface area of 0.00227 m$^2$. All MFCs included methane in the headspace unless otherwise indicated. At time 0, MFCs included the engineered *M. acetivorans* AA containing pES1-MATmcr3 plasmids (i.e., AA/Mcr3), the engineered *M. acetivorans* AA including empty pES1 plasmids (i.e., AA Empty), *M. acetivorans* C2A containing pES1-MATmcr3 plasmids (i.e., C2A/Mcr3), no *M. acetivorans* strains (i.e., no AA/no Mcr3), and *G. sulfurreducens*. Methane-acclimated sludge was added to the MFCs as indicated once the voltage decreased to below a threshold value of 150 mV. Averages and standard deviations between at least three replicates are shown.

Figures 5C, 5D:
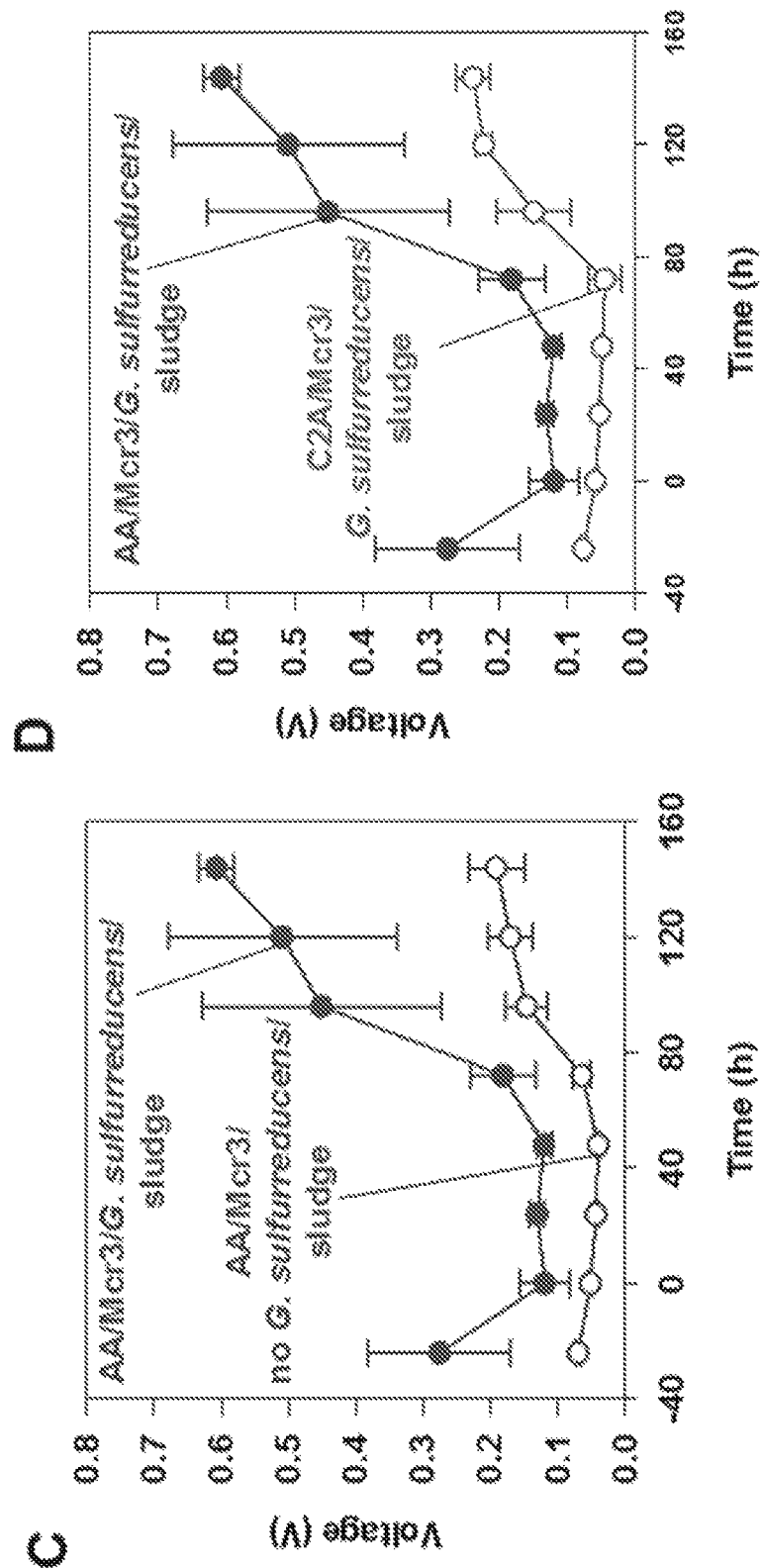
FIG. 5C is a graph of Time (h) with respect to Voltage (V) generated in MFCs inoculated with: (i) a consortium of *M. acetivorans* AA transformed with pES1-MATmcr3 plasmids (i.e., AA/Mcr3), *G. sulfurreducens* PCA (i.e., *G. sulfurreducens*), and methane-acclimated sludge (i.e., sludge) (filled circles), and (ii) a consortium of AA/Mcr3 and sludge without *G. sulfurreducens* (i.e., no *G. sulfurreducens*) (empty circles). Time 0 is the time at which MFCs were inoculated with sludge. All values are represented as means±standard error of the mean from at least three replicate MFCs.
FIG. 5D is a graph of Time (h) with respect to Voltage (V) generated in MFCs inoculated with: (i) a consortium of *M. acetivorans* AA transformed with pES1-MATmcr3 plasmids (i.e., AA/Mcr3), *G. sulfurreducens* PCA (i.e., *G. sulfurreducens*), and methane-acclimated sludge (i.e., sludge) (filled circles), and (ii) a consortium of engineered *M. acetivorans* C2A transformed with pES1-MATmcr3 plasmids (i.e., C2A/Mcr3) *G. sulfurreducens*, and sludge (empty circles). Time 0 is the time at which MFCs were inoculated with sludge. All values are represented as means±standard error of the mean from at least three replicate MFCs.
Figures 5E, 5F:
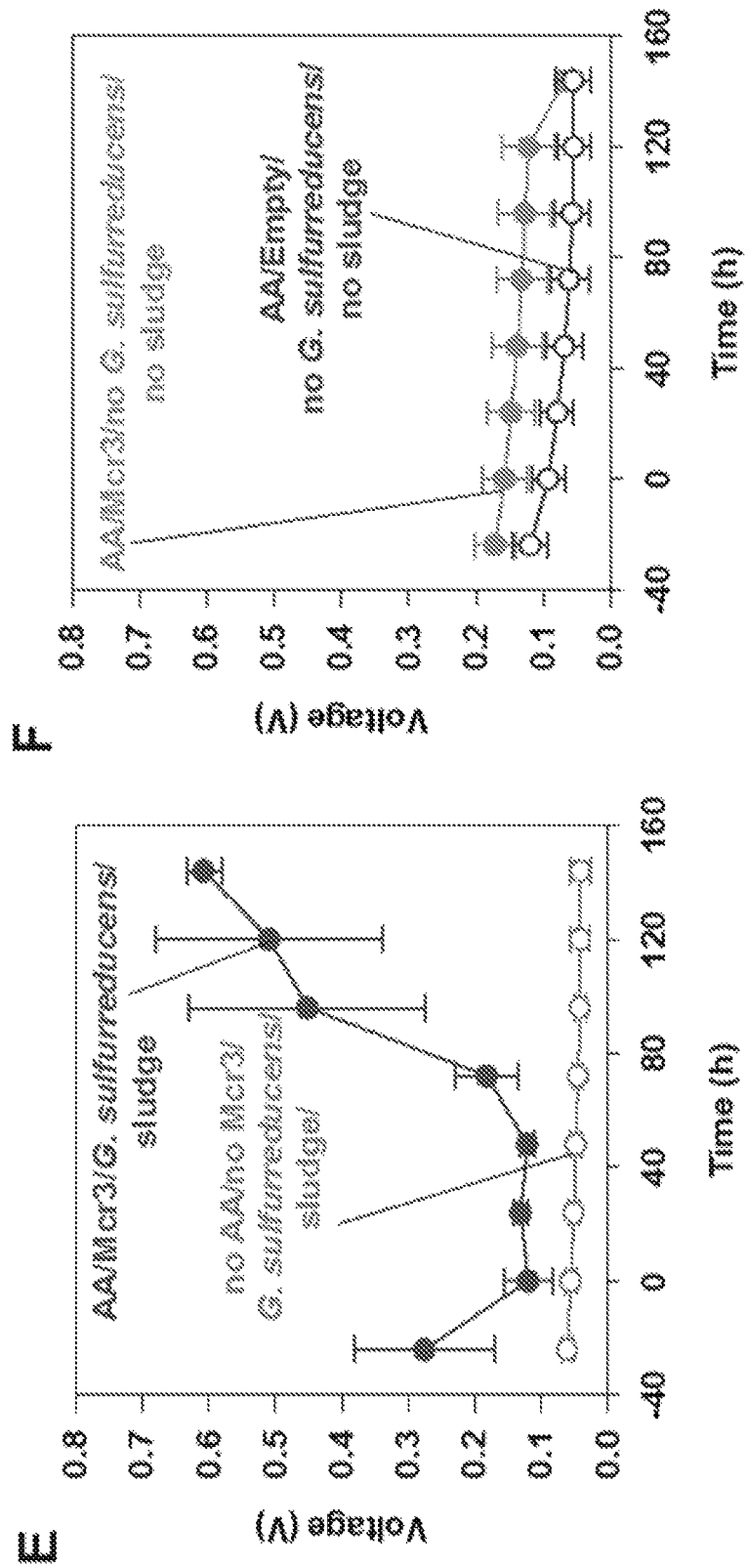
FIG. 5E is a graph of Time (h) with respect to Voltage (V) generated in MFCs inoculated with: (i) a consortium of *M. acetivorans* AA transformed with pES1-MATmcr3 plasmids (i.e., AA/Mcr3), *G. sulfurreducens* PCA (i.e., *G. sulfurreducens*), and methane-acclimated sludge (i.e., sludge) (filled circles), and (ii) a consortium of *G. sulfurreducens* and sludge without AA/Mcr3 (i.e., no AA/no Mcr3) (empty circles). Time 0 is the time at which MFCs were inoculated with sludge. All values are represented as means±standard error of the mean from at least three replicate MFCs.
FIG. 5F is a graph of Time (h) with respect to Voltage (V) generated in MFCs inoculated with: (i) *M. acetivorans* AA transformed with pES1-MATmcr3 plasmids (i.e., AA/Mcr3), no *G. sulfurreducens* PCA (i.e., no *G. sulfurreducens*), and no methane-acclimated sludge (i.e., no sludge) (filled circles), and (ii) engineered *M. acetivorans* AA transformed with empty plasmid pES1 (i.e., AA/Empty), no *G. sulfurreducens*, and no sludge (empty circles). Where no sludge was included, time 0 is indicated as 132 h after inoculation with AA/Mcr3 or AA/Empty and setup. All values are represented as means±standard error of the mean from at least three replicate MFCs.
Figures 5G, 5H:
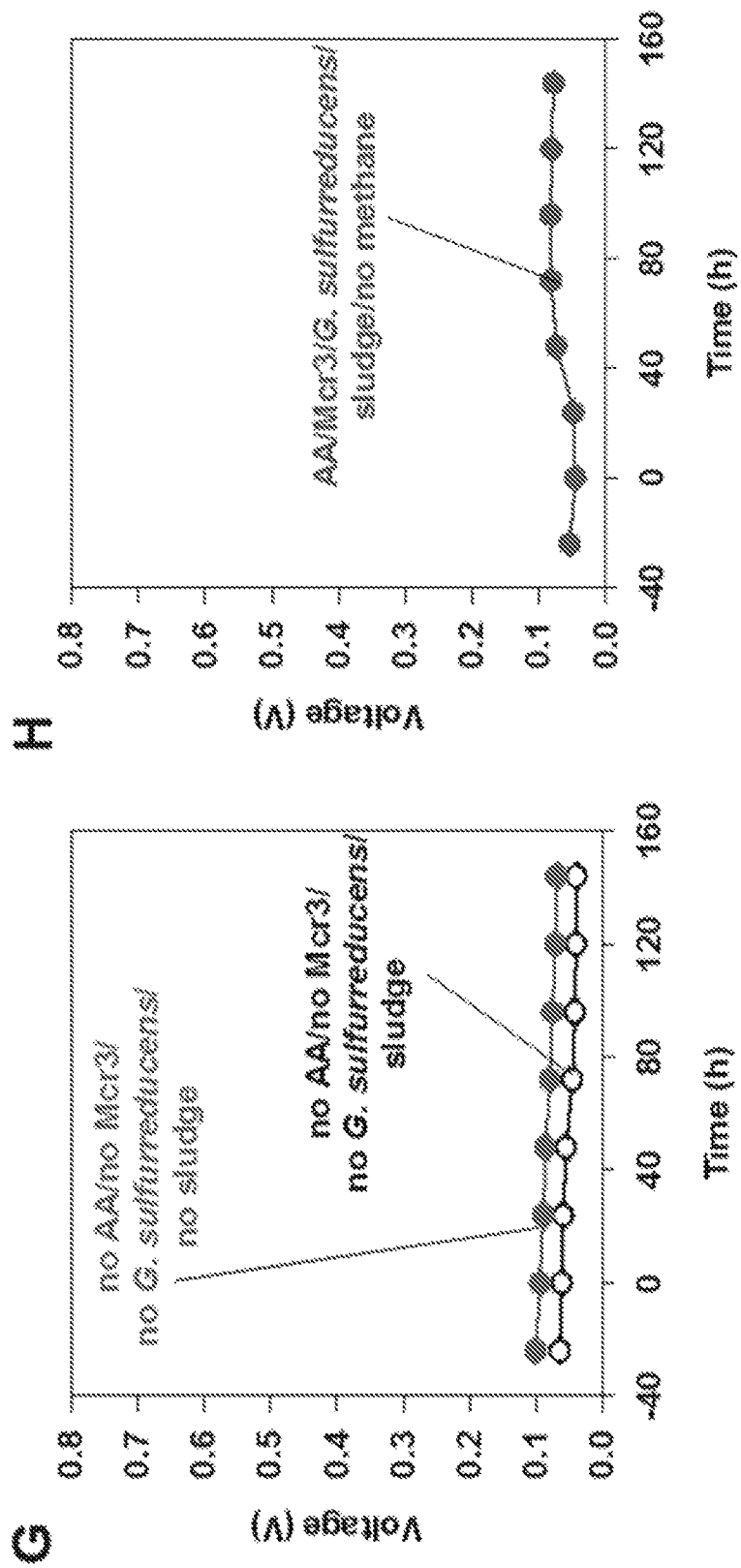
FIG. 5G is a graph of Time (h) with respect to Voltage (V) generated in MFCs inoculated with: (i) a consortium of no *M. acetivorans* AA transformed with pES1-MATmcr3 (i.e., no AA/no Mcr3), no *G. sulfurreducens* PCA, and no sludge (filled circles), and (ii) no AA/no Mcr3, no *G. sulfurreducens*, and sludge (empty circles). Time 0 is the time at which MFCs were inoculated with sludge. Where no sludge was included, time 0 is indicated as 132 h after setup. All values are represented as means±standard error of the mean from at least three replicate MFCs.
FIG. 5H is a graph of Time (h) with respect to Voltage (V) generated in MFCs inoculated with *M. acetivorans* AA transformed with pES1-MATmcr3 plasmids (i.e., AA/Mcr3), *G. sulfurreducens* PCA (i.e., *G. sulfurreducens*), and methane-acclimated sludge in the absence of methane in the MFC headspace (i.e., no methane) (filled circles). Time 0 is the time at which MFCs were inoculated with sludge. All values are represented as means±standard error of the mean from at least three replicate MFCs.

As shown in FIG. 5B and Table 3 above, the absence of methane-acclimated sludge in the MFCs led to no appreciable electrical current. Additionally, the absence of *G. sulfurreducens* led to little electrical current (see FIG. 5C and Table 3 above). AA/Mcr3 generated more electrical current than C2A/Mcr3 (see FIG. 5D and Table 3 above), and no electrical current was generated in the absence of AA/Mcr3 (see FIG. 5E and Table 3 above) or with only AA/Mcr3 (see FIG. 5F and Table 3 above). Additionally, methane-acclimated sludge alone with methane led to no appreciable electrical current (see FIG. 5G and Table 3 above), and, without methane, the consortium of AA/Mcr3, *G. sulfurreducens*, and methane-acclimated sludge led to no appreciable electrical current (see FIG. 5H and Table 3). Therefore, without being bound by the theory, it is believed that the consortium of AA/Mcr3, *G. sulfurreducens*, and sludge are effective in generating electrical current from methane.

Additionally, as shown in Table 4 below, methane consumption followed voltage generation trends in that MFCs inoculated with a consortium of AA/Mcr3, *G. sulfurreducens*, and methane-acclimated sludge had the highest methane consumption.

TABLE 4

Methane Consumption in 40 Days

| MFC | Methane consumed (µmol) |
|---|---|
| AA/Mcr3/*G. sulfurreducens*/sludge | 260 ± 40 |
| AA/Empty/*G. sulfurreducens*/sludge | 130 ± 40 |
| AA/Mcr3/no *G. sulfurreducens*/no sludge | 50 ± 50 |
| AA/Empty/no *G. sulfurreducens*/no sludge | 0 ± 100 |

With regard to Table 4 above, methane loss from the no AA/no Mcr3/no *G. sulfurreducens*/sludge MFCs was subtracted from each MFC to determine the total methane consumption. Averages and standard deviations between three replicates are shown. All MFCs included methane in the headspace. At time 0, MFCs included the following, as indicated: AA/Mcr3, AA/Empty, *G. sulfurreducens*, and/or sludge. Sludge was added to the MFCs once the voltage of each indicated MFC decreased to a threshold value of 150 mV or below (i.e., after 6 or 15 days for AA/Mcr3/*G. sulfurreducens*/sludge and AA/Empty/*G. sulfurreducens*/sludge, or after 15 d for no AA/no Mcr3/no *G. sulfurreducens*/sludge). Methane amounts were measured in the anode chambers of all MFCs after 40 days.

As shown in Table 4 above, methane consumption in MFCs with AA/Mcr3 but without both *G. sulfurreducens* and sludge exhibited little methane consumption. Without being bound by the theory, it is believed that because no extra electron acceptor was included in the anode chamber for methane consumption, electrical current was generated as a means to remove excess electrons from the process for methane consumption to occur. Additionally, it is believed that methane losses were not due to leaks, since no oxygen was detected. Further, referencing Table 4 above and without being bound by the theory, it is believed that in MFCs including *G. sulfurreducens* and sludge, production of Mcr from ANME allowed for greater consumption of the methane substrate.

Figure 6:
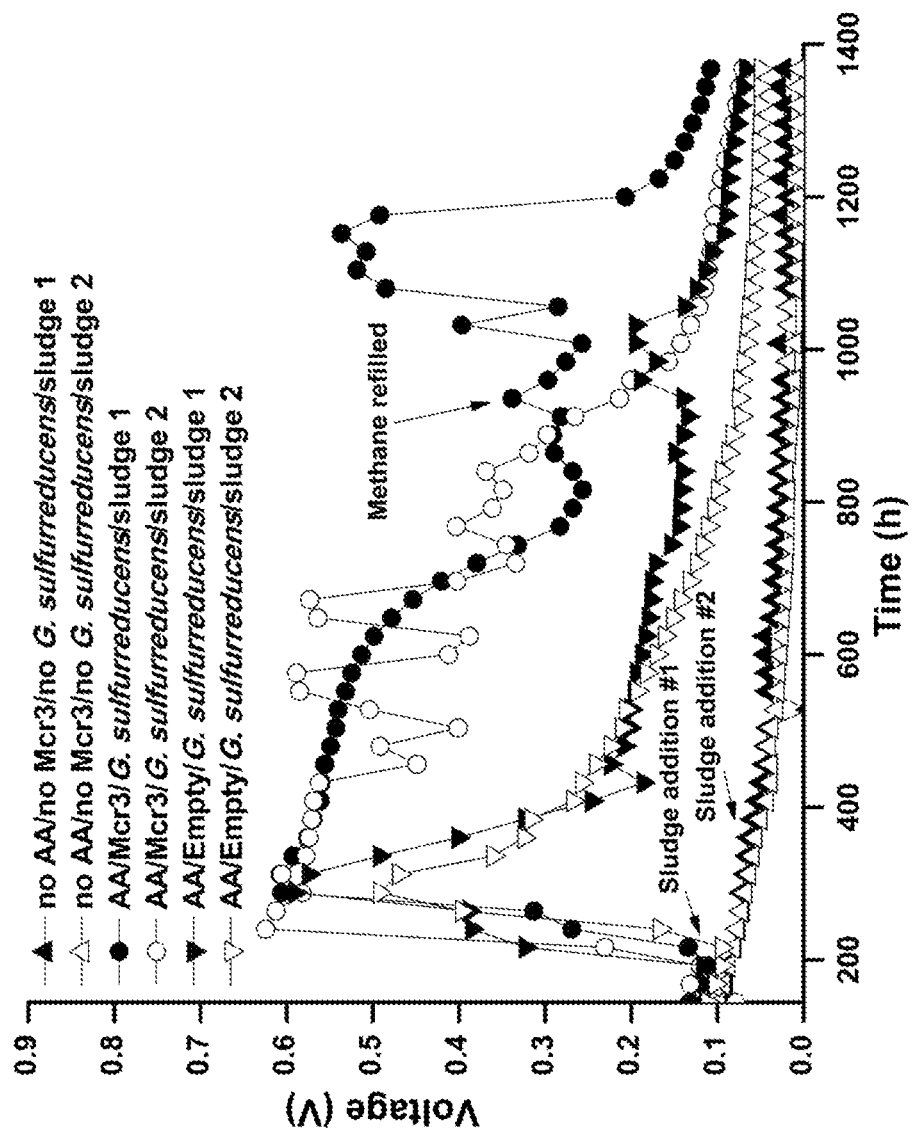
FIG. 6 is a graph of Time (h) with respect to Voltage (V) generated in MFCs inoculated with: (i) no *M. acetivorans* AA transformed with pES1-MATmcr3 (i.e., no AA/no Mcr3), no *G. sulfurreducens* PCA (i.e., no *G. sulfurreducens*), and methane-acclimated sludge added after 6 days (i.e., sludge 1) (filled right-side up triangles); (ii) no AA/noMcr3, no *G. sulfurreducens*, and methane-acclimated sludge added after 15 days (i.e., sludge 2) (empty right-side up triangles); (iii) *M. acetivorans* AA transformed with pES1-MATmcr3 plasmids (i.e., AA/Mcr3), *G. sulfurreducens* PCA (i.e., *G. sulfurreducens*), and sludge 1 (filled circles); (iv) AA/Mcr3, *G. sulfurreducens*, and sludge 2 (empty circles); (v) *M. acetivorans* AA transformed with empty plasmid pES1 (i.e., AA/Empty), *G. sulfurreducens*, and sludge 1 (filled upside down triangles); and (vi) AA/Empty, *G. sulfurreducens*, and sludge 2 (empty upside down triangles). Methane consumption was quantified after 40 days, and replenished at that time.
Figure 7A:
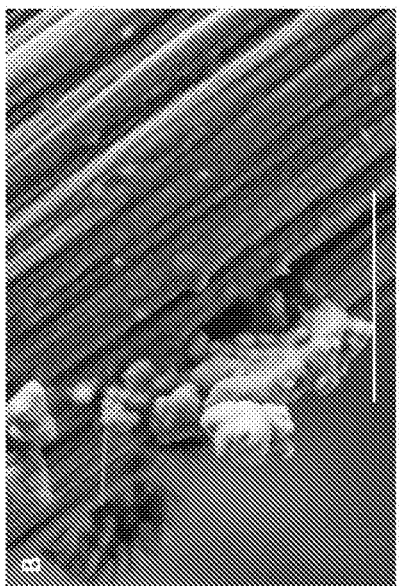
FIG. 7A is a scanning electron micrograph of anode fibers from an MFC inoculated with *M. acetivorans* AA transformed with pES1-MATmcr3 plasmids. The scale bar is 1 μM and arrows indicate cells.
Figure 7B:
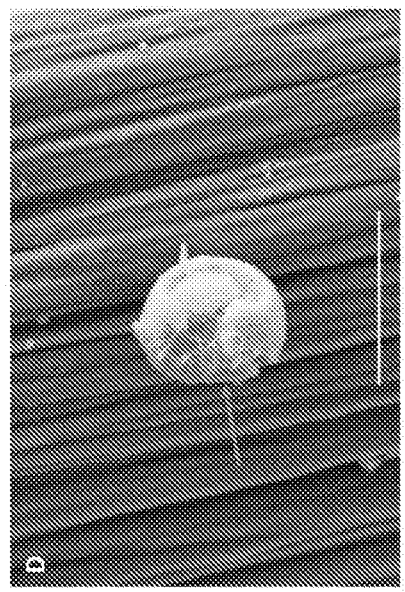
FIG. 7B is a scanning electron micrograph of anode fibers from an MFC inoculated with *M. acetivorans* AA transformed with pES1-MATmcr3 plasmids, *G. sulfurreducens* PCA, and methane-acclimated sludge. The scale bar is 1 μM and arrows indicate cells.
Figure 7C:
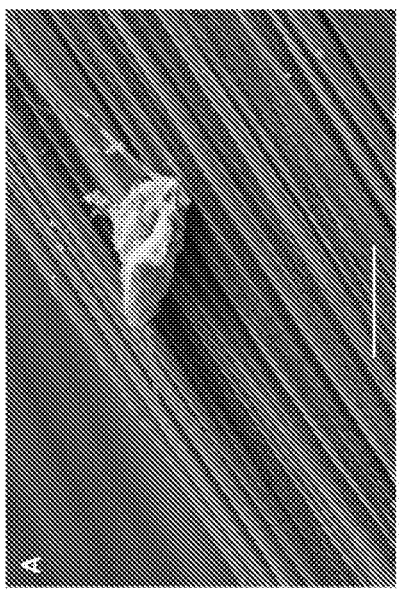
FIG. 7C is a scanning electron micrograph of anode fibers from an MFC inoculated with *M. acetivorans* AA transformed with pES1-MATmcr3 plasmids, *G. sulfurreducens* PCA, and methane-acclimated sludge. The scale bar is 1 μM and arrows indicate cells.
Figure 7D:
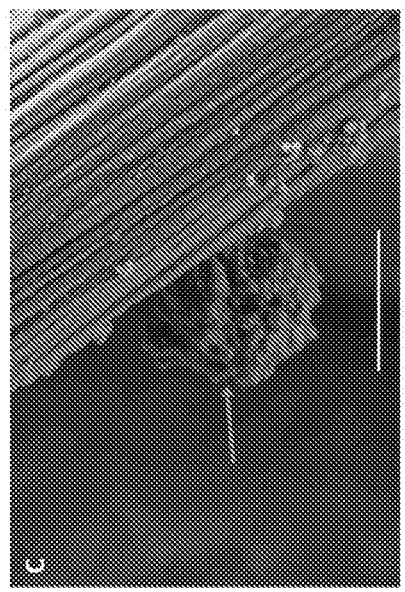
FIG. 7D is a scanning electron micrograph of anode fibers from an MFC inoculated with *M. acetivorans* AA transformed with pES1-MATmcr3 plasmids, *G. sulfurreducens* PCA, and methane-acclimated sludge. The scale bar is 1 µM and arrows indicate cells.

Referencing FIG. 6, the re-filling of MFCs with more methane caused an increase in voltage only for MFCs with AA/Mcr3 producing Mcr from ANME with *G. sulfurreducens* and methane-acclimated sludge. Corroborating the methane consumption results, production of Mcr from ANME was effective for sustaining production of electrical current (see, e.g., a 3-fold increase in voltage compared to no production of Mcr from ANME, as shown in FIG. 6). Production of Mcr also increased power output (see Table 3 above).

Figures 8A, 8B, 8C:
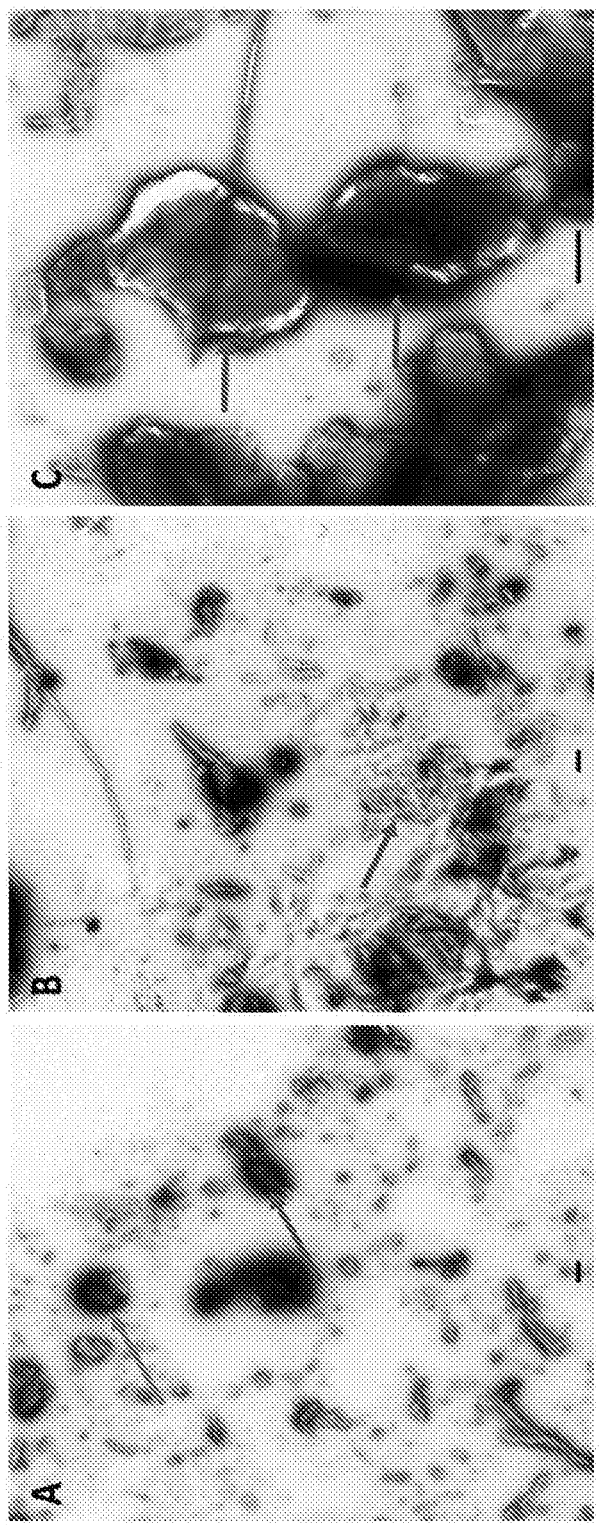
FIG. 8A is a transmission electron microscope image of salt crystals and *M. acetivorans* C2A transformed with pES1-MATmcr3 grown in HS medium with methane and 10 mM $FeCl_3$, with a 1 µM scale and arrows indicating salt crystals (bottom right arrow) and putative cells (top left arrow)
FIG. 8B is a transmission electron microscope image of salt crystals and *M. acetivorans* C2A transformed with pES1-MATmcr3 grown in HS medium with methane and 10 mM $FeCl_3$, with a 1 µM scale and an arrow indicating salt crystals.
FIG. 8C is a transmission electron microscope image of salt crystals and *M. acetivorans* C2A transformed with pES1-MATmcr3 grown in HS medium with methane and 10 mM $FeCl_3$, with a 1 µM scale and arrows indicating salt crystals.

Imaging. As shown in FIGS. 7A-7D, only individual cells were seen attached to the anode. Without being bound by the theory, it is believed that because individual cells were attached to the anode, electrical current was generated through indirect contact (such as, e.g., via electron shuttle molecules) rather than via direct contact. Further, without being bound by the theory, it is believed that the absence of cell-like structures in the MFCs not inoculated with cells indicates that the structures shown in FIGS. 7A-7D are cells. Also without being bound by the theory, it is believed that the absence of distinctly rod-shaped bacteria attached to the anodes indicates that *G. sulfurreducens* did not play a major role in electrical current generation because *G. sulfurreducens* is believed to generate electrical current via direct contact. While it is believed that AA/Mcr3 develops biofilms on FeCl$_3$ precipitates when grown with methane as a substrate, the carbon fiber anode surfaces in FIGS. 7A-7D are believed to be much smoother and more structured than FeCl$_3$ precipitates (see e.g., FIGS. 8A-8C). Thus, without being bound by the theory, it is believed that it was difficult for *M. acetivorans* strains to attach to the carbon fiber anode surfaces.

Figure 9:
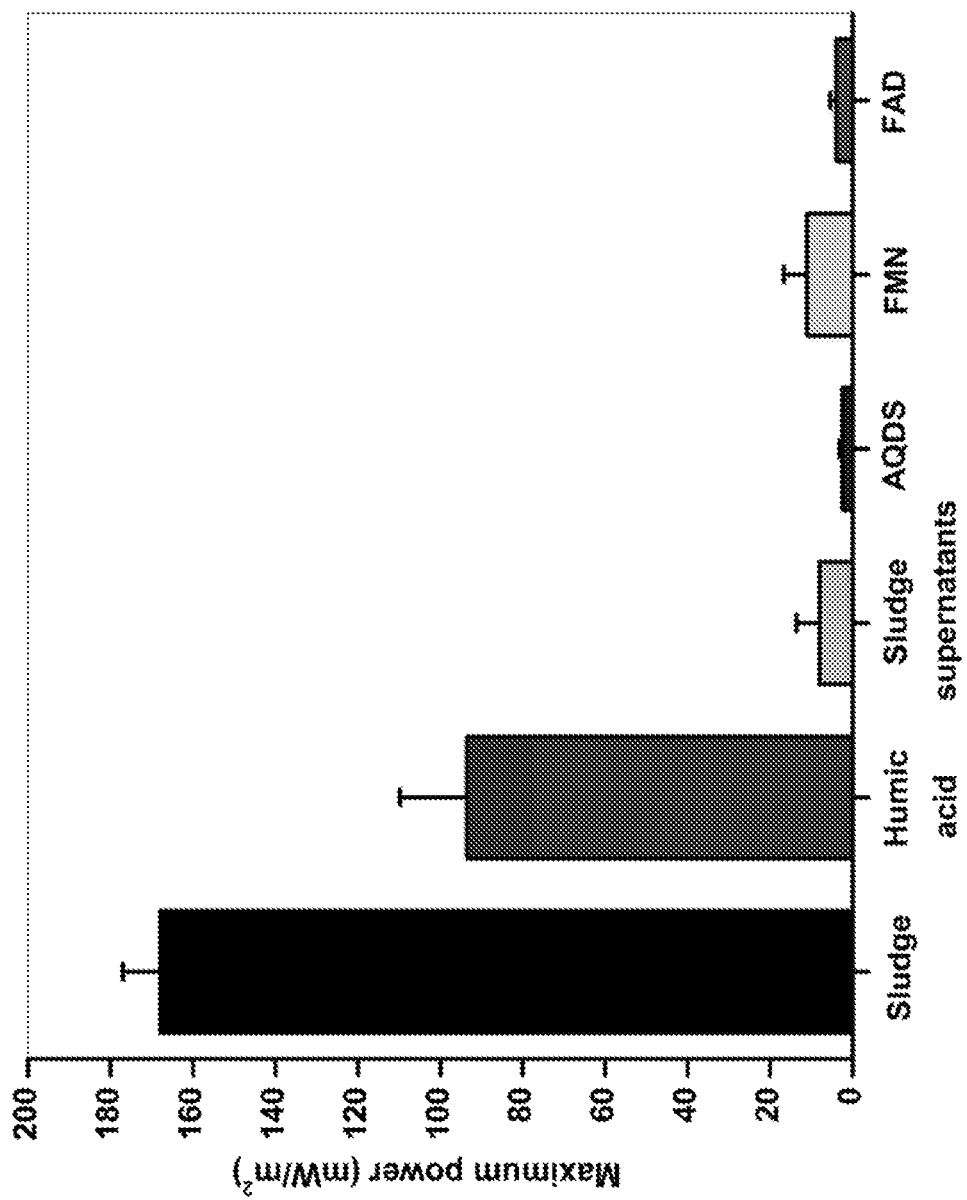
FIG. 9 is a bar graph of Maximum Power ($mW/m^2$) of MFCs inoculated with: (i) *M. acetivorans* AA transformed with pES1-MATmcr3 plasmids, *G. sulfurreducens* PCA, and methane-acclimated sludge (i.e., Sludge); (ii) *M. acetivorans* AA transformed with pES1-MATmcr3 plasmids, *G. sulfurreducens* PCA, and 0.5% humic acids (i.e., Humic acid); (iii) *M. acetivorans* AA transformed with pES1-MATmcr3 plasmids, *G. sulfurreducens* PCA, and supernatants from methane-acclimated sludge (i.e., Sludge supernatants); (iv) *M. acetivorans* AA transformed with pES1-MATmcr3 plasmids, *G. sulfurreducens* PCA, and 5 mM anthraquinone-2,6-disulfonate (i.e., AQDS); (v) *M. acetivorans* AA transformed with pES1-MATmcr3 plasmids, *G. sulfurreducens* PCA, and 0.5 mM riboflavin 5'-monophosphate (i.e., FMN); and (vi) *M. acetivorans* AA transformed with pES1-MATmcr3 plasmids, *G. sulfurreducens* PCA, and 0.5 mM flavin adenine dinucleotide (i.e., FAD). Maximum power generated in each MFC was normalized by the cathode surface area of $0.00227 m^2$. Averages and standard deviations are shown.

Methane-Acclimated Sludge Replacement. Referencing FIG. 9, sludge was replaced with electron shuttle molecules. More specifically, sludge was replaced with 0.5 mM FMN, 0.5 mM FAD, 5 mM AQDS, 0.5% humic acids, and supernatants from methane-acclimated sludge, as indicated. MFCs were inoculated with AA/Mcr3, *G. sulfurreducens*, and sludge, FMN, FAD, AQDS, humic acids, or supernatants from methane-acclimated sludge. Sludge or an electron shuttle was added once the voltage of each MFC decreased to below a threshold value of 150 mV. As shown in FIG. 9, humic acids were an effective replacement for sludge in MFCs containing AA/Mcr3 and *G. sulfurreducens*.

Methane-Acclimated Sludge Microorganism Identification. As shown in Table 5, the prevalent microorganism belonged to the genus *Paracoccus*. As internal controls, both *M. acetivorans* and *G. sulfurreducens* were detected as substantial community members in the MFCs where they were added as part of the synthetic consortium. As shown in Table 5, the omission of methane (and lack of significant electrical current) did not lead to notable changes in community composition, indicating that not many members proliferated substantially under such conditions. However, the relative metabolic activity of each genus member remains to be shown. As shown in Table 5, the acclimation of sludge samples to methane decreased the overall diversity.

Table 5. Genera Identified in Sludge and in the MFCs.

Relative compositions are displayed based on the number of identified 16S rDNA reads compared to the total reads and are characterized to the genus taxonomic level. Genera which make up at least 1% of the relative composition of each sample are displayed, and DNA reads belonging to these genera are considered for the total reads in each sample. "Original sludge" is the initial sludge 811 days after isolation, and the "Acclimated sludge" is the pooled seven Round 3 methane-acclimated sludge cultures (Table 6) after 567 days of incubation, with both of these sludge samples used to inoculate MFCs. MFCs included the air-adapted *M. acetivorans* host containing pES1-MATmcr3 ("AA/Mcr3") and *G. sulfurreducens*. Sludge was added to the indicated MFCs once the voltage of each MFC decreased to a threshold value of 150 mV or below. All MFCs included methane in the headspace except the "AA/Mcr3/*G. sulfurreducens*/sludge/no methane" sample. Samples from MFCs were taken after 40 or 65 days of incubation for the two "AA/Mcr3/*G. sulfurreducens*/sludge" samples, or after 16 days of incubation for the "AA/Mcr3/*G. sulfurreducens*/sludge/no methane" sample.

TABLE 5

| Genus | Relative composition (%) |
|---|---|
| Original sludge | |
| *Chlorobium* | 23 |
| *Phenylobacterium* | 7 |
| *Sulfuricurvum* | 5 |
| *Methanolinea* | 5 |
| *Methanothrix* | 3 |
| *Smithella* | 3 |
| *Methanoregula* | 2 |
| *Desulfobacca* | 2 |
| *Desulfomonile* | 1 |
| *Thiobacillus* | 1 |
| Acclimated sludge | |
| *Paracoccus* | 54 |
| *Truepera* | 7 |
| *Desulfobulbus* | 7 |
| *Nocardioides* | 2 |
| *Actinotalea* | 1 |
| AA/Mcr3/*G. sulfurreducens*/sludge #1 | |
| *Garciella* | 34 |
| *Paracoccus* | 24 |
| *Methanosarcina* | 20 |
| *Geobacter* | 16 |

TABLE 5-continued

| Genus | Relative composition (%) |
|---|---|
| *Geotoga* | 1 |
| AA/Mcr3/*G. sulfurreducens*/sludge #2 | |
| *Methanosarcina* | 36 |
| *Garciella* | 26 |
| *Geotoga* | 14 |
| *Paracoccus* | 10 |
| *Geobacter* | 8 |
| AA/Mcr3/*G. sulfurreducens*/sludge/no methane #1 | |
| *Methanosarcina* | 49 |
| *Geotoga* | 15 |
| *Garciella* | 13 |
| *Geobacter* | 11 |
| *Paracoccus* | 8 |

Table 6. History of Each of the 7 Sludge Cultures Acclimated to Methane.

The inoculations were done with 50 μL into 5 mL of medium, and cultures kept in HS-methane (unless a different headspace is indicated) with different terminal electron acceptors (TEAs). Cultures with the same TEA mentioned in third round cultures 1 and 2 are the same culture (not different replicates), and the cell lines came from the same original sludge isolate. The cultures were incubated at 37° C. without shaking.

TABLE 6

| Third round culture | First round TEA | Second round TEA | Third round TEA |
|---|---|---|---|
| 1 | 1 mM FeCl$_3$ | 1 mM FeCl$_3$ | 1 mM FeCl$_3$ |
| 2 | 1 mM FeCl$_3$ | 1 mM FeCl$_3$ | 1 mM FeCl$_3$, headspace of 80% CH$_4$ 20% CO$_2$ |
| 3 | 1 mM FeCl$_3$ | 1 mM FeCl$_3$ | 0.001 mM FeSO$_4$ |
| 4 | 1 mM FeCl$_3$ | 1 mM FeCl$_3$ | 0.001 mM FeCl$_3$ |
| 5 | 0.001 mM FeSO$_4$ | 0.001 mM FeSO$_4$ | 40 mM ferrihydrite |
| 6 | 0.001 mM FeSO$_4$ | 0.001 mM FeSO$_4$ | 1 mM FeCl$_3$ |
| 7 | 0.001 mM FeSO$_4$ | 0.001 mM FeSO$_4$ | 0.001 mM FeSO$_4$, headspace of 95% CH$_4$ 5% H$_2$ |

Example 4

Examination of *Geobacter* Biofilm on the Anode Electrode

To examine the *Geobacter* spp. biofilm on an anode carbon brush electrode after measuring the voltage, the putative biofilm on the brush was stained with Syto9 (Invitrogen: #L7007) and observed using a laboratory microscope (Zeiss Axio microscope). Three types of brush electrodes were observed. 1: an anode electrode from an anode chamber of a reactor, wherein the anode chamber contained *M. acetivorans*/pES1MATmcr3, *G. metallireducens*, and sludge, 2: an anode electrode from an anode chamber of a reactor, wherein the anode chamber contained *M. acetivorans*/pES1MATmcr3, *G. sulfurreducens*, and sludge, and 3: a carbon brush electrode not used in an MFC (negative control).

To visualize the biofilm the carbon brush electrodes were washed by dipping gently in 350 mL dH$_2$O in a 400 mL beaker (1×). Next, a portion of the brush was cut off with scissors. The portion of cut brush was stained with 5 µM Syto9 in 1 mL 1×PBS at room temperature in the dark for 30 minutes. After staining, the dye solution was removed and 200 µL 1×PBS was added. Then the stained brush portion was put between a slide and a coverslip. The fluorescence signal was analyzed using the lab microscope (Zeiss Axioscope.A1)

Fluorescence microscopic analysis showed that there were no cells found on the negative control brush. There was a biofilm found on the anode from the anode chamber containing G. metallireducens and there was a biofilm found on the anode from the anode chamber containing G. sulfurreducens; however, there was more biofilm present on the anode from the anode chamber containing G. metallireducens.

Example 5

Exoelectrogen Microbes that Produce Electrically-Conductive Appendages—Comparison of G. sulfurreducens and G. metallireducens in the Electricity Production from Methane The Geobacter strain (G. sulfurreducens) was compared with G. metallireducens in the anode compartment of two MFCs. The MFC reactors each included a Nafion 117 proton exchange membrane clamped between an anode chamber and a cathode chamber. An anode carbon brush electrode (12.7 cm long with roughly 8.1 cm covered by the carbon fibers with the carbon fibers covering a 2.7 cm diameter) was inserted into each anode chamber. A cathode carbon cloth electrode (38 mm diameter) was inserted into each cathode chamber. M. acetivorans/pES1MATmcr3 cultures were centrifuged using 4 centrifuge bottles (200 mL culture in each bottle). After removing the supernatant, 200 mL, of G. sulfurreducens and G. metallireducens were each collected from 2 bottles each by centrifugation. These centrifugations were done at 5,000 rpm for 20 min, 25° C. These collected pellets were washed three times with 5 mL HSNR and separately resuspended in a 100 mL HSNR with 2 µg/mL puromycin. HSNR is a high salts medium that lacks a carbon source. Then 100 mL of each suspension was introduced into a separate anode chamber. 100 mL of catholyte solution (100 mM potassium ferricyanide in 100 mM PBS, pH 7.0) was added to each cathode chamber. The MFC reactor set-up was performed in an anaerobic chamber after which the caps of each anode and cathode chamber were closed tightly and the reactors were taken out of the anaerobic chamber. Methane gas was purged into the headspace of only the anode compartment with at least 10 volumes exchanged (at 100 mL/min for 5 minutes). The voltages were measured between the anode and cathode across a 1 kΩ fixed resistance. After the voltage became less than 150 mV, sludge (2 mL) is added. The MFCs were incubated at 30° C.

Figure 10A:
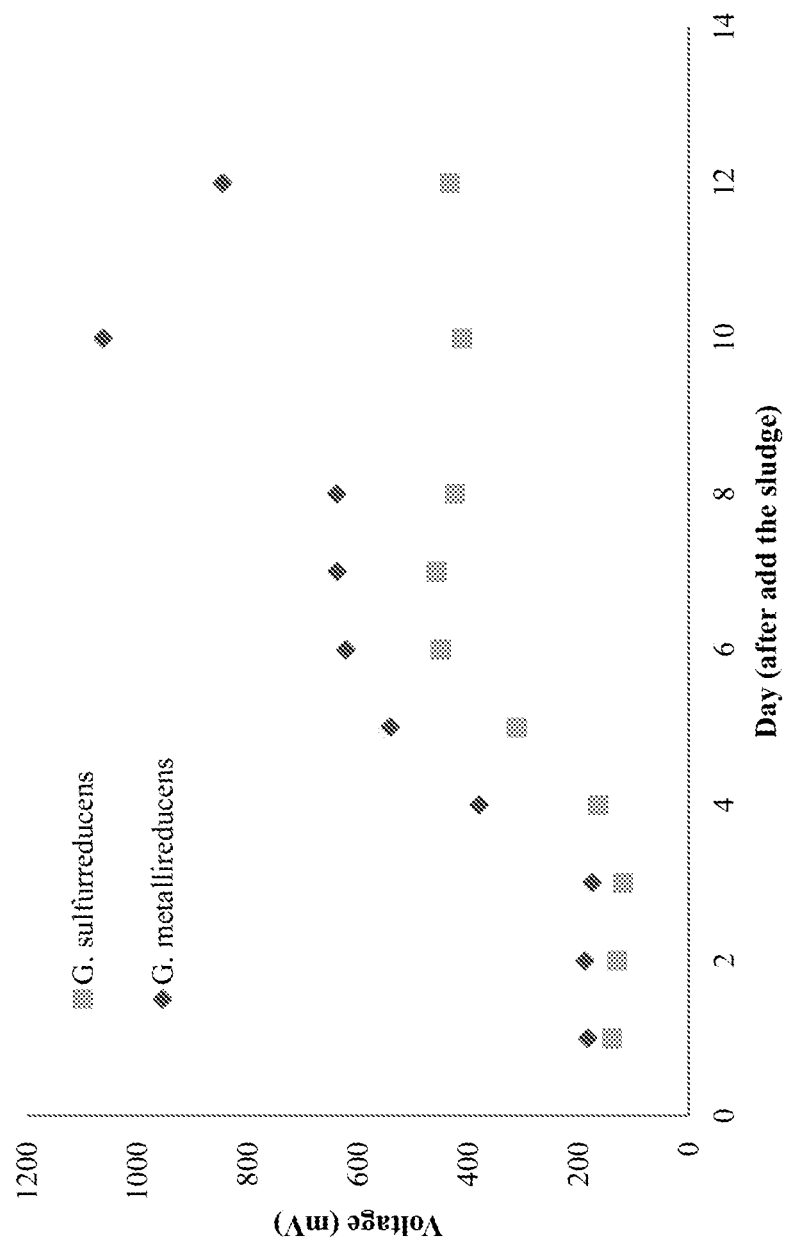
FIG. 10A is a graph showing a first comparison of: 1) an MFC reactor where the anode chamber contains *M. acetivorans*/pES1MATmcr3/*G. sulfurreducens*/sludge and 2) an MFC reactor where the anode chamber contains *M. acetivorans*/pES1MATmcr3/*G. metallireducens*/sludge. Circles represent measurements taken from the reactor containing *M. acetivorans*/pES1MATmcr3/*G. metallireducens*/sludge in the anode chamber and squares represent measurements taken from the reactor *M. acetivorans*/pES1MATmcr3/*G. sulfurreducens*/sludge in the anode chamber. These graphs are showing the measurement after adding sludge.
Figure 10B:
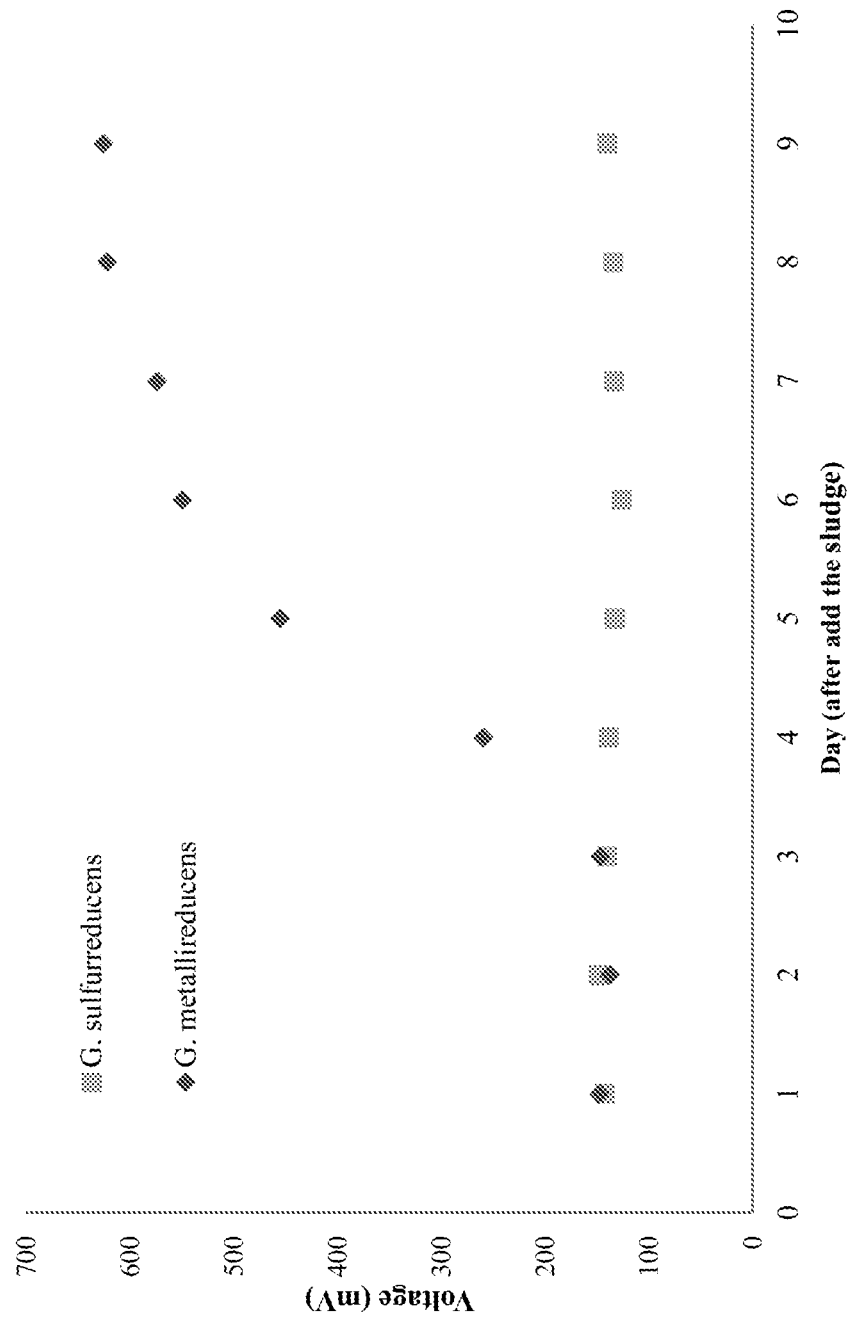
FIG. 10B is a graph showing a second comparison of: 1) an MFC reactor where the anode chamber contains *M. acetivorans*/pES1MATmcr3/*G. sulfurreducens*/sludge and 2) an MFC reactor where the anode chamber contains *M. acetivorans*/pES1MATmcr3/*G. metallireducens*/sludge. Circles represent measurements taken from the reactor containing *M. acetivorans*/pES1MATmcr3/*G. metallireducens*/sludge in the anode chamber and squares represent measurements taken from the reactor *M. acetivorans*/pES1MATmcr3/*G. sulfurreducens*/sludge in the anode chamber. These graphs are showing the measurement after adding sludge.

After adding the sludge, the voltage of both MFC reactors increased. The maximum voltages of the G. sulfurreducens-containing reactor was 456.7 mV-138.5 mV (original voltage)=318.2 mV. The maximum voltage of the G. metallireducens-containing reactor is 1062.5 mV-182.8 mV (original voltage)=879.7 mV. The same conditions were repeated in additional MFC reactors and it was found that the maximum voltages of G. sulfurreducens reactor was 148.7 mV-142.1 (original voltage)=6.6 mV and the maximum voltage of the 2nd G. metallireducens reactor was 640.2 mV-147.4 (original voltage)=492.8 mV. Therefore, the G. metallireducens reactors were 2.8-75-fold higher than G. sulfurreducens reactor. FIGS. 10A and 10B are graphs showing voltage measurements for each set of two reactors. FIG. 10A is a graph showing a first comparison of: 1) an MFC reactor where the anode chamber contains M. acetivorans/pES1MATmcr3/G. sulfurreducens/sludge and 2) an MFC reactor where the anode chamber contains M. acetivorans/pES1MATmcr3/G. metallireducens/sludge. FIG. 10B is a graph showing a second comparison of: 1) an MFC reactor where the anode chamber contains M. acetivorans/pES1MATmcr3/G. sulfurreducens/sludge and 2) an MFC reactor where the anode chamber contains M. acetivorans/pES1MATmcr3/G. metallireducens/sludge. Circles represent measurements taken from the reactor containing M. acetivorans/pES1MATmcr3/G. metallireducens/sludge in the anode chamber and squares represent measurements taken from the reactor M. acetivorans/pES1MATmcr3/G. sulfurreducens/sludge in the anode chamber. These graphs are showing the measurement after adding sludge.

Example 6

Impact of cytochrome C in the electricity production from methane by MFC.

Cytochrome C from equine heart was purchased from Sigma Aldrich (#C2506). Two MFC reactors were set up to compare the effect of cytochrome C (with and without cytochrome C).

The MFC reactors each included a Nafion 117 proton exchange membrane clamped between an anode chamber and a cathode chamber. An anode carbon brush electrode (12.7 cm long with roughly 8.1 cm covered by the carbon fibers with the carbon fibers covering a 2.7 cm diameter) was inserted into each anode chamber. A cathode carbon cloth electrode (38 mm diameter) was inserted into each cathode chamber. M. acetivorans/pES1MATmcr3 cultures were centrifuged using 4 centrifuge bottles (200 mL culture in each bottle). After removing the supernatant, 200 mL, of G. sulfurreducens and G. metallireducens were each collected from 2 bottles each by centrifugation. These centrifugations were done at 5,000 rpm for 20 min, 25° C. These collected pellets were washed three times with 5 mL HSNR and separately resuspended in a 100 mL HSNR with 2 µg/mL puromycin. Then 100 mL of each suspension was introduced into a separate anode chamber. 100 mL of catholyte solution (100 mM potassium ferricyanide in 100 mM PBS, pH 7.0) was added to each cathode chamber. The MFC reactor set-up was performed in an anaerobic chamber after which the caps of each anode and cathode chamber were closed tightly and the reactors were taken out of the anaerobic chamber. Methane gas was purged into the headspace of only the anode compartment with at least 10 volumes exchanged (at 100 mL/min for 5 minutes). The voltages were measured between the anode and cathode across a 1 kΩ fixed resistance. After the voltage became less than 150 mV, sludge (2 mL) and cytochrome C from equine heart (25 mg) is added (final conc.=20 µM). The MFCs were incubated at 30° C.

Figure 11:
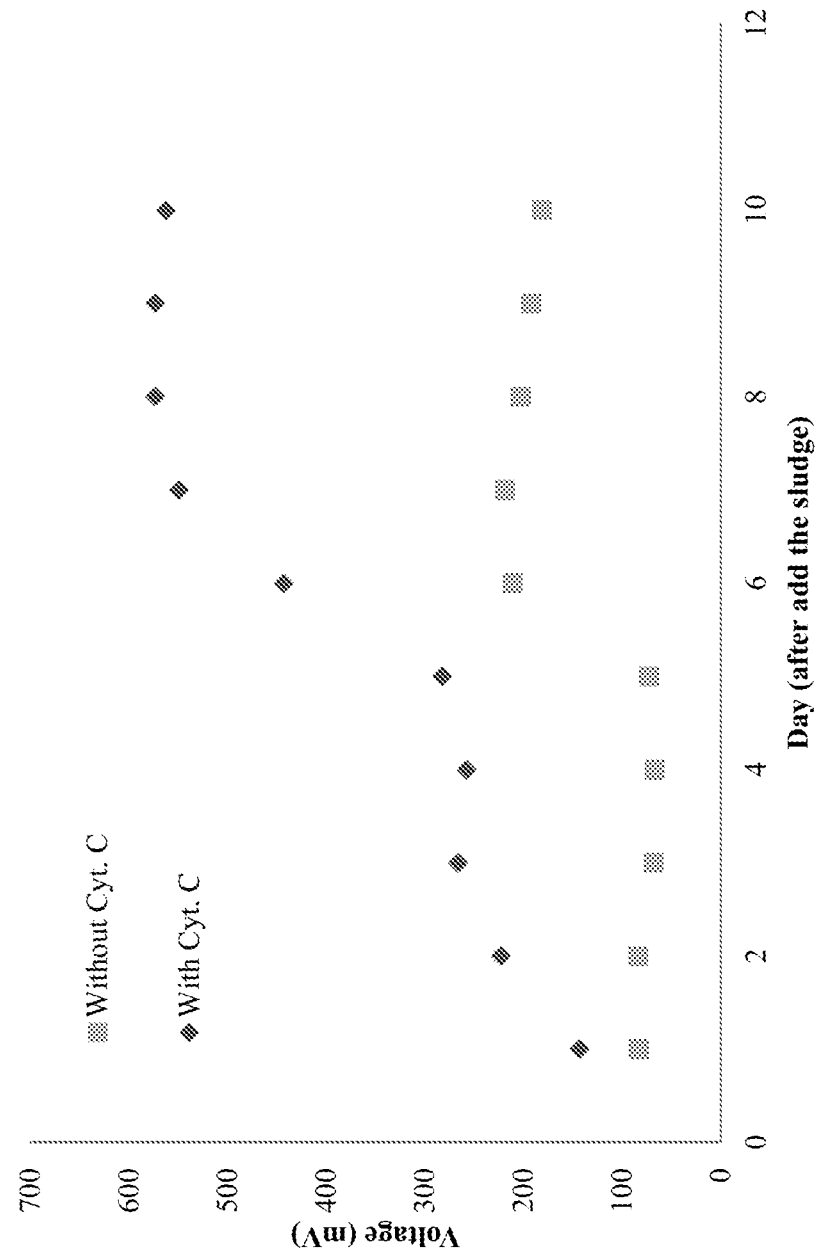
FIG. 11 is a graph showing voltage measurements in MFCs with or without cytochrome C. Circles indicate measurements made in MFC reactors with cytochrome C from equine heart. Squares indicate measurements made in MFC reactors without cytochrome C. The strain of this reactor was used *M. acetivorans*/pES1MATmcr3/*G. sulfurreducens*/sludge. These graphs are showing measurements after adding sludge.

Effect of cytochrome C as an electron carrier was measured. The maximum voltage of the MFC with cytochrome C was 573.2 mV-143.1 mV (original voltage)=430.1 mV. The maximum voltage of the MFC without cytochrome C was 218.7 mV-82.7 mV (original voltage)=136.0 mV, showing a 3.2-fold higher maximum voltage in the MFC with cytochrome C compared to the MFC without cytochrome C indicating that electron transfer efficiency is improved by adding cytochrome C in the MFC. FIG. 11 is a graph showing voltage measurements in MFCs with or without cytochrome C. Circles indicate measurements made in MFC reactors with cytochrome C from equine heart. Squares indicate measurements made in MFC reactors without cytochrome C. The strain of this reactor was used M. acetivorans/pES1MATmcr3/G. sulfurreducens/sludge. These graphs are showing measurements after adding sludge.

Preparation of HSYE-Methanol medium (anolyte) for methanogens, such as Methanosarcina acetivorans, and Inoculation (HSNR medium is same recipe with add on of resazurin, Yeast extract, and methanol.)

Stock Solutions (1) 100× Trace element solution (store at 4° C. inside a refrigerator)

| Chemical name | Amount (gm/L) | Concentration (mM) (100X) | Working concentration (1X) mM | Chemical company with catalogue (MW(g/mol)) |
|---|---|---|---|---|
| Nitrilotriacetic acid | 1.5 | 7.85 | 0.0785 | Sigma- N9877-191.14 |
| $MgSO_4$—$7H_2O$ | 3.0 | 12.2 | 0.122 | Sigma-M2773- 246.47 |
| $MnSO_4$—$H_2O$ (monohydrate) | 0.5 | 2.96 | 0.0296 | SIGMA- M7634-169.02 |
| NaCl | 1.0 | 17.11 | 0.1711 | Fisher- S271-1-58.44 |
| $FeSO_4$—$7H_2O$ | 0.1 | 0.36 | 0.0036 | Fisher-I149-3- 278.01 |
| $CoCl_2$—$6H_2O$ or $CoSO_4$—$7H_2O$ | 0.18 or 0.1 | 0.756 or 0.356 | 0.00756 or 0.00356 | Fisher-C371-100 (237.93) or Sigma-230383-100G (281.0) |
| $CaCl_2$—$2H_2O$ | 0.1 | 0.68 | 0.0068 | EMD-CX0134-1 (147.01) |
| $ZnSO_4$—$7H_2O$ or $ZnCl_2$ | 0.17 or 0.08 | 0.59 or 0.59 | 0.0059 or 0.0059 | Fisher- Z76-500 (287.56) or Fisher-Z34-12 (136.3) |
| $CuSO_4$—$5H_2O$ | 0.01 | 0.04 | 0.0004 | Fisher-C-493 (249.68) |
| $KAl(SO_4)_2$—$12H_2O$ | 0.01 | 0.02 | 0.0002 | Fisher-A-601 (474.39) |
| $H_3BO_3$ | 0.01 | 0.16 | 0.0016 | Fisher-A74-1 (61.83) |
| $Na_2MoO_4$ | 0.025 | 0.103 | 0.00103 | Fisher-S336 (241.95) |
| $NiCl_2$—$6H_2O$ | 0.024 | 0.101 | 0.00101 | Sigma-N-5756 (237.7) |

(2) 100× Vitamin solution (store at 4° C. inside a refrigerator)

| Chemical name | Amount (gm/L) | Concentration (mM) (100X) | Working concentration (1X) mM | Chemical company with catalogue (MW(g/mol)) |
|---|---|---|---|---|
| Biotin | 0.02 | 0.08 | 0.0008 | MP-biomedicals-101023 or Sigma-B4501 (244.31) |
| Folic acid | 0.02 | 0.045 | 0.00045 | Sigma-F7876 (441.4) |
| Pyridoxine hydrochloride | 0.1 | 0.49 | 0.0049 | Sigma-P-9755 (205.6) |
| Thiamine hydrochloride | 0.05 | 0.148 | 0.00148 | Sigma-T4625 (337.3) |
| Riboflavin | 0.05 | 0.133 | 0.00133 | Sigma-R-4500 (376.4) |
| Nicotinic acid | 0.05 | 0.406 | 0.00406 | Sigma-N-4126 (123.1) |
| DL-calcium pantothenate | 0.05 | 0.21 | 0.0021 | Sigma-P2250 (238.3) |
| Vitamin $B_{12}$ | 0.001 | 0.00074 | 0.0000074 | Sigma-V-2876 (1355.4) |
| p-Aminobenzoic acid | 0.05 | 0.365 | 0.00365 | Sigma-A-9878 (137.1) |
| Lipoic acid (thioctic acid) | 0.05 | 0.24 | 0.0024 | Sigma-T5625 (206.3) |

(3) 0.1% (1 g/L) Resazurin (1000× stock) (storage at 4° C. inside a refrigerator)

(4) $Na_2S$-$9H_2O$ (25 g/L) (100× stock) (filter-sterilize and store inside the anaerobic chamber to remove oxygen)

(5) 50% (v/v) Methanol (100× stock) (filter-sterilize and store inside the anaerobic chamber to remove oxygen)

(6) 1 M $KH_2PO_4$ (1.36 g/10 mL for 1-L medium) (filter-sterilize and store inside the anaerobic chamber to remove oxygen)

Weigh 0.5 g of Cysteine-HCl for 1-L medium (keep at a room temperature)

Weigh 1 g of $NH_4Cl$ for 1-L medium (keep at a room temperature)

For HSYE medium: weigh 2.5 g of Yeast Extracts for 1-L medium (keep at a room temperature) (this option is to make HSYE medium)

Procedures (for 1-L Medium)

Outside the anaerobic chamber, add following chemicals in 970 mL of $ddH_2O$ in following order: NaCl (23.4 g), $NaHCO_3$ (3.8 g), KCl (1.0 g), $MaCl_2$-$6H_2O$ (11.0 g) and $CaCl_2$-$2H_2O$ (0.3 g) and dissolve while stirring. Outside the anaerobic chamber, add 10 mL of 100× Trace element solution to the above colorless salt solution and mix. Outside the anaerobic chamber, add 10 mL of 100× Vitamin solution and mix properly. The color turns yellow.

Outside the anaerobic chamber, add 1 mL of 1000× Resazurin solution and mix properly and at this step, the color turns blue. Outside the anaerobic chamber, heat the above solution for exactly 12 min while gently stirring and sparging with nitrogen gas (around 20 scale in the flow meter)

Outside the anaerobic chamber, add Cysteine-HCl (0.5 g for 1-L medium) and mix until the powder can be dissolved. Place the solution in the anaerobic chamber until cool and colorless. After the solution is cool and colorless, inside the anaerobic chamber, add 5.0 mL of 1 M $KH_2PO_4$ slowly while mixing. Then, inside the anaerobic chamber, add 1 g of $NH_4Cl$, mix the medium and purge gases until colorless. Inside the anaerobic chamber, add 2.5 g of Yeast Extracts and mix. Distribute the colorless medium into each vial. Inside the anaerobic chamber, connect the rubber stopper to each vial.

Outside the anaerobic chamber, seal the rubber stopper by an aluminum cap. Autoclave all filled vials at 121° C. for 20 min. Leave at room temperature until any precipitation dissolves. Once, precipitation disappears, insider the anaerobic chamber, add 1 mL of 100× stock $Na_2S$-$9H_2O$ (2.5% $Na_2S$-$9H_2O$, per 100 mL of each medium) and 1 mL of 100× stock methanol (50% methanol, per 100 ml of each medium) in each tube/bottle (use a needle and a cylinder). Add 100 µL (per 100 mL of each medium) of 2 mg/mL puromycin. In this example, *Methanosarcina acetivorans*/pES1-MATmcr3 used as an inoculum has the plasmid harboring ANME-1 Mcr which should be required to maintain the plasmid by puromycin. Inside the anaerobic chamber, add 1 mL of *Methanosarcina acetivorans*/pES1-MATmcr3 cells. Take out all the vials from the anaerobic chamber and incubate the vials at 37° C.

Item List

Item 1. A microbial consortium for generating electrical current from methane, the microbial consortium comprising: an engineered methanogen that contains a heterologous nucleic acid sequence encoding methyl-coenzyme M reductase derived from an anaerobic methane oxidizer; an exoelectrogen microbe that produces electrically-conductive appendages and/or one or more types of electron carrier, such as but not limited to FMN, FAD, riboflavin or a combination of any two or more thereof, and a sludge or a sludge isolate component.

Item 2. The microbial consortium of item 1, wherein the sludge or sludge isolate component comprises one or more types of microbe and/or humic acids.

Item 3. The microbial consortium of item 1 or item 2, wherein the sludge or sludge isolate component comprises or is selected from the group consisting of: *Paracoccus* spp., *Geotoga* spp., *Geobacter* spp., *Methanosarcina* spp., *Garciella* spp., humic acids, or combination thereof.

Item 4. The microbial consortium of any of items 1 to 3, wherein the heterologous nucleic acid sequence encoding the methyl-coenzyme M reductase is an mRNA sequence or a DNA sequence.

Item 5. The microbial consortium of any of items 1 to 4, wherein the heterologous nucleic acid sequence encoding the methyl-coenzyme M reductase is contained in a plasmid.

Item 6. The microbial consortium any of items 1 to 5, wherein the engineered methanogen is *Methanosarcina acetivorans*.

Item 7. The microbial consortium of any of items 1 to 6, wherein the engineered methanogen, such as but not limited to, *Methanosarcina acetivorans*, is air-adapted.

Item 8. The microbial consortium any of items 1 to 7, wherein the exoelectrogen microbe is chosen from *Geobacter* spp., *Shewanella* spp., or combination thereof.

Item 9. The microbial consortium of item 8, wherein: the *Geobacter* spp. are chosen from the group consisting of *Geobacter anodireducens, Geobacter argillaceus, Geobacter bemidjiensis, Geobacter bremensis, Geobacter chapellei, Geobacter daltonii, Geobacter grbiciae, Geobacter hydrogenophilus, Geobacter lovley, Geobacter luticola, Geobacter metallireducens, Geobacter pelophilus, Geobacter pickeringii, Geobacter psychrophilus, Geobacter soli, Geobacter sulfurreducens, Geobacter thiogenes, Geobacter toluenoxydans, Geobacter uraniireducens*, and a combination of any two or more thereof; and the *Shewanella* spp. are selected from the group consisting of: *Shewanella abyssi, Shewanella aestuarii, Shewanella algae, Shewanella algidipiscicola, Shewanella amazonensis, Shewanella aquimarina, Shewanella arctica, Shewanella atlantica, Shewanella baltica, Shewanella basaltic, Shewanella benthica, Shewanella canadensis, Shewanella chilikensis, Shewanella colwelliana, Shewanella corallii, Shewanella decolorationis, Shewanella denitrificans, Shewanella dokdonensis, Shewanella donghaensis, Shewanella fidelis, Shewanella fodinae, Shewanella frigidmarina, Shewanella gaetbuli, Shewanella gelidimarina, Shewanella glacialipiscicola, Shewanella hafniensis, Shewanella halifaxensis, Shewanella halitois, Shewanella hanedai, Shewanella indica, Shewanella irciniae, Shewanella japonica, Shewanella kaireitica, Shewanella litorisediminis, Shewanella livingstonensis, Shewanella loihica, Shewanella mangrovi, Shewanella marina, Shewanella marinintestina, Shewanella marisflavi, Shewanella morhuae, Shewanella olleyana, Shewanella oneidensis, Shewanella piezotolerans, Shewanella pacifica, Shewanella pealeana, Shewanella piezotolerans, Shewanella penumatophori, Shewanella putrefaciens, Shewanella sairae, Shewanella schegeliana, Shewanella sediminis, Shewanella seohaensis, Shewanella spongiae, Shewanella surugensis, Shewanella upenei, Shewanella vesiculosa, Shewanella violacea, Shewanella waksmanii, Shewanella woodyi, Shewanella xiamenensis*, and a combination of any two or more thereof.

Item 10. The microbial consortium of item 8, wherein: the *Geobacter* spp. are chosen from: *Geobacter metallireducens, Geobacter sulfurreducens*, and a combination thereof; and the *Shewanella* spp. are chosen from: *Shewanella putrefaciens*, IR-1, *Shewanella oneidensis* DSP10, and a combination thereof.

Item 11. The microbial consortium any of items 1 to 10, wherein the exoelectrogen microbe is chosen from *Geobacter* spp.

Item 12. The microbial consortium any of items 1 to 11, wherein the exoelectrogen microbe is *Geobacter sulfurreducens, Geobacter metallireducens*, or a combination thereof.

Item 13. The microbial consortium any of items 1 to 12, wherein the sludge or sludge isolate component comprises a component chosen from: *Paracoccus* spp., *Geotoga* spp., *Garciella* spp., humic acids, and a combination of any two or more thereof. Optionally, the sludge isolate component is a component chosen from: *Paracoccus* spp., *Geotoga* spp., *Garciella* spp., humic acids, and a combination of any two or more thereof.

Item 14. The microbial consortium any of items 1 to 13, wherein the sludge comprises, or the sludge isolate component is or comprises, a microbe chosen from *Paracoccus* spp.

Item 15. The microbial consortium any of items 1 to 13, wherein the sludge comprises, or the sludge isolate component is or comprises, a humic acid.

Item 16. The microbial consortium any of items 1 to 15 wherein the sludge or sludge isolate component is methane-acclimated.

Item 17. A microbial fuel cell for generating electrical current from methane, the microbial fuel cell comprising: an anode chamber comprising an anode, a first fluid, and methane, wherein the first fluid comprises a microbial consortium according to any of items 1 to 16; a cathode chamber in selective communication with the anode chamber, the cathode chamber comprising a cathode in electrical communication with the anode and a second fluid, and a cation exchange membrane disposed between the anode chamber and the cathode chamber.

Item 18. The microbial fuel cell of item 17, wherein the anode chamber comprises a headspace, and wherein the methane is provided in the headspace.

Item 19. The microbial fuel cell of item 17 or item 18, wherein the first fluid comprises an inoculation medium.

Item 20. The microbial fuel cell of item 17, item 18 or item 19, wherein the second fluid comprises a catholyte.

Item 21. A method for generating electrical current, the method comprising:

providing a microbial consortium according to any of items 1 to 16 an anode chamber of a microbial fuel cell, wherein:

the microbial fuel cell comprises:

the anode chamber comprising an anode and methane, a cathode chamber in selective communication with the anode chamber, the cathode chamber comprising a cathode in electrical communication with the anode and a second fluid, and a cation exchange membrane disposed between the anode chamber and the cathode chamber, wherein the microbial fuel cell generates electrical current anaerobically.

Item 22. The method according to item 21, wherein cytochrome C is included in the first fluid in the anode chamber to achieve a concentration in the range of about 200 nM-200 µM, such as 250 nM-100 µM.

Item 23. The microbial consortium, microbial fuel cell and/or method for generating electrical current according to any of items 1 to 23 wherein the heterologous nucleic acid sequence encoding methyl-coenzyme M reductase derived from an anaerobic methane oxidizer comprises SEQ ID NO:2 or a variant thereof encoding methyl-coenzyme M reductase submit alpha or a variant thereof, SEQ ID NO:4 or a variant thereof encoding methyl-coenzyme M reductase submit beta or a variant thereof and SEQ ID NO:6 or a variant thereof encoding methyl-coenzyme M reductase submit gamma or a variant thereof.

Item 24. The microbial consortium, microbial fuel cell and/or method for generating electrical current according to any of items 1 to 23 wherein the engineered methanogen contains a heterologous nucleic acid sequence encoding methyl-coenzyme M reductase derived from an anaerobic methane oxidizer and a heterologous nuclei acid sequence encoding puromycin resistance and wherein puromycin is included in the anode chamber amounts in the range of about 0.5 micrograms/milliliter to about 10 micrograms/milliliter, such as about 0.75 micrograms/milliliter to about 7.5 micrograms/milliliter, such as about 1 microgram/milliliter to about 5 micrograms/milliliter, such as about 2 micrograms/milliliter.

Sequences

Methyl-coenzyme M reductase (Mcr), alpha subunit, ANME-1 SEQ ID NO: 1
MPYNDIQHNFLKAMSDKFAEKPESTATEFYTYGGIAQKGGMRKREFIAEA
SKIVDSRVNSTPAYNPDAGMPQGQRYLMPYMMNHTDIMVNADDLHWINNA
AMQQAWDDMKRGIVLGLDDAHGLLEARLGKEVTPDTISNYMEVLNHALPG
GAVIQEHMVETKFMLVNDSYAKIFSGDDDLVDSVDRRFILDINKEFAAGY
DKPGEQADQLKDAIGKKIWQILWMPTVVARQTDGGTMFRWVGMQVGMTMI
NAYKLCAGESVTGEFAYYAKHAAVVQLSNYMPVKRARSHNEPGGMPLGIN
ADSTRSPALFPNDPIRAELESIAVAAMVYDQLWFGTYMSGGVGFTQYASA
TYTDNILEDFCYKGCEIGLDYAGGKMASIKGDKLNMDILEEIIRAENDYA
LTQYEAYPTVAESHFGGSVRACCAAAGCGSAVACATGLAQPALSAWSLSM
LGHYERVGRLGFFGYDLQDQCTACGSYSYQSDEGMPFEMRGVNYPNYAMN
VGHQSAYAGLVAGAHSANHDAWVLSPLWKVAFSDRDLPFDRGYVTREYGL
GANREYTKVAGERDLIIAGHYGREPGAKL SEQ ID NO: 2 encoding Methyl-coenzyme M reductase, alpha subunit, ANME-1
ATGCCATATAATGATATACAGCACAATTTCCTGAAAGCGATGTCAGATAA
GTTCGCGGAGAAGCCAGAGAGTACAGCGACCGAGTTCTATACGTACGGCG
GTATAGCGCAGAAAGGAGGAATGAGAAAGAGGGAGTTCATAGCGGAAGCA
TCGAAGATAGTAGATAGCCGAGTCAACTCAACGCCAGCATACAATCCGGA
TGCGGGTATGCCACAAGGGCAGAGATACCTGATGCCATACATGATGAACC
ACACGGACATCATGGTAAACGCAGATGACCTGCACTGGATCAACAATGCC
GCGATGCAGCAGGCCTGGGATGATATGAAGAGAGGAATTGTCCTGGGACT
GGACGATGCACACGGACTGTTAGAAGCGAGATTGGGCAAGGAAGTTACGC
CAGATACAATAAGCAACTACATGGAAGTGTTGAACCACGCGCTGCCGGGT
GGTGCGGTAATTCAGGAGCACATGGTAGAGACGAAGCCGATGCTGGTGAA
TGACAGCTATGCCAAGATATTCTCCGGAGATGACGACCTTGTAGATTCTG
TTGACAGGAGATTCATTCTGGACATAAACAAGGAATTCGCAGCAGGCTAT
GATAAACCGGGCGAGCAGGCCGACCAGTTGAAAGATGCAATTGGCAAGAA
GATCTGGCAGATCCTCTGGATGCCGACTGTTGTAGCACGACAGACAGATG
GAGGTACGATGTTCAGATGGGTAGGTATGCAGGTCGGAATGACAATGATA
AACGCATACAAGCTGTGTGCAGGAGAATCAGTCACGGGTGAGTTCGCATA
CTACGCGAAGCACGCTGCTGTGGTTCAGTTGTCGAACTACATGCCAGTAA
AGAGAGCAAGGTCACACAATGAACCTGGTGGTATGCCATTAGGTATAAAC
GCAGACAGTACACGGTCACCAGCGTTGTTCCCGAACGACCCGATAAGGGC
TGAGCTGGAGAGTATCGCAGTTGCGGCTATGGTCTATGACCAGTTGTGGT
TCGGAACGTACATGTCAGGTGGTGTAGGATTCACGCAGTACGCAAGTGCG
ACCTACACGGACAACATCCTGGAGGACTTCTGCTACAAGGGCTGCGAAAT
CGGACTGGATTACGCAGGCGGCAAGATGGCTTCGATAAAGGGCGACAAGC
TCAACATGGACATCCTGGAGGAGATAATAAGAGCAGAGAACGATTATGCA
CTGACGCAGTATGAAGCATATCCAACAGTAGCGGAATCTCACTTCGGTGG
ATCTGTTAGAGCGTGCTGTGCAGCAGCGGGATGTGGTAGTGCAGTTGCAT
GCGCAACAGGACTTGCACAACCTGCATTGAGTGCGTGGTCACTGTCTATG
CTGGGACACTATGAGCGTGTTGGAAGACTCGGATTCTTCGGGTACGACTT
GCAAGATCAGTGTACGGCATGCGGCTCGTATTCATACCAGAGTGATGAGG
GAATGCCATTTGAGATGCGCGGTGTGAACTATCCGAACTACGCGATGAAC
GTCGGGCACCAGAGTGCGTACGCAGGTCTAGTTGCTGGAGCACACTCTGC
AAATCATGACGCATGGGTGCTGTCACCGTTGTGGAAAGTAGCGTTCTCGG
ACCGTGACCTACCGTTCGACCGTGGTTACGTGACCAGAGAGTACGGACTG
GGTGCAAACAGAGAATACACCAAGGTCGCCGGAGAGAGATCTGATTAT
AGCAGGTCACTACGGCAGAGAACCCGGTGCAAAACTGTAA Methyl-coenzyme M reductase, beta subunit, ANME-1 SEQ ID NO: 3
MADEIDLYDDKGKKLAAGVPLQNISPLKNAAIKKIVNLTIRTGAVDLAGL
EKKFATGAIAGRGMVIRGVNRNLPIVDKAKEIAKAVEDMLRVESGDDTNV
ELIAGGKRMMVQPPTARILSDYSVGLTASMGALTHAIIDVCNVSMWDAPY
VHAGVWGMYPQNPDPGDGAVKMLVDIPMKNEGPGFTLRNIPVNHLAATVR
KRAMQGAGLTMILEEAAQFEMGNCMGFHERGHLLDLAYEGLNANNLLYSL
IKDNGQDGSLGDVIYAAVEKAKADGVIKSLKKMPSGFTVYDADDMQLWNA
YACTAMLAGVCVNCASMRAGQPVPGNIMQACCLIERETGLPGPDFGMAQG
ASVSSSFFSHSIYGGGGPGVFYGNHIVTRHAKGQFIPCFCAAMCIDADTM
YFSPARTSALYGEVLGAIPEFAEPMRAVAEAAK SEQ ID NO: 4 encoding Methyl-coenzyme M reductase, beta subunit, ANME-1
ATGGCAGATGAAATAGATTTATATGACGACAAAGGCAAGAAGTTAGCGGC
TGGTGTACCATTACAGAACATCAGTCCGCTGAAGAATGCAGCGATAAAGA
AGATAGTTAACCTGACCATCAGGACAGGTGCTGTTGACTTAGCAGGTCTG
GAGAAGAAGTTCGCAACCGGCGCAATTGCGGGTAGAGGTATGGTAATCCG
GGGCGTAAATAGGAACTTACCGATAGTGGACAAAGCGAAAGAGATAGCGA
AAGCAGTAGAGGACATGTTGCGCGTTGAGTCAGGAGACGACACAAACGTA
GAATTAATCGCAGGTGGAAAGCGAATGATGGTGCAGCCACCAACCGCGAG
AATACTATCCGATTATTCGGTTGGTCTGACCGCGTCAATGGGTGCGCTAA
CGCATGCGATTATTGACGTCTGCAACGTGAGTATGTGGGATGCACCGTAT
GTGCATGCTGGTGTGTGGGGTATGTACCCACAAAATCCGGATCCCGGTGA
TGGGGCAGTAAAGATGCTCGTGGATATACCGATGAAGAATGAGGGACCGG
GTTTCACGCTGAGGAACATACCTGTGAACCACTTAGCAGCGACAGTGAGG
AAGAGAGCGATGCAAGGTGCGGGCCTGACCATGATTCTGGAAGAGGCAGC
GCAGTTCGAGATGGGTAACTGTATGGGACCGCATGAGCGTGGTCACCTTC
TGGATCTTGCGTATGAAGGACTGAATGCGAACAACCTGTTGTATAGCCTG
ATAAAAGACAACGGCCAGGACGGGTCACTTGGCGATGTGATATACGCTGC
GGTGGAGAAAGCGAAAGCAGACGGTGTGATAAAGTCACTGAAGAAGATGC
CATCCGGATTCACAGTGTATGACGCGGATGACATGCAGTTGTGGAACGCA
TACGCATGCACGGCTATGCTTGCGGGTGTATGTGTGAACTGCGCATCAAT
GCGTGCAGGTCAGCCAGTACCGGGTAACATTATGCAAGCCTGCTGTCTGA
TAGAGAGAGAACAGGACTGCCTGGACCAGACTTTGGAATGGCTCAGGGT
GCGTCAGTATCGAGCTCGTTCTTCTCGCACTCCATATATGGAGGCGGTGG
ACCGGGTGTGTTCTATGGGAACCACATCGTGACGAGGCATGCGAAGGGTC
AGTTCATACCCTGTTTCTGTGCTGCGATGTGCATAGATGCGGACACGATG
TATTTCTCACCAGCGAGGACGTCAGCATTGTATGGGGAAGTATTGGGTGC
AATACCAGAATTTGCAGAACCAATGAGGGCAGTTGCGGAGGCTGCCAAGT
AA

Sequences

Methyl-coenzyme M reductase, gamma subunit, ANME-1
SEQ ID NO: 5
MPQFTAGNSHVAQNRRNYMDPSYKLEKLRDIPEEDIVRLLAHRAPGEEYK
SIHPPLEEMEEPDCAVRQIVKPTEGAAAGDRIRYVQYTDSMFFSPITPYQ
RAWEALNRYKGVDPGVLSGRTIIEARERDIEKIAKIEVDCELYDTARTGL
RGRTVHGHAVRLDKDGMMFDALRRWSRGADGTVTYVKDMIGGAMDKEVTL
GKPLSDAELLKKTTMYRNAQGGVWQEADDPESMDVTAQIHWKRSVGGFQP
WAKMKDIKGGKKDVGVKNLKLFTPRGGVE SEQ ID NO: 6 encoding Methyl-coenzyme M reductase,
gamma subunit, ANME-
ATGCCACAATTTACAGCGGGAAATAGCCATGTAGCACAAAACAGAAGAAA
CTACATGGACCCAAGCTACAAATTAGAGAAACTGAGAGACATACCAGAAG
AAGACATTGTGAGATTGCTTGCGCACCGTGCACCGGGAGAGGAGTACAAG
AGCATCCATCCACCATTGGAAGAGATGGAAGAGCCGGACTGCGCGGTTCG
TCAGATAGTGAAGCCAACAGAAGGCGCAGCAGCAGGTGACAGGATACGAT
ACGTGCAGTACACCGATTCGATGTTCTTCTCACCGATAACGCCTTACCAG
CGTGCATGGGAAGCATTGAACCGATATAAGGGTGTGGACCCAGGAGTGCT
GTCAGGAAGGACGATCATAGAAGCACGAGAGCGAGATATAGAGAAGATAG
CGAAAATCGAGGTTGATTGCGAGCTATACGATACAGCAAGAACCGGCCTG
AGAGGAAGGACAGTGCACGGGCACGCAGTCCGACTGGACAAGGACGGTAT
GATGTTCGATGCACTACGAAGATGGTCAAGAGGTGCAGATGGAACAGTAA
CCTACGTGAAGGATATGATCGGCGGTGCAATGGACAAGGAAGTAACGTTA
GGAAAGCCACTGTCTGATGCAGAGCTGCTGAAGAAAACGACTATGTACAG
GAACGCACAGGGCGGAGTCTGGCAAGAAGCGGATGATCCCGAGTCAATGG
ACGTAACTGCTCAGATACACTGGAAAAGGTCAGTAGGTGGATTCCAACCA
TGGGCAAAGATGAAGGACATAAAAGGTGGAAAGAAGGACGTAGGCGTGAA
GAACTTGAAATTATTTACACCAAGAGGAGGAGTGGAATAA It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination.

All documents cited are incorporated herein by reference; the citation of any document is not to be construed as an admission that it is prior art with respect to the present disclosure.

It is to be further understood that where descriptions of various embodiments use the term "comprising," and/or "including" those skilled in the art would understand that in some specific instances, an embodiment can be alternatively described using language "consisting essentially of" or "consisting of."

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The devices and methods described herein are presently representative of preferred embodiments, exemplary, and not intended as limitations on the scope of the disclosure. Changes therein and other uses will occur to those skilled in the art. Such changes and other uses can be made without departing from the scope of the invention as set forth in the claims.

What is claimed is:

1. A microbial consortium for generating electrical current from methane, the microbial consortium comprising:
   an engineered methanogen that contains a heterologous nucleic acid sequence encoding methyl-coenzyme M reductase derived from an anaerobic methane oxidizer;
   an exoelectrogen microbe that produces electrically-conductive appendages and/or one or more types of electron carrier; and
   a sludge or a sludge isolate component.

2. The microbial consortium of claim 1, wherein the sludge or sludge isolate component comprises one or more types of microbe and/or humic acids.

3. The microbial consortium of claim 1, wherein the sludge isolate component is selected from the group consisting of: *Paracoccus* spp., *Geotoga* spp., *Geobacter* spp., *Methanosarcina* spp., *Garciella* spp., humic acids, or combination thereof.

4. The microbial consortium of claim 1, wherein the engineered methanogen is *Methanosarcina acetivorans*.

5. The microbial consortium of claim 4, wherein the engineered *Methanosarcina acetivorans* is air-adapted.

6. The microbial consortium of claim 1, wherein the exoelectrogen microbe is chosen from *Geobacter* spp., *Shewanella* spp., or combination thereof.

7. The microbial consortium of claim 6, wherein:
   the *Geobacter* spp. are chosen from the group consisting of: *Geobacter anodireducens, Geobacter argillaceus, Geobacter bemidjiensis, Geobacter bremensis, Geobacter chapellei, Geobacter daltonii, Geobacter grbiciae, Geobacter hydrogenophilus, Geobacter lovley, Geobacter luticola, Geobacter metallireducens, Geobacter pelophilus, Geobacter pickeringii, Geobacter psychrophilus, Geobacter soli, Geobacter sulfurreducens, Geobacter thiogenes, Geobacter toluenoxydans, Geobacter uraniireducens*, and a combination of any two or more thereof; and
   the *Shewanella* spp. are selected from the group consisting of: *Shewanella abyssi, Shewanella aestuarii, Shewanella algae, Shewanella algidipiscicola, Shewanella amazonensis, Shewanella aquimarina, Shewanella arctica, Shewanella atlantica, Shewanella baltica, Shewanella basaltis, Shewanella benthica, Shewanella canadensis, Shewanella chilikensis, Shewanella colwelliana, Shewanella corallii, Shewanella decolorationis, Shewanella denitrificans, Shewanella dokdonensis, Shewanella donghaensis, Shewanella fidelis, Shewanella fodinae, Shewanella frigidmarina, Shewanella gaetbuli, Shewanella gelidimarina, Shewanella glacialipiscicola, Shewanella hafniensis, Shewanella halifaxensis, Shewanella halitois, Shewanella hanedai, Shewanella indica, Shewanella irciniae, Shewanella japonica, Shewanella kaireitica, Shewanella litorisediminis, Shewanella livingstonensis, Shewanella loihica, Shewanella mangrovi, Shewanella marina, Shewanella marinintestina, Shewanella marisflavi, Shewanella morhuae, Shewanella olleyana, Shewanella oneidensis, Shewanella piezotolerans, Shewanella pacifica, Shewanella pealeana, Shewanella piezotolerans, Shewanella penumatophori, Shewanella putrefaciens, Shewanella sairae, Shewanella schegeliana, Shewanella sediminis, Shewanella seohaensis, Shewanella spongiae, Shewanella surugensis, Shewanella upenei, Shewanella vesiculosa, Shewanella violacea, Shewanella waksmanii, Shewanella woodyi, Shewanella xiamenensis*, and a combination of any two or more thereof.

8. The microbial consortium of claim 6, wherein:
   the *Geobacter* spp. are chosen from: *Geobacter metallireducens, Geobacter sulfurreducens*, and a combination thereof; and
   the *Shewanella* spp. are chosen from: *Shewanella putrefaciens* IR-1, *Shewanella oneidensis* DSP10, and a combination thereof.

9. The microbial consortium of claim 1, wherein the exoelectrogen microbe is *Geobacter sulfurreducens, Geobacter metallireducens*, or a combination thereof.

10. The microbial consortium of claim 1, wherein the sludge isolate component is chosen from: *Paracoccus* spp., *Geotoga* spp., *Garciella* spp., humic acids, and a combination of any two or more thereof.

11. The microbial consortium of claim 1, wherein the sludge isolate component is a humic acid.

12. The microbial consortium of claim 1, wherein the sludge or sludge isolate component is methane-acclimated.

13. A microbial fuel cell for generating electrical current from methane, the microbial fuel cell comprising:
   an anode chamber comprising an anode, a first fluid, and methane, wherein the first fluid comprises a microbial consortium according to of claim 1;
   a cathode chamber in selective communication with the anode chamber, the cathode chamber comprising a cathode in electrical communication with the anode and a second fluid, and
   a cation exchange membrane disposed between the anode chamber and the cathode chamber.

14. The microbial fuel cell of claim 13, wherein the anode chamber comprises a headspace, and wherein the methane is provided in the headspace.

15. The microbial fuel cell of claim 13, wherein the first fluid comprises an inoculation medium.

16. The microbial fuel cell of claim 13, wherein the second fluid comprises a catholyte.

17. A method for generating electrical current, the method comprising:
   providing a microbial consortium according to claim 1 an anode chamber of a microbial fuel cell, wherein:
   the microbial fuel cell comprises:
      the anode chamber comprising an anode and methane,
      a cathode chamber in selective communication with the anode chamber, the cathode chamber comprising a cathode in electrical communication with the anode and a second fluid, and
      a cation exchange membrane disposed between the anode chamber and the cathode chamber, wherein the microbial fuel cell generates electrical current anaerobically.

18. The method according to claim 17, wherein cytochrome C is included in the first fluid in the anode chamber to achieve a concentration in the range of about 200 nM-200 µM, such as 250 nM-100 µM.

19. The microbial consortium for generating electrical current according to claim 1 wherein the heterologous nucleic acid sequence encoding methyl-coenzyme M reductase derived from an anaerobic methane oxidizer comprises SEQ ID NO:2 or a variant thereof encoding methyl-coenzyme M reductase submit alpha or a variant thereof, SEQ ID NO:4 or a variant thereof encoding methyl-coenzyme M reductase submit beta or a variant thereof and SEQ ID NO:6 or a variant thereof encoding methyl-coenzyme M reductase submit gamma or a variant thereof.

20. The microbial consortium for generating electrical current according to claim 1 wherein the engineered methanogen contains a heterologous nucleic acid sequence encoding methyl-coenzyme M reductase derived from an anaerobic methane oxidizer and a heterologous nuclei acid sequence encoding puromycin resistance and wherein puromycin is included in the anode chamber amounts in the range of about 0.5 micrograms/milliliter to about 10 micrograms/milliliter, such as about 0.75 micrograms/milliliter to about 7.5 micrograms/milliliter, such as about 1 microgram/milliliter to about 5 micrograms/milliliter, such as about 2 micrograms/milliliter.

* * * * *